United States Patent
Scholl et al.

(10) Patent No.: US 10,188,480 B2
(45) Date of Patent: Jan. 29, 2019

(54) SYSTEMS AND METHODS FOR PERFORMING SPINE SURGERY

(71) Applicant: NUVASIVE, INC., San Diego, CA (US)

(72) Inventors: Thomas U Scholl, San Diego, CA (US); Autumn Sutterlin, San Diego, CA (US); Elizabeth Blaylock, San Diego, CA (US); Donald J Blaskiewicz, San Diego, CA (US); Neill M Wright, San Diego, CA (US); Robert E Isaacs, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 15/440,991

(22) Filed: Feb. 23, 2017

(65) Prior Publication Data

US 2017/0231710 A1 Aug. 17, 2017

Related U.S. Application Data

(63) Continuation of application No. PCT/US2017/014626, filed on Jan. 23, 2017.
(Continued)

(51) Int. Cl.
*A61B 17/70* (2006.01)
*A61B 17/88* (2006.01)
(Continued)

(52) U.S. Cl.
CPC .......... *A61B 90/06* (2016.02); *A61B 5/00* (2013.01); *A61B 5/0082* (2013.01); *A61B 5/1071* (2013.01); *A61B 5/743* (2013.01); *A61B 5/7475* (2013.01); *A61B 6/461* (2013.01); *A61B 6/487* (2013.01); *A61B 17/7049* (2013.01); *A61B 17/8863* (2013.01); *A61B 18/18* (2013.01);
(Continued)

(58) Field of Classification Search
CPC ....... A61B 90/06; A61B 90/361; A61B 6/461; A61B 6/478; A61B 18/18; A61B 2090/067; A61B 17/8863; A61B 17/7074–17/7092; A61B 17/50; A61B 17/58
USPC ............... 606/86 A, 99, 101, 104, 246–279; 600/300, 373, 594, 587, 425, 407, 473; 269/3, 6; 72/31.04, 296–310; 29/432, 29/260, 259, 276, 278; 700/165, 98; 623/901
See application file for complete search history.

(56) References Cited

U.S. PATENT DOCUMENTS

| 5,658,286 A | 8/1997 | Sava |
| RE42,226 E | 3/2011 | Foley |

(Continued)

FOREIGN PATENT DOCUMENTS

| DE | 102011006574 | 10/2012 |
| WO | WO-2009035358 | 3/2009 |

(Continued)

OTHER PUBLICATIONS

Schlenk, Richard P., et al., "Biomechanics of Spinal Deformity"; Neurosurg Focus, 14(1): Article 2, Jan. 2003; vol. 14.
(Continued)

*Primary Examiner* — Pedro Philogene

(57) ABSTRACT

Systems and methods for a spinal surgical procedure are described. Specifically systems and methods for calculating global spinal alignment are described.

17 Claims, 60 Drawing Sheets

Related U.S. Application Data

(60) Provisional application No. 62/286,166, filed on Jan. 22, 2016.

(51) Int. Cl.

| | | |
|---|---|---|
| *A61B 18/18* | (2006.01) | |
| *A61B 6/00* | (2006.01) | |
| *A61B 90/00* | (2016.01) | |
| *A61B 5/00* | (2006.01) | |
| *A61B 5/107* | (2006.01) | |
| *A61B 34/10* | (2016.01) | |
| *A61B 34/00* | (2016.01) | |

(52) U.S. Cl.
CPC .............. *A61B 34/00* (2016.02); *A61B 34/10* (2016.02); *A61B 90/00* (2016.02); *A61B 90/361* (2016.02); *A61B 2034/101* (2016.02); *A61B 2034/104* (2016.02); *A61B 2090/067* (2016.02)

(56) References Cited

U.S. PATENT DOCUMENTS

| | | | |
|---|---|---|---|
| 7,957,831 B2 | 6/2011 | Isaacs | |
| 8,235,998 B2 | 8/2012 | Miller | |
| 8,442,621 B2 | 5/2013 | Gorek | |
| 8,744,826 B2 | 6/2014 | Skalli | |
| 8,753,346 B2 | 6/2014 | Suarez | |
| 8,831,324 B2 | 9/2014 | Penenberg | |
| 8,983,813 B2 | 3/2015 | Miles | |
| 8,992,542 B2 | 3/2015 | Hagag | |
| 9,119,670 B2 | 9/2015 | Yang | |
| 9,129,054 B2 | 9/2015 | Nawana | |
| 9,204,937 B2 | 12/2015 | Edelhauser | |
| 9,211,145 B2 | 12/2015 | Pereiro de Lamo | |
| 9,233,001 B2 | 1/2016 | Miles | |
| 9,248,002 B2 | 2/2016 | McCarthy | |
| 9,320,604 B2 | 4/2016 | Miles | |
| 9,408,698 B2 | 8/2016 | Miles | |
| 9,452,050 B2 | 9/2016 | Miles | |
| 9,572,682 B2 | 2/2017 | Aghazadeh | |
| 9,597,157 B2 | 3/2017 | Hagag | |
| 9,636,181 B2 * | 5/2017 | Isaacs | ..................... A61B 34/10 |
| 9,642,633 B2 * | 5/2017 | Frey | ..................... A61B 17/1757 |
| 9,662,228 B2 | 5/2017 | McCarthy | |
| 9,700,292 B2 | 7/2017 | Nawana | |
| 9,724,167 B2 | 8/2017 | Ziaei | |
| 2007/0073137 A1 | 3/2007 | Schoenefeld | |
| 2010/0191088 A1 * | 7/2010 | Anderson | .......... A61B 17/7074 |
| | | | 600/373 |
| 2012/0035507 A1 | 2/2012 | George | |
| 2013/0053854 A1 | 2/2013 | Schoenefeld | |
| 2013/0345757 A1 | 12/2013 | Stad | |
| 2014/0076883 A1 | 3/2014 | Brailovski | |
| 2014/0081659 A1 | 3/2014 | Nawana | |
| 2014/0378828 A1 | 12/2014 | Penenberg | |
| 2015/0073265 A1 | 3/2015 | Popovic | |
| 2015/0157416 A1 | 6/2015 | Andersson | |
| 2015/0227679 A1 | 8/2015 | Kamer | |
| 2015/0238271 A1 | 8/2015 | Wollowick | |
| 2015/0282796 A1 | 10/2015 | Nawana | |
| 2016/0022176 A1 | 1/2016 | Le Huec | |

FOREIGN PATENT DOCUMENTS

| | | | | |
|---|---|---|---|---|
| WO | WO-2013085982 | | 6/2013 | |
| WO | WO-2014016824 | | 1/2014 | |
| WO | WO-2014088801 | | 6/2014 | |
| WO | WO2015/003224 | * | 1/2015 | ............. A61B 90/06 |
| WO | WO-2015003224 | | 1/2015 | |
| WO | WO2015/195843 | * | 7/2015 | ............. A61B 90/06 |
| WO | WO-2018195843 | | 12/2015 | |

OTHER PUBLICATIONS

Smith, et al., "Clinical and Radiographic Evaluation of the Adult Spinal Deformity Patient"; Neurosurg Clin N An 24 (2), 143-156; Feb. 21, 2013.

Tanquay, et al., "Clinical and Radiographic Evaluation of the Adult Spinal Deformity Patient"; Neurosurg Clin N An 24 (2), 143-156; Feb. 21, 2013.

Ames, Christopher P., et al., "Reliability assessment of a novel cervical spine deformity classification system"; J Neurosurg Spine, Aug. 14, 2015.

Lehman, et al., "Do Intraoperative Radiographs in Scoliosis Surgery Reflect Radiographic Result?"; Clin Orthop Relat Res (2010) 468: 679-686.

* cited by examiner

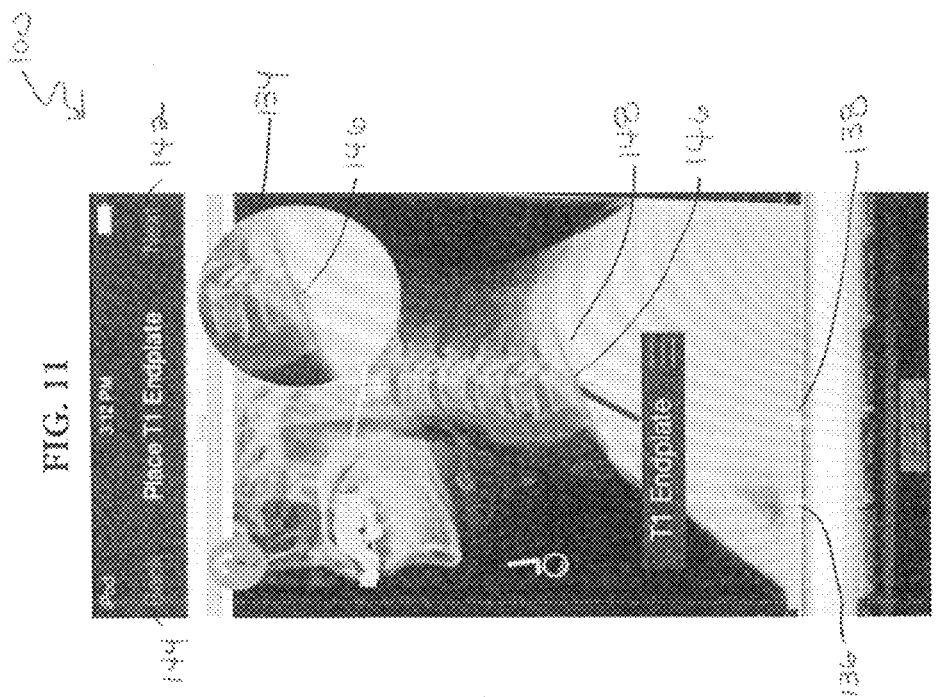
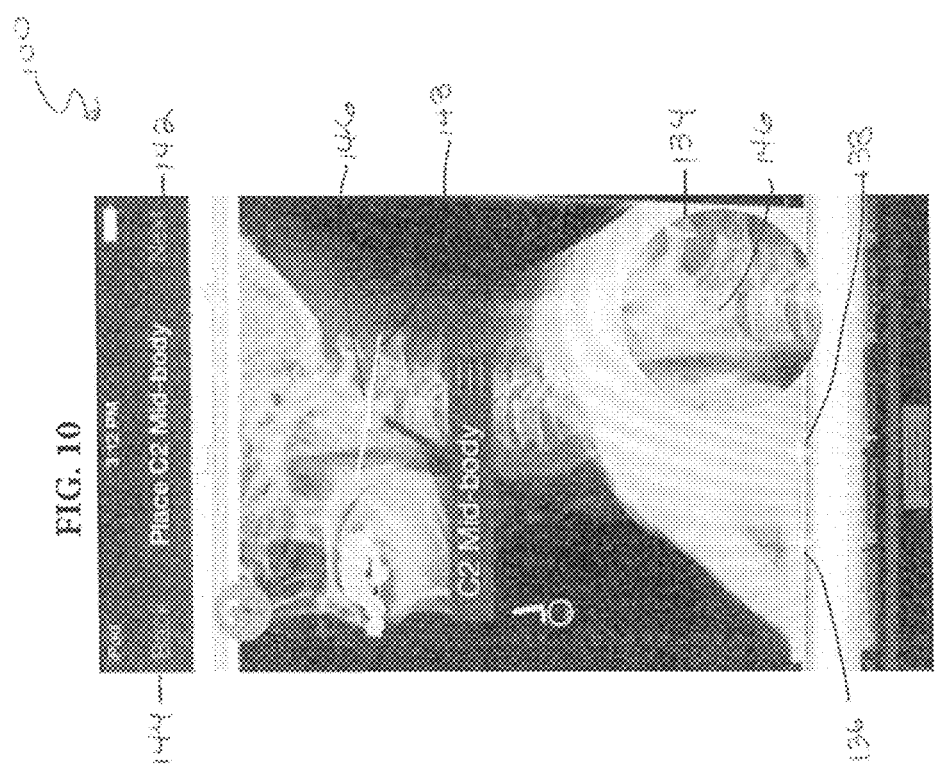

SYSTEMS AND METHODS FOR PERFORMING SPINE SURGERY

CROSS-REFERENCE TO RELATED APPLICATIONS

This patent application is a Continuation of International Pat. App. No. PCT/US17/14626, filed Jan. 23, 2017 (currently pending). International Pat. App. No. PCT/US17/14626 claims the priority of U.S. Provisional Application Ser. No. 62/286,166 filed on Jan. 22, 2016. Both of the foregoing related applications are incorporated herein by reference in their entireties.

FIELD

The present application pertains to spinal surgery. More particularly, the present application pertains to systems and methods related to the planning, performing, and assessing of surgical correction to the spine during a spinal procedure.

BACKGROUND

The spinal column is a highly complex system of bones and connective tissues that provide support for the body and protect the delicate spinal cord and nerves. The spinal column includes a series of vertebral bodies stacked atop one another, each vertebral body including an inner or central portion of relatively weak cancellous bone and an outer portion of relatively strong cortical bone. Situated between each vertebral body is an intervertebral disc that cushions and dampens compressive forces exerted upon the spinal column. A vertebral canal containing the spinal cord is located behind the vertebral bodies. The spine has a natural curvature (i.e., lordosis in the lumbar and cervical regions and kyphosis in the thoracic region) such that the endplates of the upper and lower vertebrae are inclined towards one another.

There are many types of spinal column disorders including scoliosis (abnormal lateral curvature of the spine), excess kyphosis (abnormal forward curvature of the spine), excess lordosis (abnormal backward curvature of the spine), spondylolisthesis (forward displacement of one vertebra over another), and other disorders caused by abnormalities, disease, or trauma (such as ruptured or slipped discs, degenerative disc disease, fractured vertebrae, and the like). Patients that suffer from such conditions often experience extreme and debilitating pain, as well as diminished nerve function. Posterior fixation for spinal fusions, decompression, deformity, and other reconstructions are performed to treat these patients. The aim of posterior fixation in lumbar, thoracic, and cervical procedures is to stabilize the spinal segments, correct multi-axis alignment, and aid in optimizing the long-term health of the spinal cord and nerves.

The definition and scope of spinal deformity, as well as treatment options, continue to evolve. Surgical objectives for spinal deformity correction include curvature correction, prevention of further deformity, the restoration of sagittal and coronal balance, cosmetic optimization, and improvement or preservation of neurological function. Sagittal plane alignment and pelvic parameters in cases of adult spinal deformity (ASD) are becoming increasingly recognized as correlative to health related quality of life scores (HRQOL). In the literature there are significant correlations between HRQOL scores and radiographic parameters such as Sagittal Vertical Axis (SVA), Pelvic Tilt (PT) and mismatch between pelvic incidence (PI) and lumbar lordosis (LL). Specific cervical parameters, including cervical lordosis (CL), cervical sagittal vertical axis (CSVA), T1 slope (TS), and the chin-brow vertical angle (CBVA), are significant indicators of the body's ability, or lack thereof, to align the head over the pelvis and maintain a horizontal gaze.

The SRS-Schwab classification of ASD was developed to assist surgeons with a way to categorize ASD, and provide methods of radiographic analysis. This classification system helps provide a protocol for pre-operative treatment planning and post-op assessment. The current environment to utilize this classification system requires surgeons to examine pre-operative patient films and measure pelvic incidence, lumbar lordosis, pelvic tilt, and sagittal vertical axis either manually or through the use of pre-operative software. After the procedure, the surgeon examines the post-operative films and measures the same parameters and how they changed as a result of the surgery. A need exists for systems and methods for assessing these and other spinal parameters intraoperatively and assessing changes to these intraoperative spinal parameters as a surgical procedure progresses towards a pre-operative plan.

Screws, hooks, and rods are devices used to stabilize the spine during a spinal fixation procedure. Such procedures often require the instrumentation of many bony elements. The devices, for example rods, can be extremely challenging to design and implant into the patient. Spinal rods are usually formed of stainless steel, titanium, cobalt chrome, or other similarly hard metal, and as such are difficult to bend without some sort of leverage-based bender. Moreover, a spinal rod needs to be oriented in six degrees of freedom to compensate for the anatomical structure of a patient's spine as well as the attachment points (screws, hooks) for securing the rod to the vertebrae. Additionally, the physiological problem being treated as well as the physician's preferences will determine the exact configuration necessary. Accordingly, the size, length, and particular bends of the spinal rod depends on the size, number, and position of each vertebrae to be constrained, the spatial relationship amongst vertebrae, as well as the screws and hooks used to hold the rods attached to the vertebrae.

The bending of a spinal rod can be accomplished by a number of methods. The most widely used method is a three-point bender called a French Bender. The French bender is a pliers-like device that is manually operated to place one or more bends in a rod. The French bender requires both handles to operate and provides leverage based on the length of the handle. The use of the French bender requires a high degree of physician skill because the determination of the location, angle, and rotation of bends is often subjective and can be difficult to correlate to a patient's anatomy. Other methods of bending a rod to fit a screw and/or hook construct include the use of an in-situ rod bender and a keyhole bender. However, all of these methods can be subjective, iterative, and are often referred to as an "art." As such, rod bending and reduction activities can be a time consuming and potentially frustrating step in the finalization of a complex and/or long spinal construct. Increased time in the operating room to achieve optimum bending can be costly to the patient and increase the chance of the morbidity. When rod bending is performed poorly, the rod can preload the construct and increase the chance of failure of the fixation system. The bending and re-bending involved can also promote metal fatigue and the creation of stress risers in the rod.

Efforts directed to computer-aided design or shaping of spinal rods have been largely unsuccessful due to the lack of bending devices as well as lack of understanding of all of the issues involved in bending surgical devices. Recently, in U.S. Pat. No. 7,957,831, issued Jun. 7, 2011 to Isaacs, there is described a rod bending system which includes a spatial measurement sub-system with a digitizer to obtain the three dimensional location of surgical implants (screws, hooks), software to convert the implant locations to a series of bend instructions, and a mechanical rod bender used to execute the bend instructions such that the rod will be bent precisely to custom fit within each of the screws. This is advantageous because it provides quantifiable rod bending steps that are customized to each patient's anatomy enabling surgeons to create custom-fit rods on the first pass, thereby increasing the speed and efficiency of rod bending, particularly in complex cases. This, in turn, reduces the morbidity and cost associated with such procedures. However, a need still exists for improved rod bending systems that allow for curvature and deformity correction in fixation procedures, provide the User with more rod bending options, and accommodate more of the User's clinical preferences. Furthermore, a need exists for improved rod bending systems that ensure proper sagittal and coronal alignment of the spine so that patients' HRQOL can be enhanced over standard methods.

SUMMARY

The needs above, as well as others, are addressed by embodiments of a system and method for displaying near-real time intraoperative images of surgical tools in a surgical field described in this disclosure.

A system is disclosed for global alignment of a spine during spine surgery, where the system includes an imaging device, a spatial tracking system, a control unit, and a bending device.

A system is disclosed for global alignment of a spine during spine surgery, where the system includes an imaging device, a rod bending device, and a control unit with software to enable entry of spinal parameter measurements from preoperative images, surgical planning, and intraoperative images, and generating instructions for bending a rod. The anatomical parameter may be chin brow vertical angle. The parameter may be related to the patient's gaze. The parameter may be related to the patient's quality of life score. The system may further provide visual indicators regarding the measured parameters.

A method is disclosed for global alignment of a spine during spine surgery, wherein the method includes inputting surgical plan parameters into a control unit, taking intraoperative measurements of the parameters, comparing the intraoperative measurements to the surgical plan, measuring the location of the bone screws, calculating rod bending instructions, and bending the rod according to the instructions. The parameter may be chin brow vertical angle. The parameter may be related to the patient's gaze. The parameter may be related to the patient's quality of life score.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 10 is a screen shot illustrating an example of a measurement screen according to the embodiment of FIG. 2 to allow the user to identify the midbody of C2;

FIG. 11 is a screen shot illustrating an example of a measurement screen according to the embodiment of FIG. 2 to allow the user to identify the T1 endplate;

FIGS. 24-26 are screen shots illustrating an example measurement of cervical lordosis according to the embodiment of FIG. 15.

FIGS. 58-59 are screen shots illustrating an example rod lordosis correction screen according to one embodiment;

DETAILED DESCRIPTION

Illustrative embodiments of the invention are described below. In the interest of clarity, not all features of an actual implementation are described in this specification. It will of course be appreciated that in development of any such actual embodiment, numerous implantation-specific decisions must be made to achieve the developers' specific goals such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems and methods disclosed herein boast a variety of inventive features and components that warrant patent protection, both individually and in combination.

Figure 1:
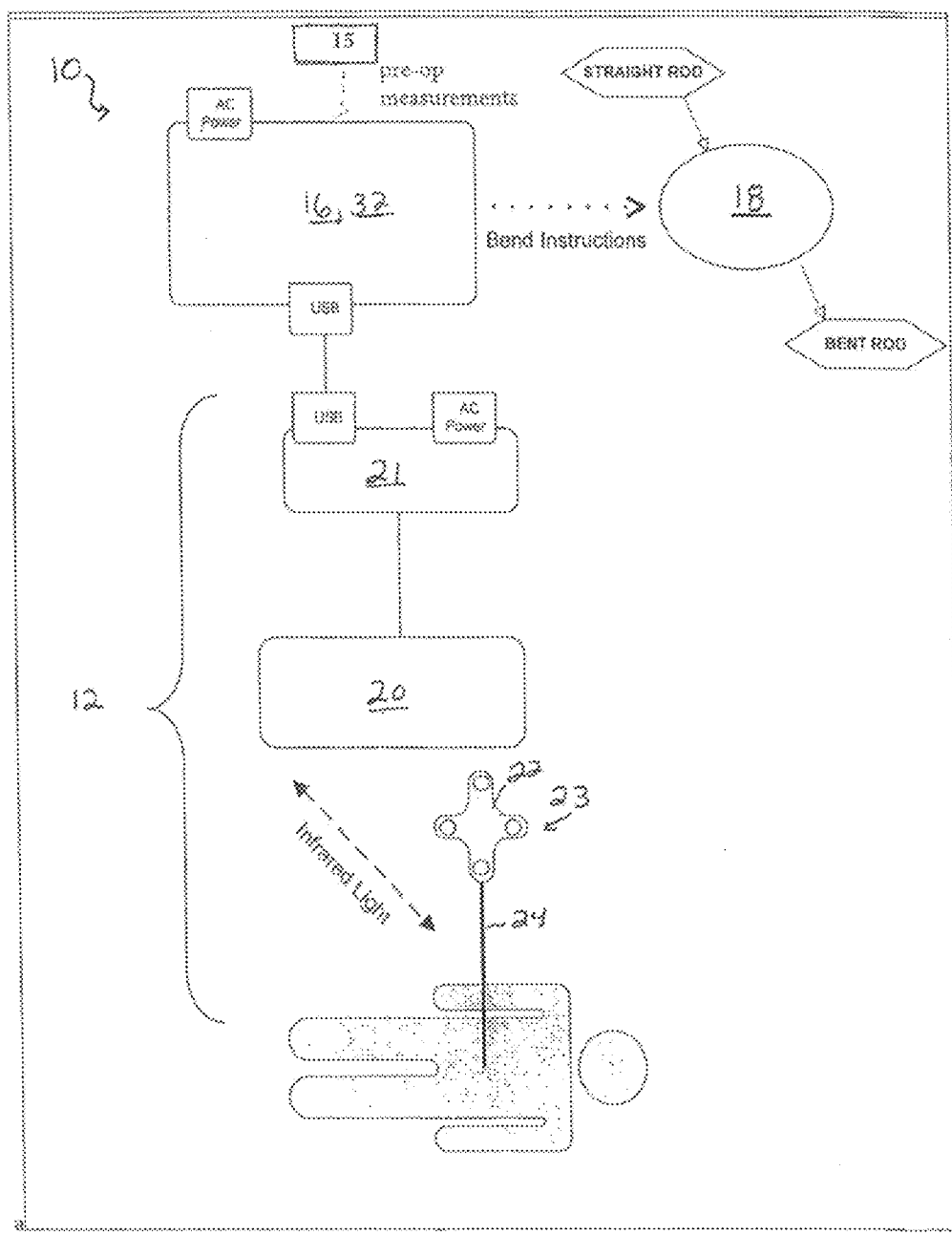
FIG. 1 is a diagram of a system for measuring spinal parameters according to one embodiment.
Figure 3:
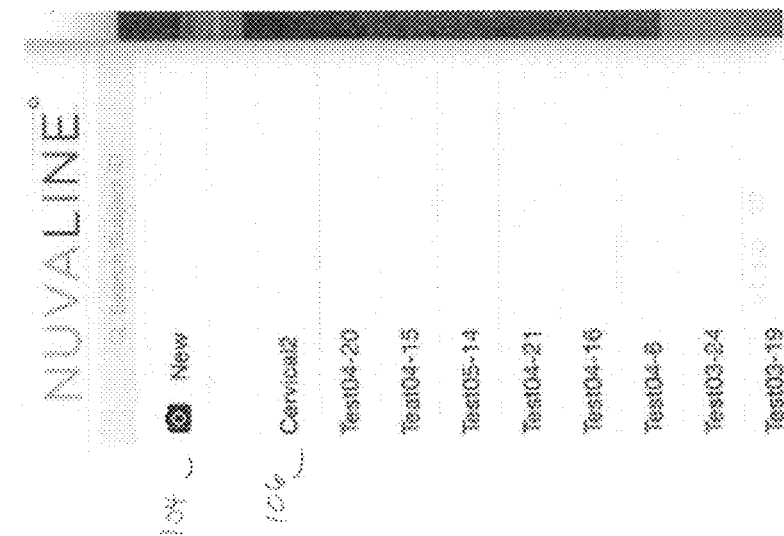
FIG. 3 is a screen shot illustrating an example of the a setup screen according to the embodiment of FIG. 2 to allow the user to capture a new image or open a saved image.

Implants placed at one level of the spine to correct a spinal deformity may affect clinical parameters not only at that site, but also other sites throughout the spinal column. For example, correction of lumbar lordosis may result in a change in cervical lordosis. In some spinal procedures (e.g., anterior column deformity correction procedures), restoring a patient's spine to a balanced position may be a desired surgical outcome. According to a broad aspect of the invention, as shown in FIG. 1 by way of example, one embodiment of a surgical planning, assessment, and correction system 10 may include a spatial tracking system 12 to obtain the location of one or more surgical implants 14, a control unit 16 containing software convert spinal parameters and implant locations to a series of bend instructions, a bending device 18 to execute the bend instructions, a c-arm fluoroscope for imaging, 20. In some embodiments, the system may also comprise a hand-held mobile communication device 15 with application software for making preoperative measurements.

The system 10 may include a Global Spinal Balance feature in which the control unit 16 is configured to receive and assess 1) preoperative spinal parameter measurements; 2) target spinal parameter inputs; 3) intraoperative spinal parameter inputs; and 4) postoperative spinal parameter inputs. One or more of these inputs may be tracked and/or compared against other inputs to assess how the surgical correction is progressing toward a surgical plan, assess how close the patient's spine is to achieving global spinal balance, and utilized to develop/refine an operative plan to achieve the desired surgical correction.

The target spinal parameter measurements may be a clinical guideline (by way of example only, the SRS-Schwab classification, or a patient-specific goal based on that patient's anatomy). Depending on User preference, these spinal parameters may comprise Pelvic Incidence (PI), Pelvic Tilt (PT), Sacral Slope (SS), Lumbar Lordosis (LL), Superior Lumbar Lordosis (↑LL), Inferior Lumbar Lordosis (↓LL) Plumb Line offset (C7PL), and Thoracic Kyphosis (TK), T1 slope (TS), Sagittal Vertical Axis (SVA), cervical lordosis (CL), cervical sagittal vertical axis (CSVA), and chin-brow vertical angle (CBVA) measurements.

Preoperative Measurement

According to the exemplary embodiment shown in FIGS. 2-13, preoperative measurement of spinal parameters may be made using a hand held mobile device with a camera and a touch screen such as, for example, a mobile phone or a tablet with a software application that includes the measurement features described below. One such appropriate application is Nuvaline®. However any application capable of performing the image manipulation and measurements described herein may be used.

Figure 2:
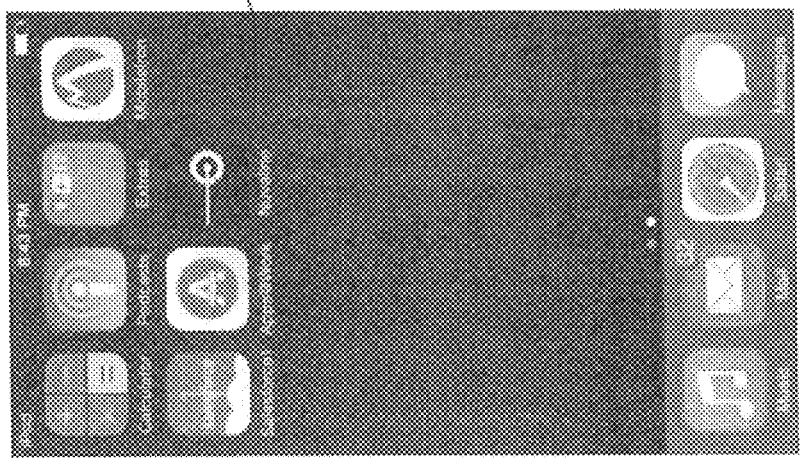
FIG. 2 is a screen shot illustrating an example of a mobile device with application software for preoperative measurements according to one embodiment.
Figure 5:
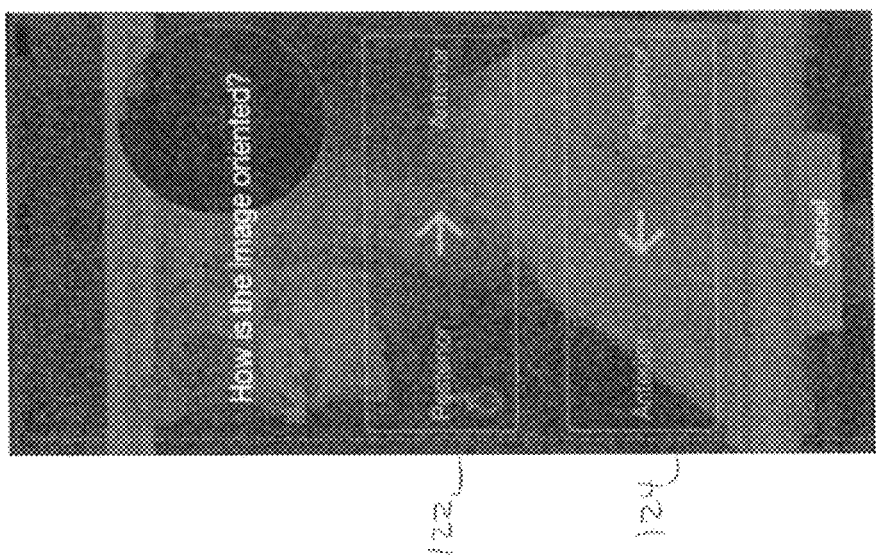
FIG. 5 is a screen shot illustrating an example of the a setup screen according to the embodiment of FIG. 2 to allow the user to identify the orientation of the image.
Figure 4:
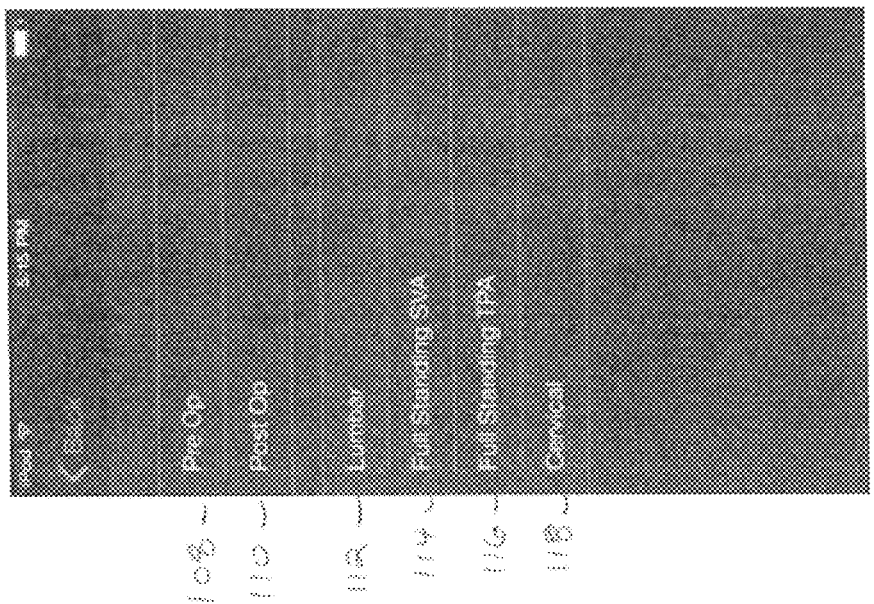
FIG. 4 is a screen shot illustrating an example of the a setup screen according to the embodiment of FIG. 2 to allow the user to specify the image type.
Figure 7:
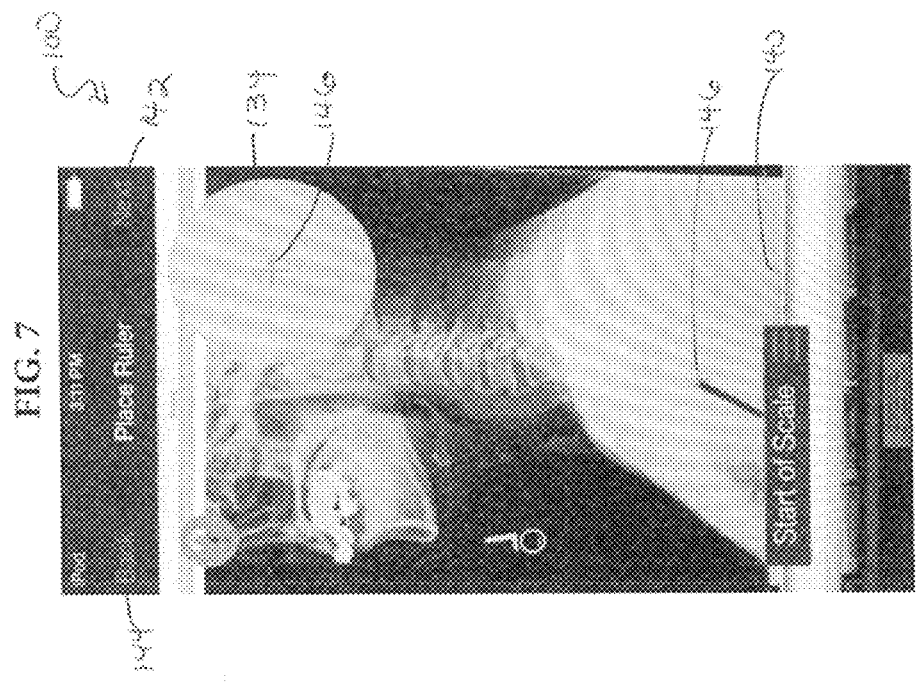
FIG. 7 is a screen shot illustrating an example of the a setup screen according to the embodiment of FIG. 2 to allow the user to set the scale to the image.
Figure 6:
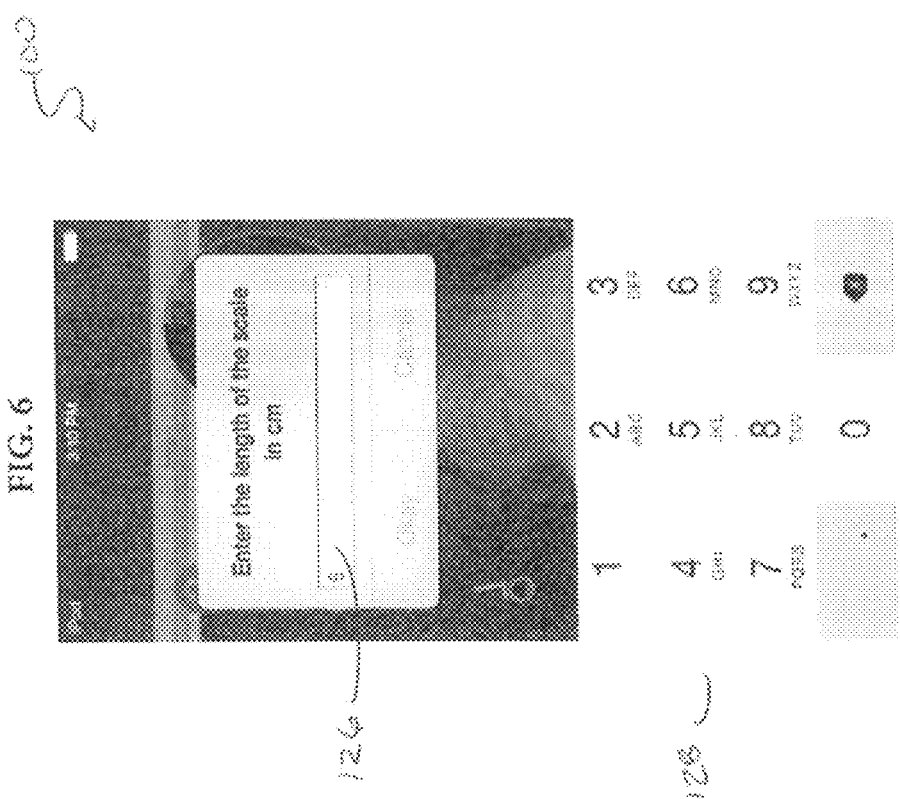
FIG. 6 is a screen shot illustrating an example of the a setup screen according to the embodiment of FIG. 2 to allow the user to enter the scale size.
Figure 8:
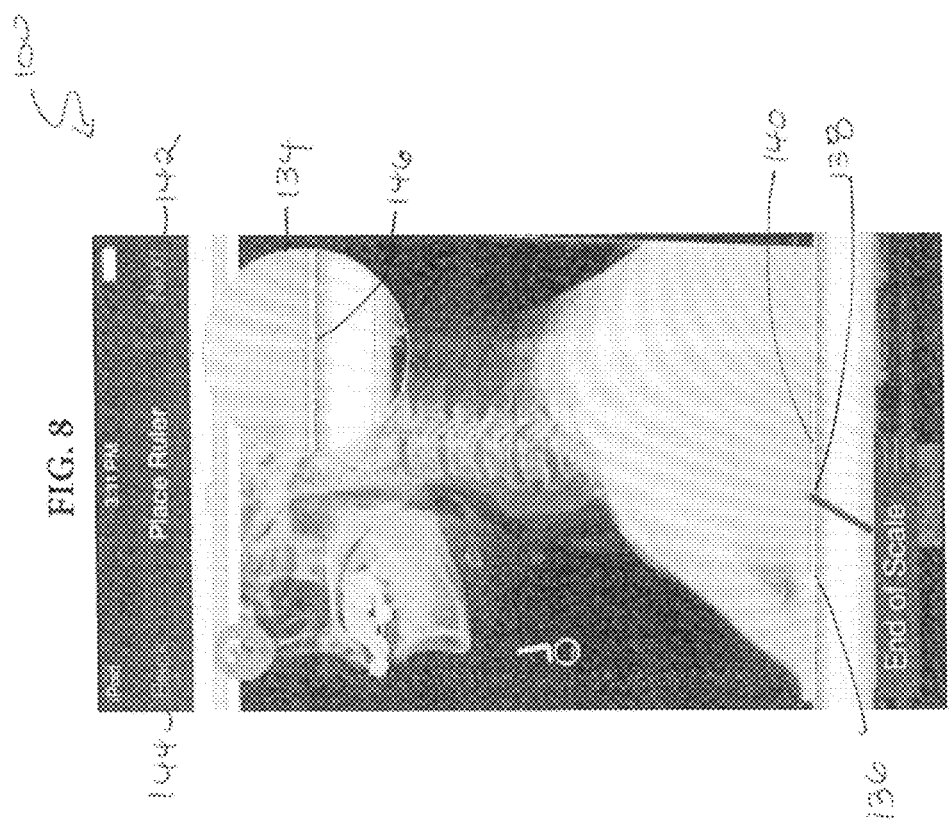
FIG. 8 is a screen shot illustrating an example of the a setup screen according to the embodiment of FIG. 2 to allow the user to set the scale to the image.
Figure 13:
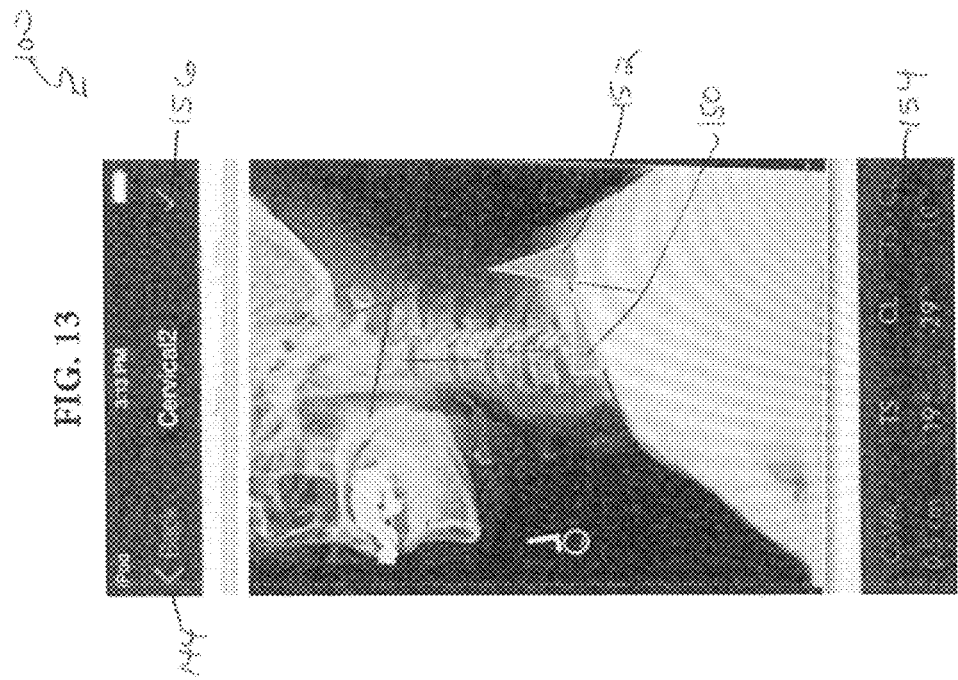
FIG. 13 is a screen shot illustrating an example of a measurement screen according to the embodiment of FIG. 2 displaying the calculated parameters.

As shown in FIG. 2, in one embodiment, the User initiates the application by selecting the application icon 102 from the touchscreen of the mobile device. From the list screen, as shown for example in FIG. 3, the User may choose to capture a new image by selecting the New button 104, or may view previously captured images and measurements by selecting a previously saved file 106. If the User selects the New button 104, a new image may be captured from a display using the camera feature of the mobile device 15. As shown in FIGS. 4-8, before measurements can be taken, the User must identify the type and orientation of the image, and provide scale information. The User may classify the type of image by selecting the appropriate settings as shown in FIG. 4. If performing preoperative measurements of a cervical image, the User may select the Pre Op 108 and Cervical 118 options from the setup screen. The User then identifies the orientation of the image by selecting the correct orientation button 122, 124 as shown in FIG. 5. The length of the measurement calibration scale is entered into the scale field 126 using the keypad 128 as shown in FIG. 6. In this example, the scale is set to 5 cm. The User may then correlate the scale to the imported image by selecting the correct measurement interval on the screen. As shown in FIGS. 7-8, to mark the Start of Scale 136 a crosshair indicator 146 is placed over the scale 140 located at the bottom of the image, the crosshair indicator 146 may be dragged to the correct position by the User's finger. The User then marks the End of Scale 138 by dragging a second crosshair indicator 146 to the appropriate endpoint of the scale on the image 140. In the example shown in FIG. 8, the 5 cm scale has been correlated to the image by choosing points 5 cm apart on the image scale 140. When the User selects the Next button 142, the measurement application begins a workflow of measurement instructions.

Figure 9:
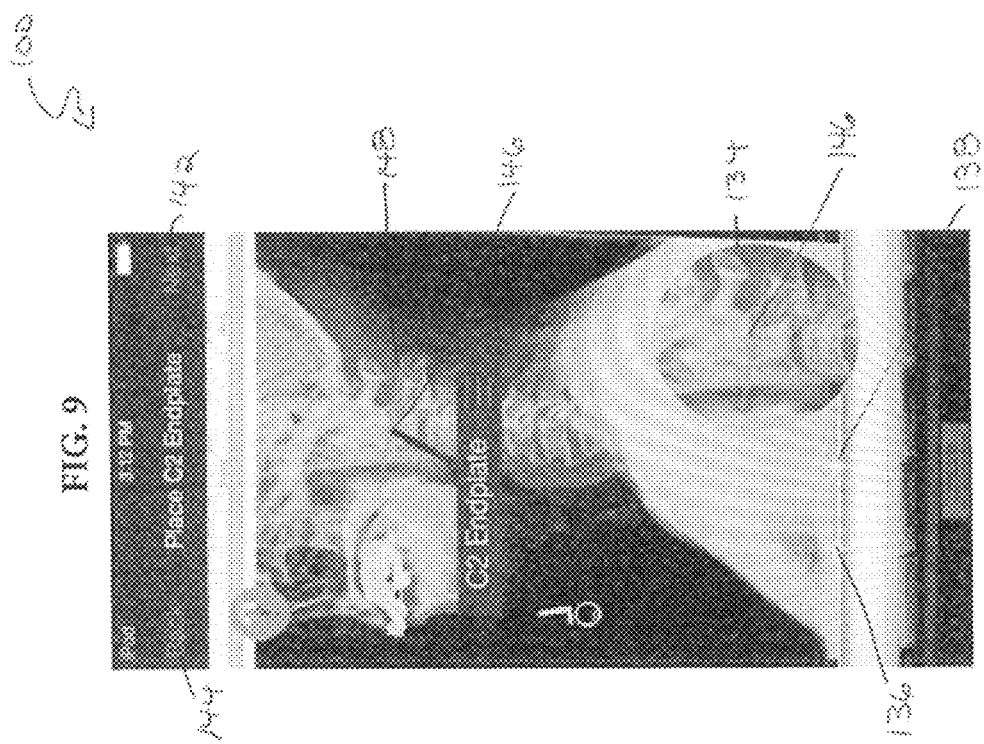
FIG. 9 is a screen shot illustrating an example of a measurement screen according to the embodiment of FIG. 2 to allow the user to identify the C2 endplate.

As shown in FIG. 9, the User may first mark the location of the C2 endplate. Using the bubble with the zoom perspective 134, the User may drag the crosshairs 146 to a position at the top center of the superior endplate of C2. Using two fingers, the User may adjust the orientation of the line 148 until it is superimposed over the slope of the C2 endplate. The User may press the Next button 142 to advance to the next measurement screen.

As shown in FIG. 10, the User may next mark the location of the C2 mid-body. Using the bubble with the zoom perspective 134, the User may drag the crosshairs 146 to a position on the center of the mid-body of the C2 vertebral body. The User may press the Next button 142 to advance to the next measurement screen.

The User may then mark the T1 endplate as shown in FIG. 11. Using the bubble with the zoom perspective 134, the User may drag the crosshairs 146 to a position at the center of the superior endplate of T1. Using two fingers on the touchscreen of the handheld device, the User may rotate the line 148 until it is superimposed over the slope of the T1 endplate. The User may press the Next button 142 to advance to the next measurement screen.

Figure 12:
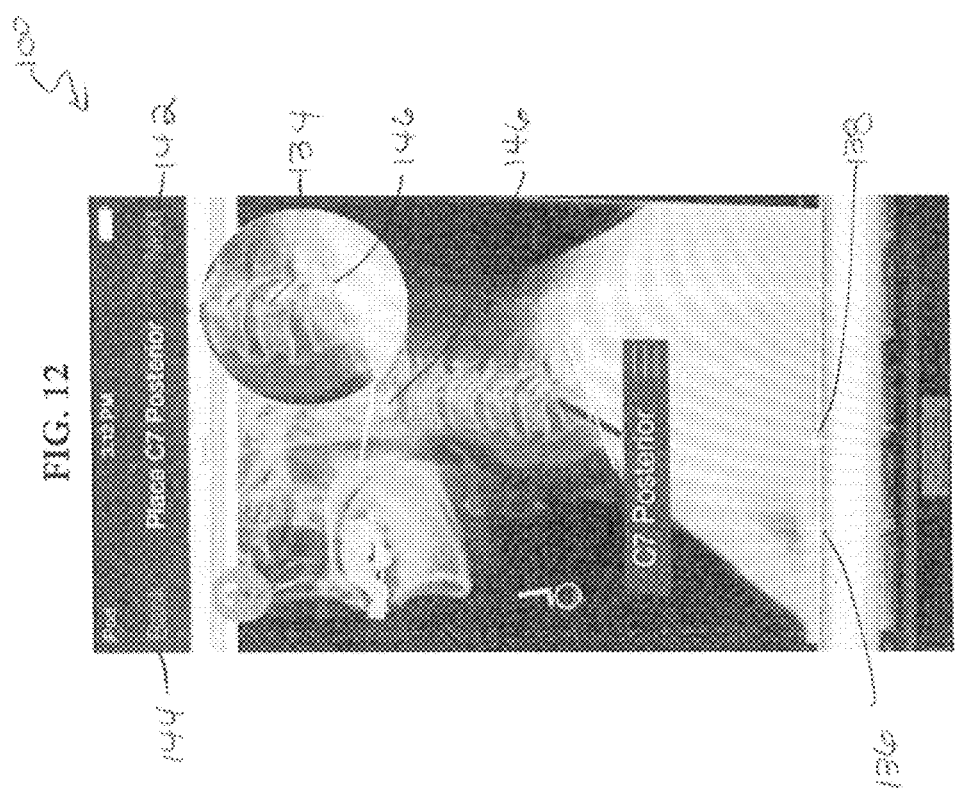
FIG. 12 is a screen shot illustrating an example of a measurement screen according to the embodiment of FIG. 2 to allow the user to identify the posterior point of C7.

As shown in FIG. 12, the User may mark the posterior of the C7 vertebra in the same manner as the other points. Using the bubble with the zoom perspective 134, the User may drag the crosshairs 146 to a position on the posterior corner of the C7 endplate. The User may press the Next button 142 to advance to the next measurement screen.

When the spinal markers have been identified, the cervical parameters may be calculated based upon the locations. The cervical parameters calculated from the measurements described above may include TS, CL, TS-CL, and CSVA. In some embodiments, the image may be superimposed with lines and angles to provide a graphic rendering of the spinal parameters. For example, in the image shown in FIG. 13, a wedge shape indicating, TS 150 and a wedge shape indicating CL 152 graphically represent those measurements on the image. The numeric values of the measurements may be shown in a display area 154 below the image.

In some embodiments, the numeric data may be color-coded to provide an indication of the degree of pathology. The value of TS-CL may be displayed, for example, in a Green color when the value is non-pathologic (TS-CL<+/−15 degrees), in a Yellow color when the value indicates there is a potential moderate deformity (+/−15≤TS≤+/−20 degrees), and in a Red color when the value indicates there is a potential for a marked deformity (TS-CL≥+/−20 degrees). Similarly, the value of CSVA may be displayed, for example, in a Green color when the value is non-pathologic (CSVA<+/−4 cm), in a Yellow color when the value indicates there is a potential moderate deformity (+/−4 cm≤CSVA≤+/−8 cm), and in a Red color when the value indicates there is a potential for a marked deformity (CSVA≥+/−8 cm).

When all measurements have been completed, the User may close the image by selecting the Check button 156.

It will be appreciated that the embodiment shown in FIGS. 2-13 is merely exemplary and the methods may be equally applied to other measurements. It will be appreciated that measurements of chin and brow for calculation of CBVA may be taken using methods similar to those disclosed. It will be appreciated that measurements and calculations related to thoracolumbar spinal parameters may be made using methods similar to those disclosed. It will be appreciated that the workflow of measurements described in this exemplary embodiment may be performed in a different order. Such modifications may be made without departing from the scope of the invention and are within the knowledge of a person of ordinary skill in the art.

Intraoperative Measurement and Global Alignment

In various embodiments, the systems and methods herein measure cervical parameters and assess both sagittal and coronal balance intraoperatively, thereby enabling the conversion and transformation of the assessment into User actions on the patient. In some embodiments, the systems and methods herein assess the sagittal alignment intraoperatively. One example embodiment is described below.

In one exemplary embodiment, intraoperative measurement of cervical spinal parameters may comprise the following steps, each of which us described more fully below: CL may be calculated by acquiring images at C2 and C7, scaling and orienting the images, and identifying the end plates of the C2 and C7 vertebra. TS may be calculated by identifying a horizontal line along a reticle, and identifying the endplate of T1. The TS-CL value may be calculated from CL and TS by arithmetic function. CSVA may be calculated by identifying a horizontal line along a reticle, locating the posterior corner of C7, and locating the mid-body position of C2. Finally, CBVA may be calculated by identifying a vertical line, and locating a point along the brow and chin.

Figure 14:
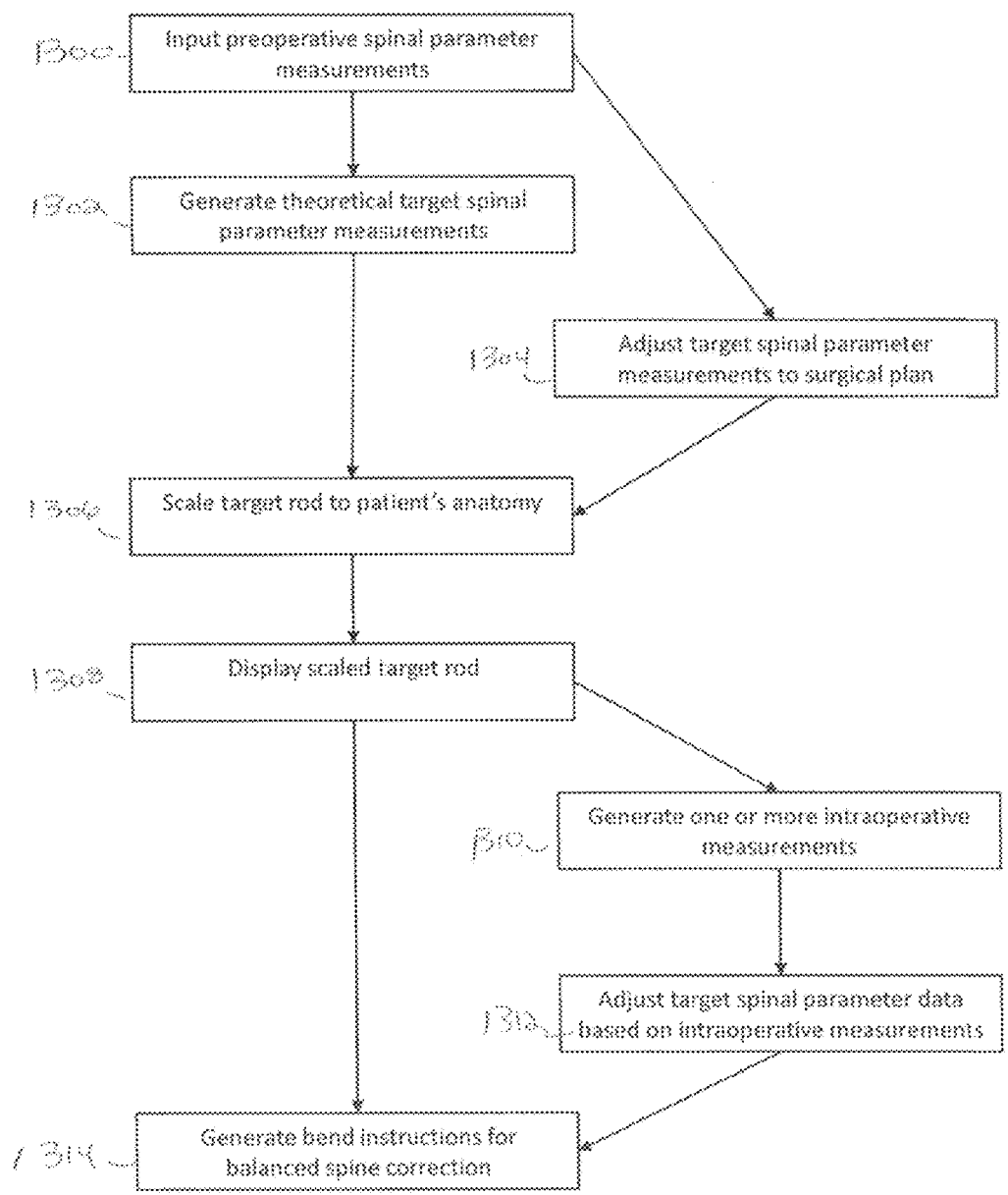
FIG. 14 is a flowchart of an integrated alignment according to one embodiment.

FIG. 14 depicts a flowchart indicating the steps of the Global Spinal Balance feature according to one embodiment. At step 1300 the system 10 inputs a patient's preoperative spinal parameter measurements. Then, the system 10 generates theoretical target spinal parameter measurements (step 1302). One or more target spinal parameter measurements may be optionally adjusted the User in accordance with a surgical plan a step 1304. At step 1306, a target spinal rod may be scaled to match the patient's anatomy using the theoretical or adjusted target spinal parameter measurements from step 1302 or 304. This scaled target rod may then be displayed 1308 to the User. Optionally, the system 10 may generate one or more measurements (step 1310) during the surgical procedure. At step 1312, the target spinal parameter data may then be adjusted based on the intraoperative measurements from step 310. Finally, the system 10 may generate bend instructions for balanced spine correction step 1314.

Figure 15:
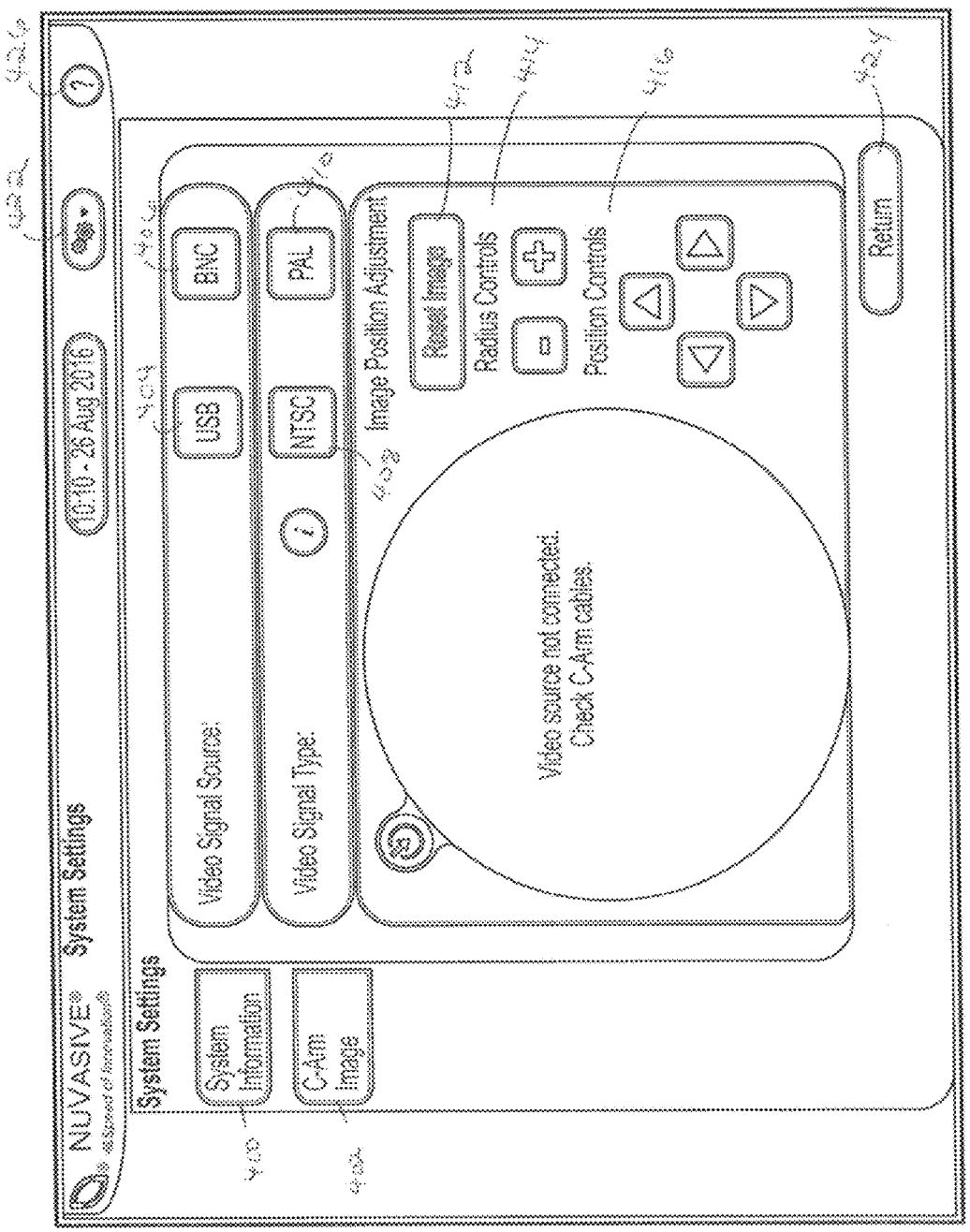
FIG. 15 is a screen shot illustrating an example of a setup screen according to one embodiment.
Figure 16:
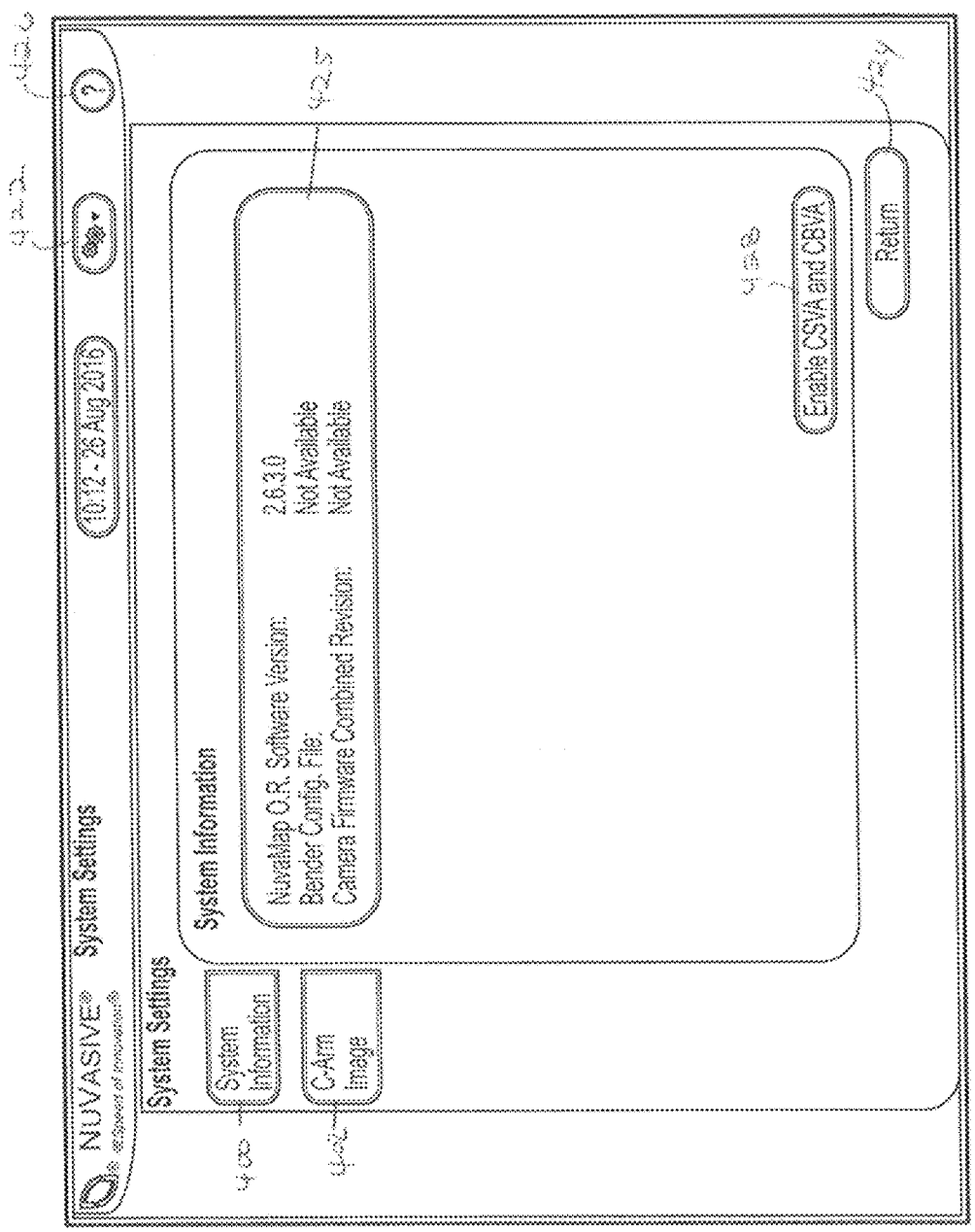
FIG. 16 is a screen shot illustrating an example of system parameter settings according to the embodiment of FIG. 15.

According to the exemplary embodiment shown in FIG. 15, to begin the intraoperative analysis, the User may initiate the system 10, and identify a video signal source 404, 406 and video signal type 408, 410. An image may be imported by selecting the import button 418. The image 575 displayed in window 420 may be repositioned using the radius controls 414 to enlarge or shrink the image to fit the window 420. The position of the image 575 may be changed by use of a directional arrow keypad 416. The manipulated image may be reset to its original setting by selecting the Reset Image button 412. The user may access a tool menu by selecting the tool button 422, or may select the "?" button 426 to access a help menu. As shown in FIG. 16, system settings may be reviewed by selecting the system information screen 400. From this screen a user may enable the optional CSVA and CBVA measurements by selecting the Enable button 428. The user selects the Return button 424 to return to the setup menu.

Figure 17:
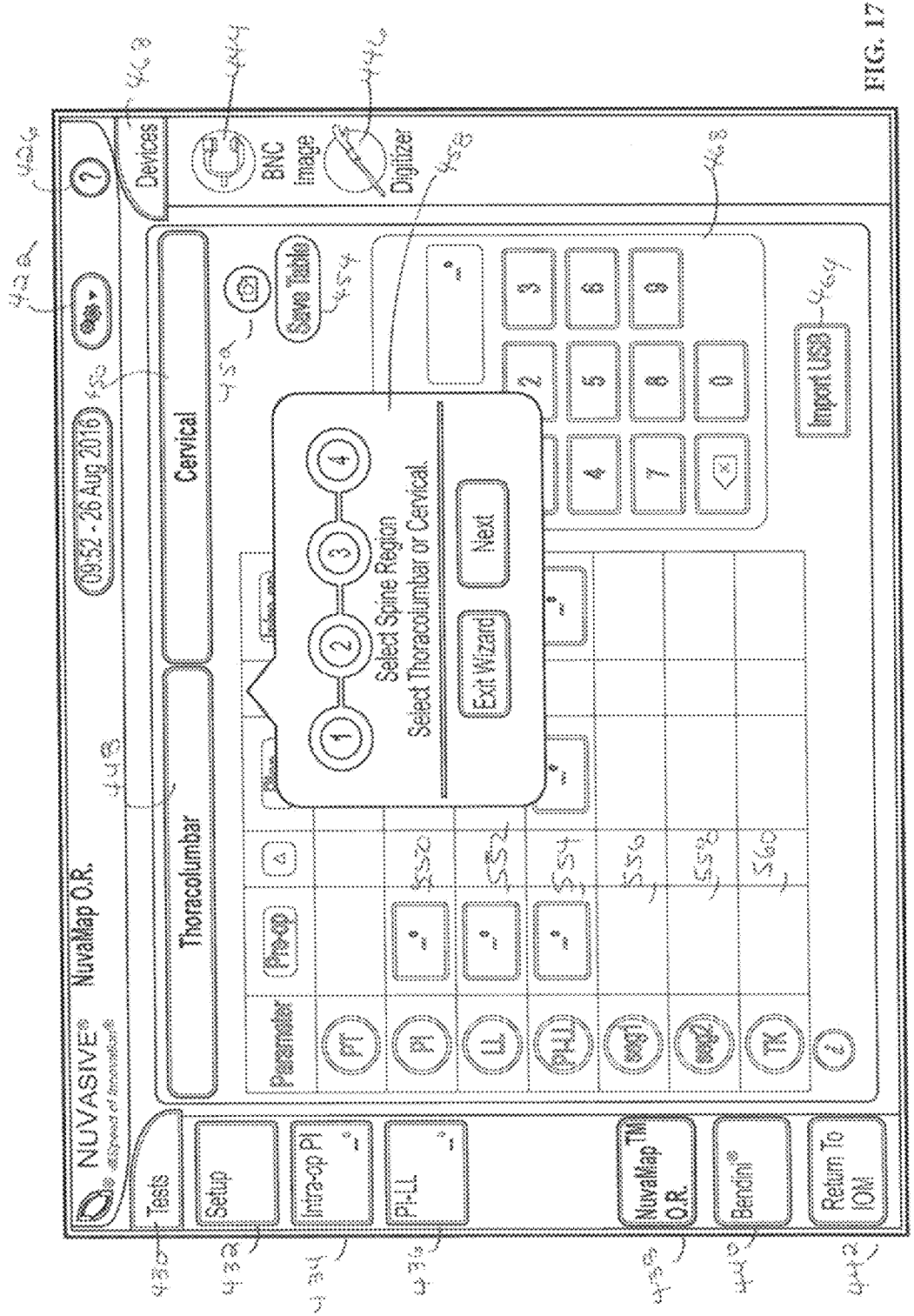
FIG. 17 is a screen shot illustrating an example of a measurement input setup screen according to the embodiment of FIG. 15.

The User may input a patient's preoperative measurements into the system 10 as depicted, by way of example in FIG. 17. The User may select the Setup button 432 to access the available parameters. As shown, the User may be directed through the process of entering the preoperative data by a setup tool 458. Selecting the Thoracolumbar button 448 may allow the User to input measurements relevant to thoracolumbar parameters for PI, LL, PI-LL, Seg 1, Seg 2, and TK in fields 550, 552, 554, 556, 558, and 560, respectively. Selecting the Cervical button 450 may allow the User to input measurements relevant to cervical parameters into CL, ΔCL, TS, CSVA, and CBVA input fields (not shown). Preoperative measurements saved to a USB drive may be uploaded to populate the preoperative parameters by selecting the Import USB button 464. The pre-operative measurements may be obtained from use of the preoperative measurement software described above, or may be calculated within the intraoperative global alignment software as described below. The pre-operative anatomical measurements may be used to understand the imbalance in the patient's deformed spine as well as help determine an operative plan to implant devices that would adjust or form the spine to a more natural balance (e.g., rods, screws, a hyperlordotic intervertebral implant, etc.). Planning software allows the User to establish a surgical plan to correct a spinal deformity. The User may enter the target parameters sought to be achieved through the surgical procedure into the software in the same manner as entry of the preoperative values.

In accordance with the Global Spinal Balance feature, spinal parameter inputs may be assessed intraoperatively. For example, the User may wish to intraoperatively measure the amount of cervical lordosis that has been achieved (for example, after placement of an intervertebral implant). The intraoperative parameter measurements may be compared to the pre-operative values and the plan to determine if the surgery is having the effect of restoring global alignment to the patient. As described below, the system 10 may be configured to obtain or import one or more lateral images, generate one or more lines between two or more landmarks on the patient's anatomy, determine a relationship between those landmarks, and adjust one or more spinal parameters to be used in generating the rod solution.

Figure 18:
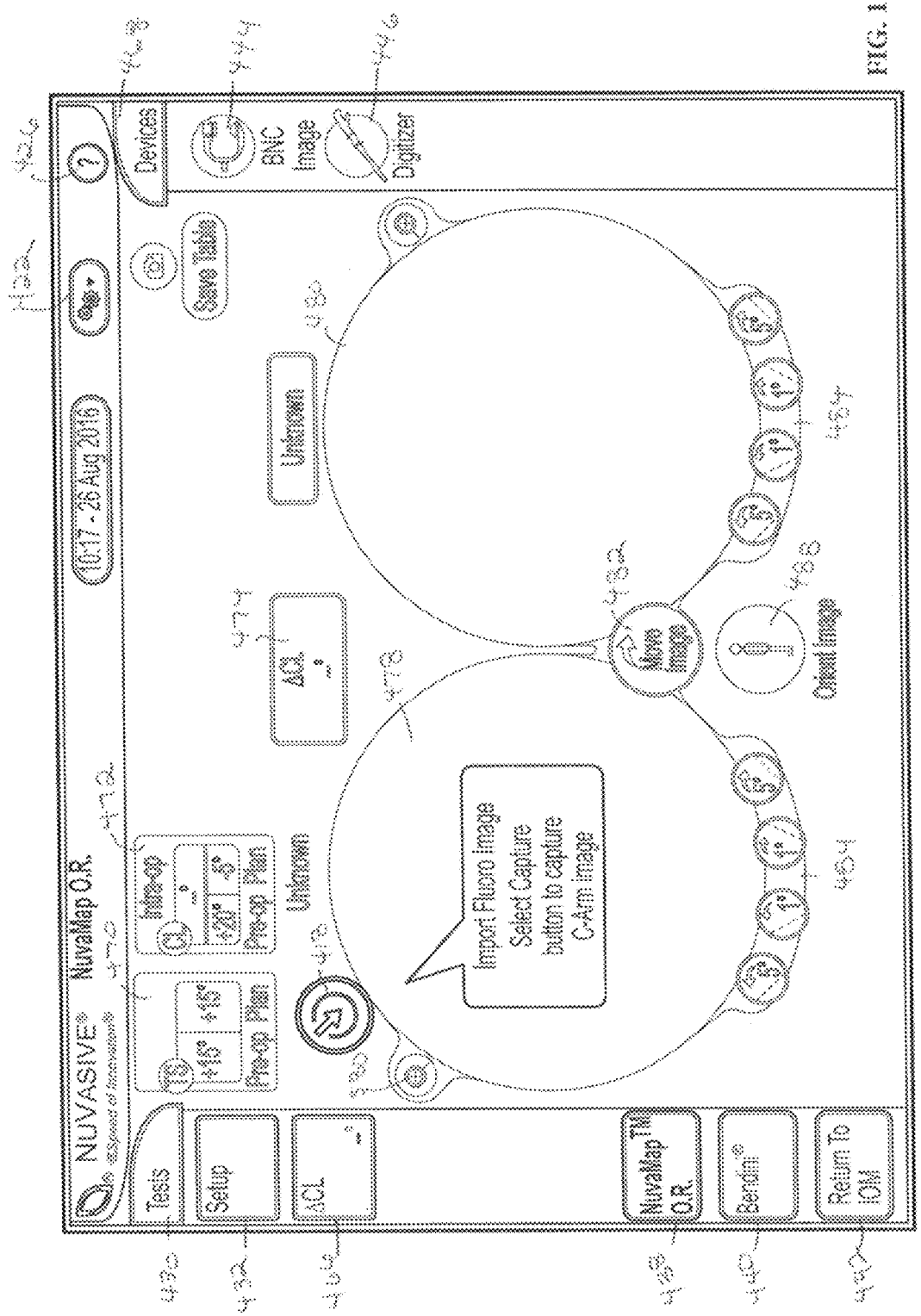
FIG. 18 is a screen shot illustrating an example of an image capture screen according to the embodiment of FIG. 15.
Figure 19:
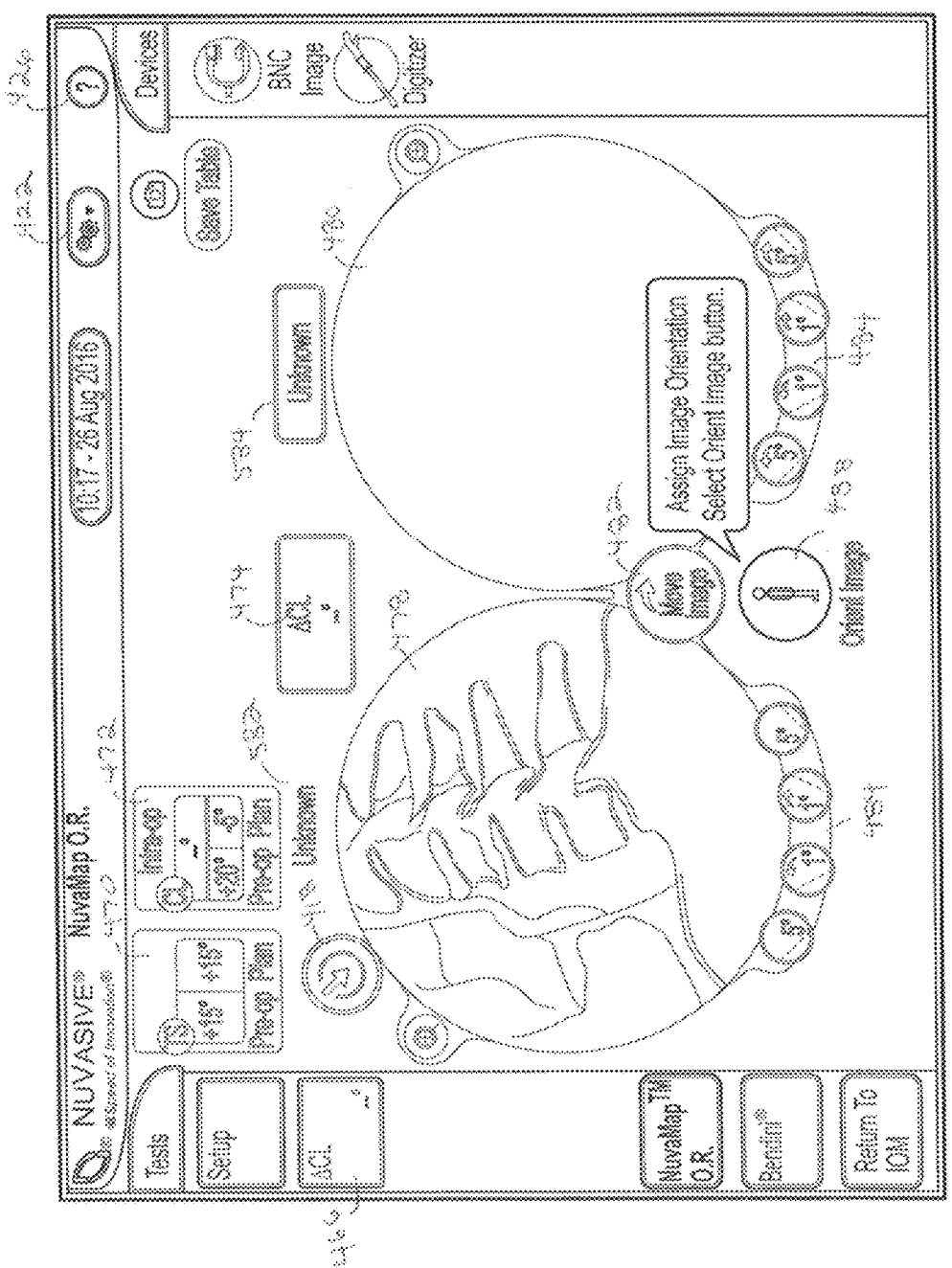
FIG. 19 is a screen shot illustrating an example of an image imported into the system according to the embodiment of FIG. 15.
Figure 20:
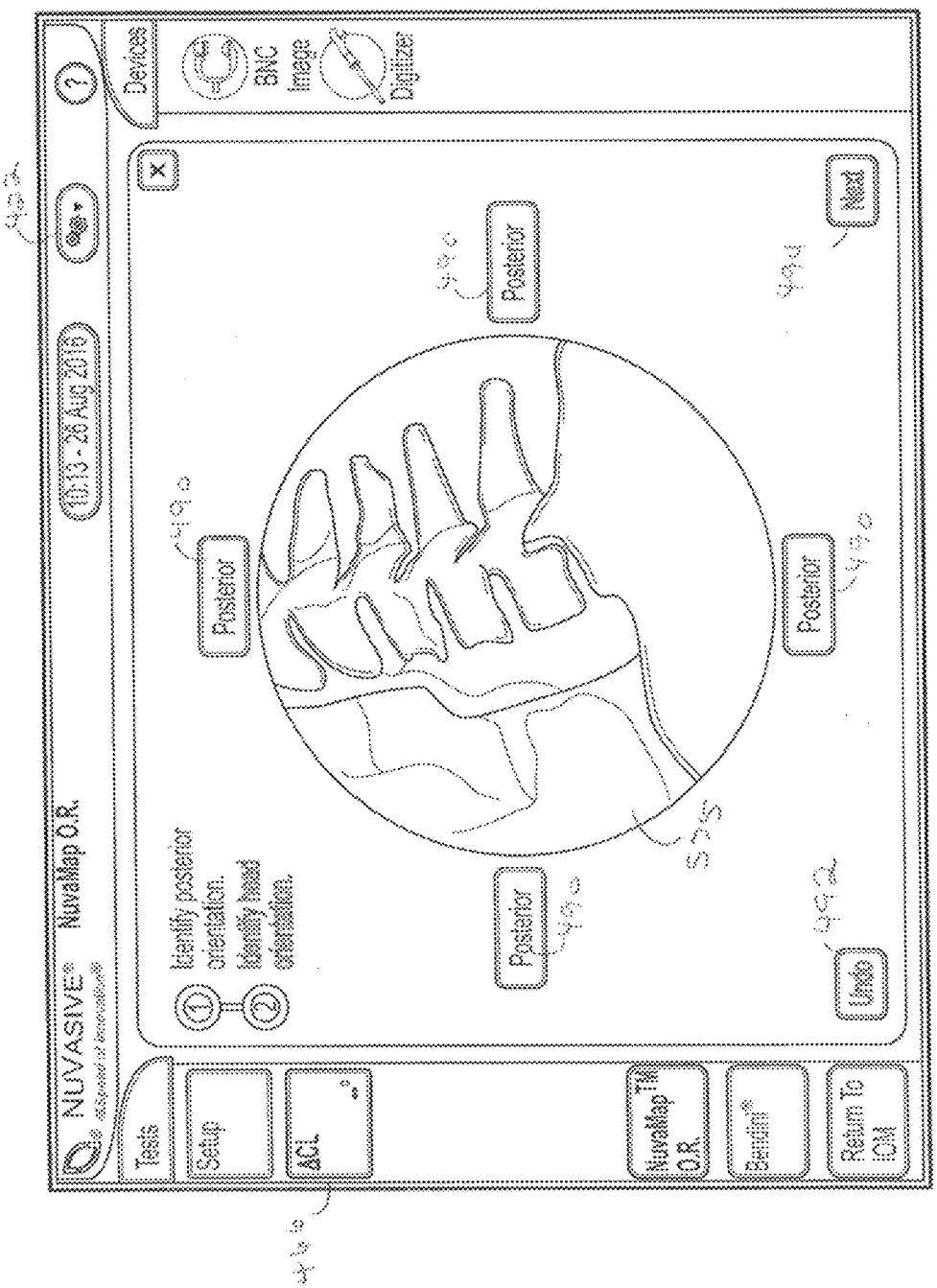
FIGS. 20-21 are screen shots illustrating an example of orientation of the figure according to the embodiment of FIG. 15.
Figure 21:
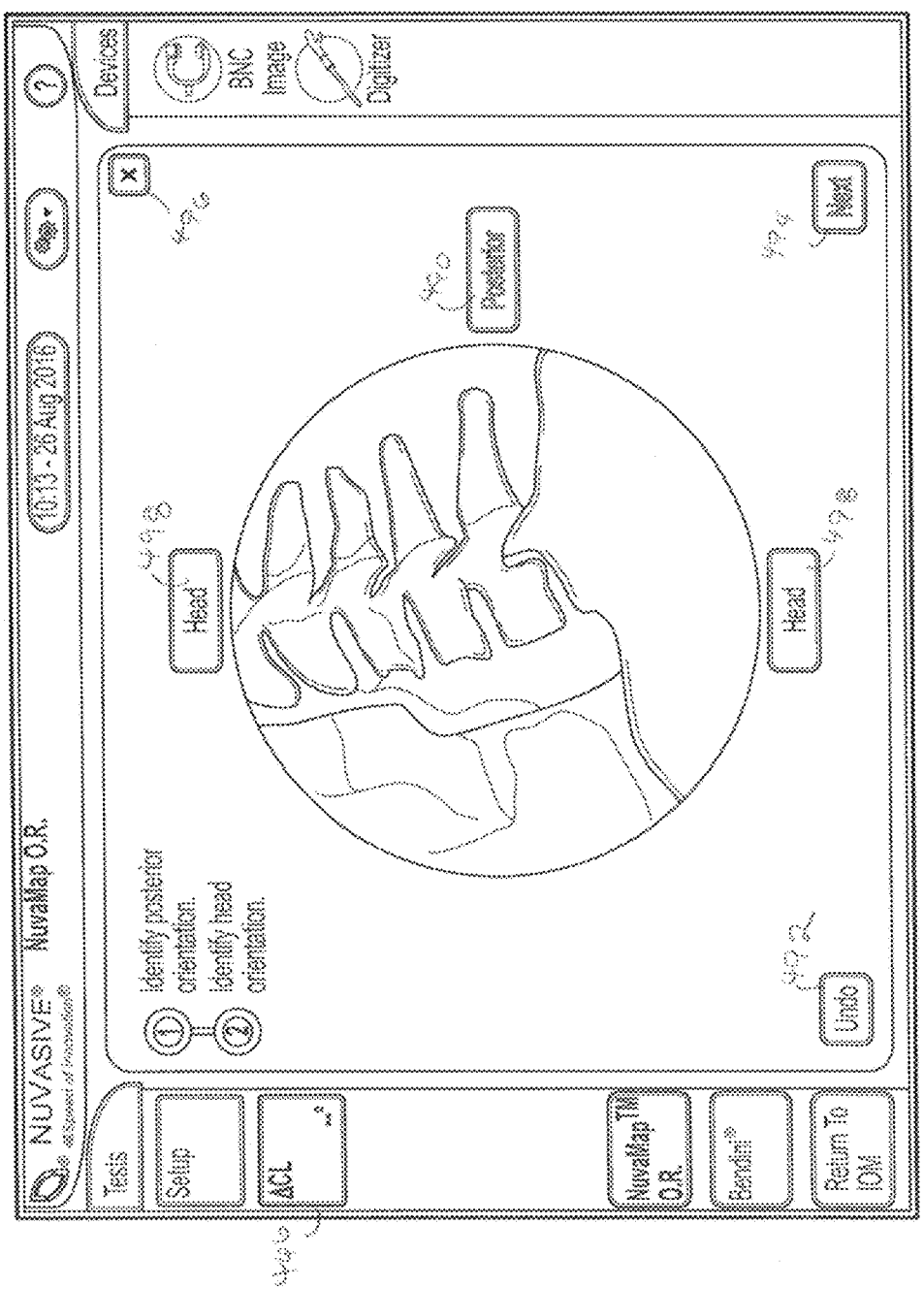
Figure 22:
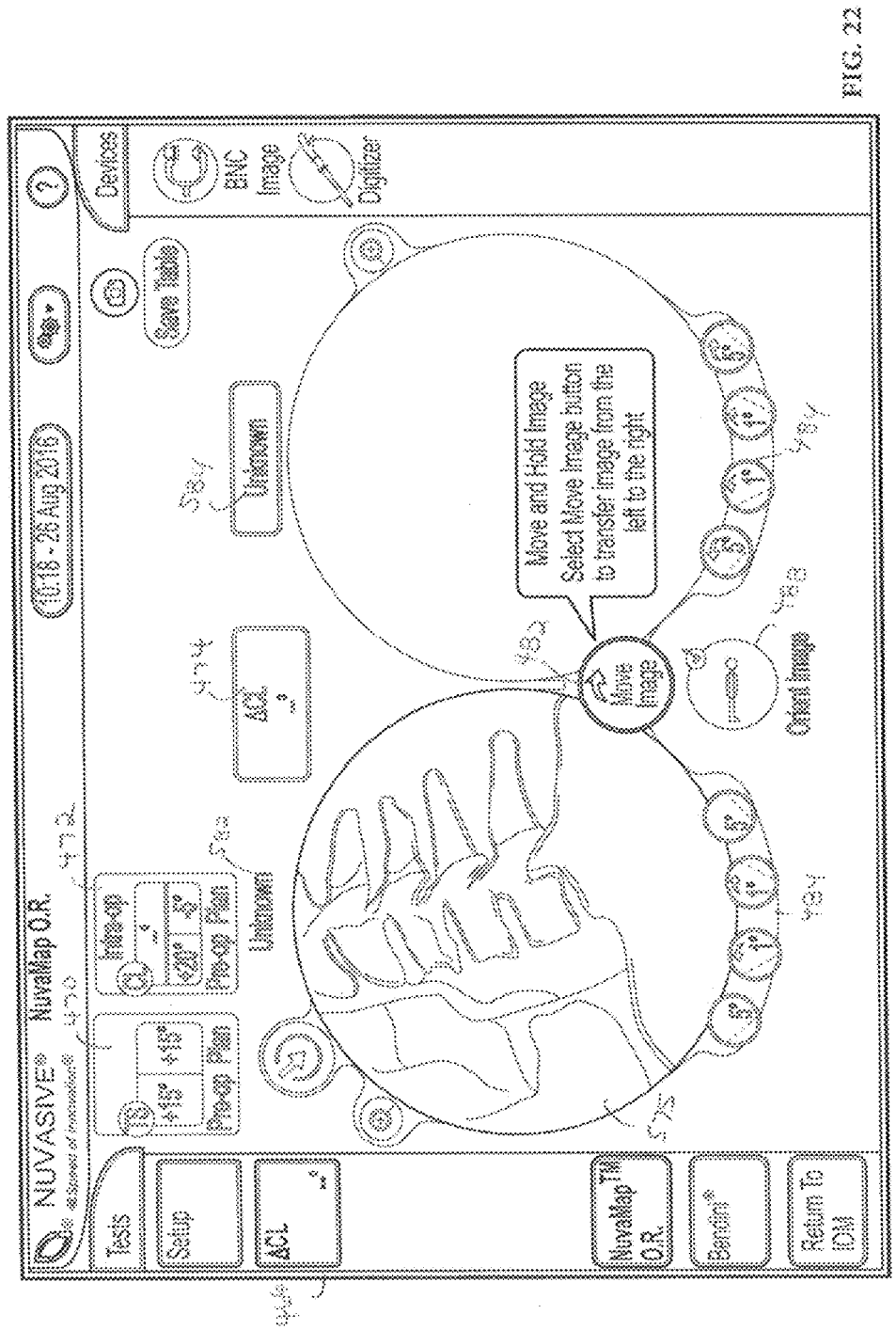
FIG. 22 is a screen shot illustrating an example of the oriented image according to the embodiment of FIG. 15.
Figure 23:
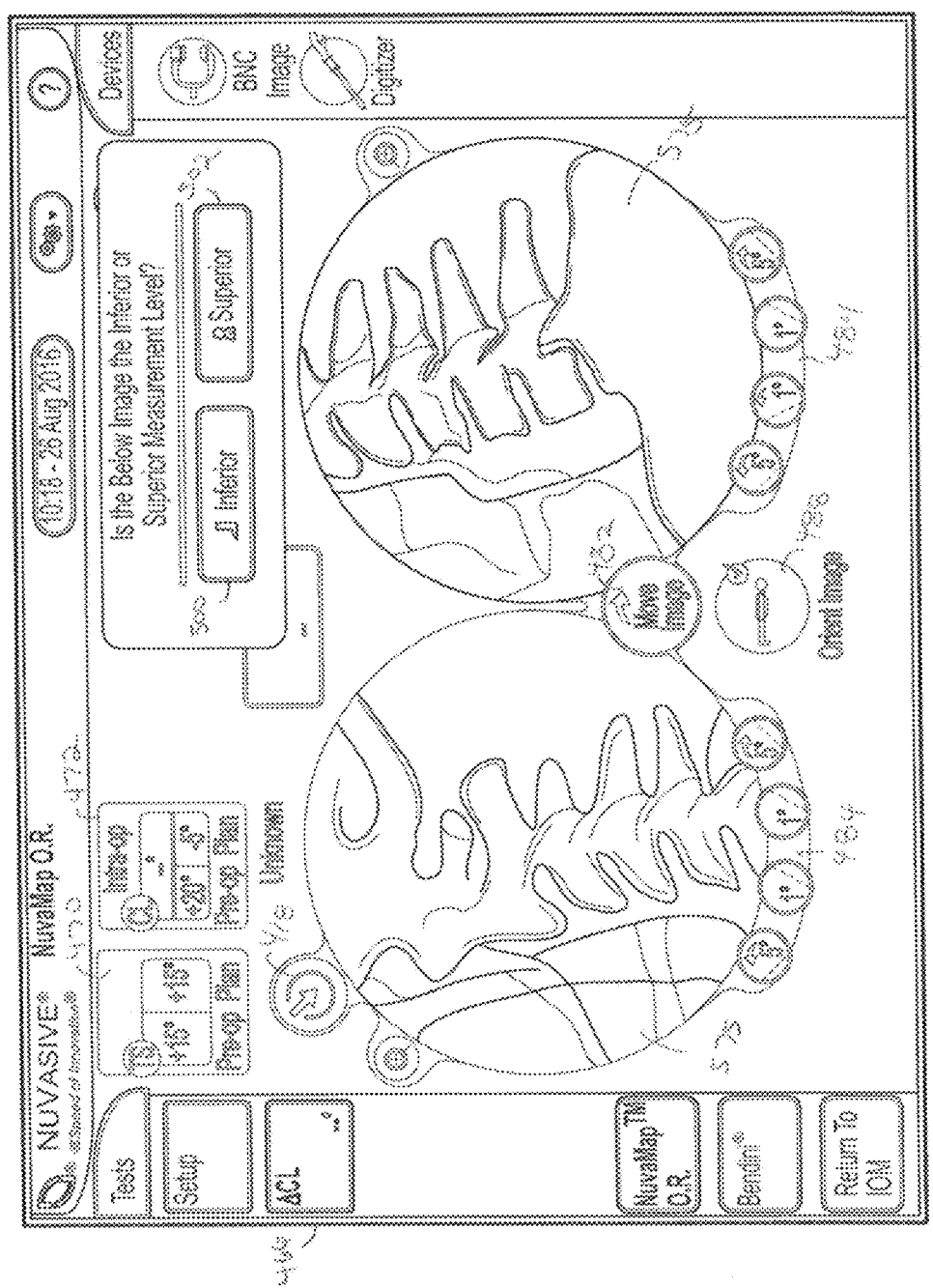
FIG. 23 is a screen shot illustrating an example of importing of a second image according to the embodiment of FIG. 15.

FIGS. 17-27, depict the intraoperative measurement of cervical parameters according to one embodiment. As shown by way of example in FIG. 17, from the Set-Up screen, the User may first select the Cervical button 450. Next, as shown in FIG. 18, a first lateral radiographic image 575 may be inputted into the system 10 by selecting the Import Fluoro Image button 418. FIG. 19 shows a representative image of the window 420 after an image has been inputted. The images 575 in the left window 478 or right window 480 may be expanded by selecting the + button 580 to fill the screen with the selected image. The user may switch between the left window 478 and the right window 480 by selecting the image identification button 582, 584 located above each window. The image orientation may be identified by selecting the Orient Image button 488. The User identifies the posterior of the patient's anatomy by selecting the appropriate Posterior button 490, as shown for example in FIG. 20. The User identifies the location of the head in the image by selecting the appropriate Head button 498, as shown for example in FIG. 21. Once the orientation of the image has been established, it is not necessary to identify the orientation of subsequent C-arm images unless the position of the C-arm is moved during the surgery. The first lateral radiographic image may be moved from the left window 478 to the right window 480 by selecting the Move Image button 488. As shown in FIG. 23, the User may select the Inferior 500 or Superior button 502 to identify which cervical segment is captured in the first image. A second lateral radiographic image 575 of the opposite segment, Inferior or Superior, may be inputted into the system 10 as shown in FIG. 23. After the orientation is set, the image identification buttons 582, 584 indicate which segment is shown in the image beneath, Superior or Inferior.

Figure 24:
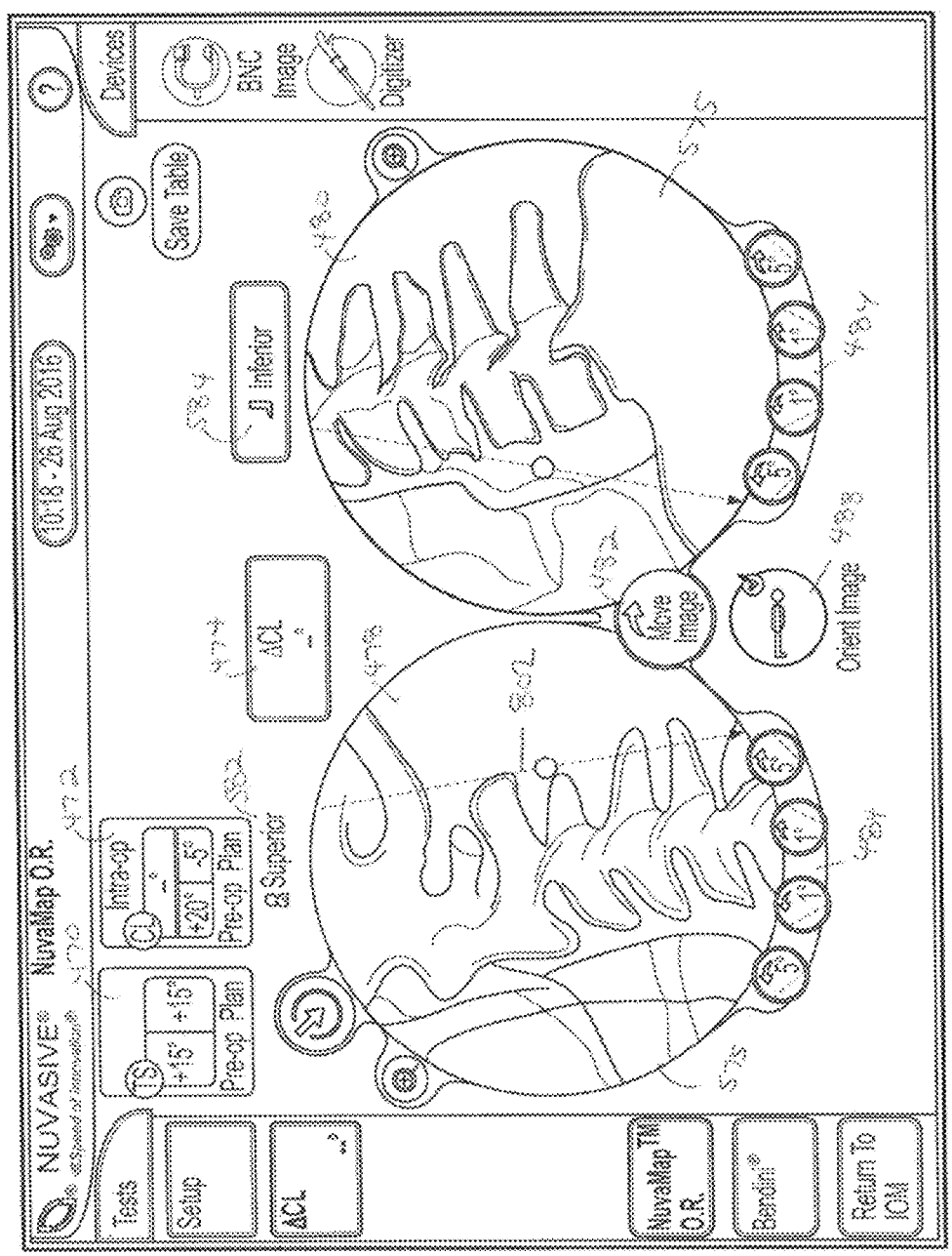
Figure 23:
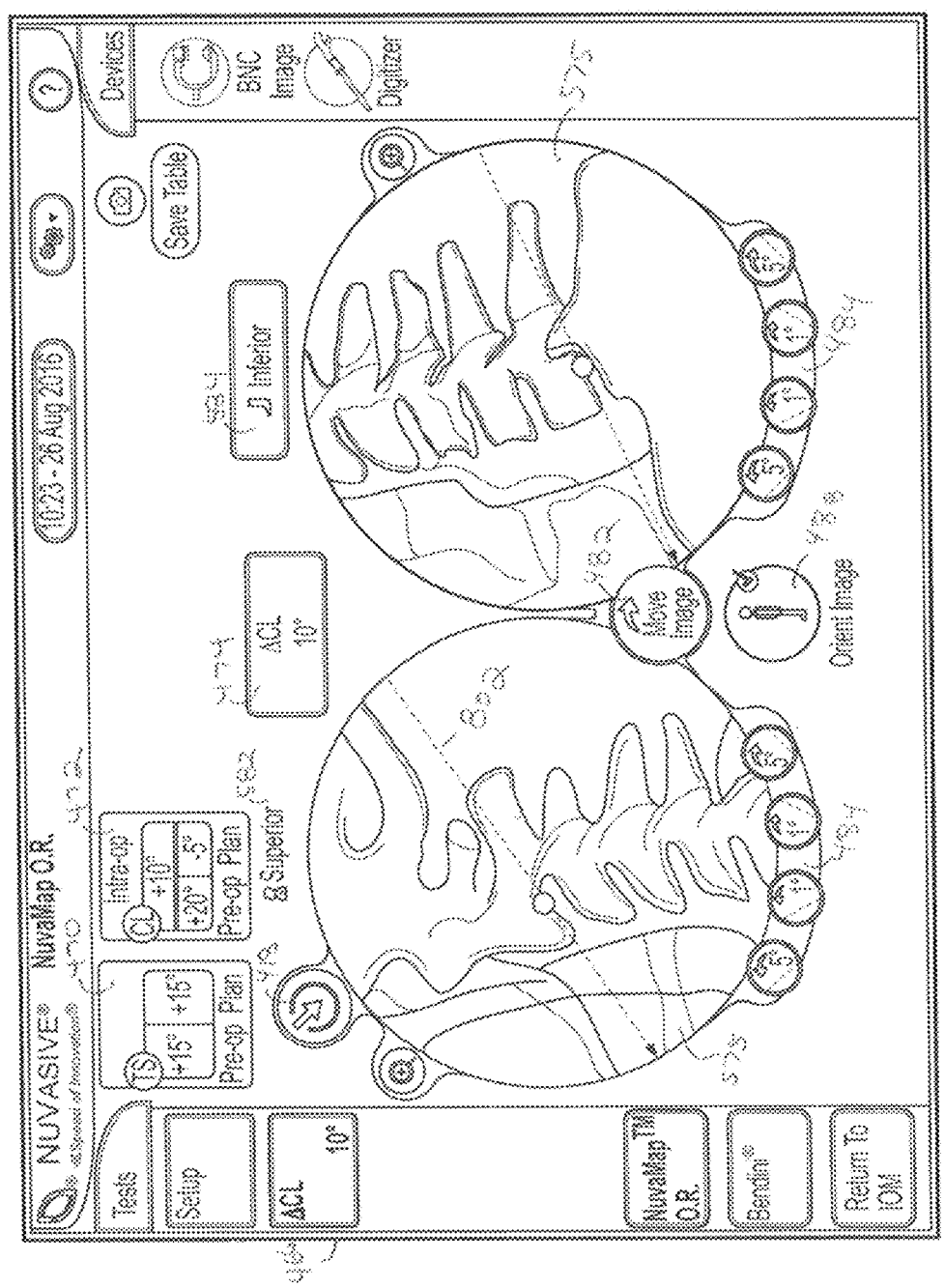
Figure 26:
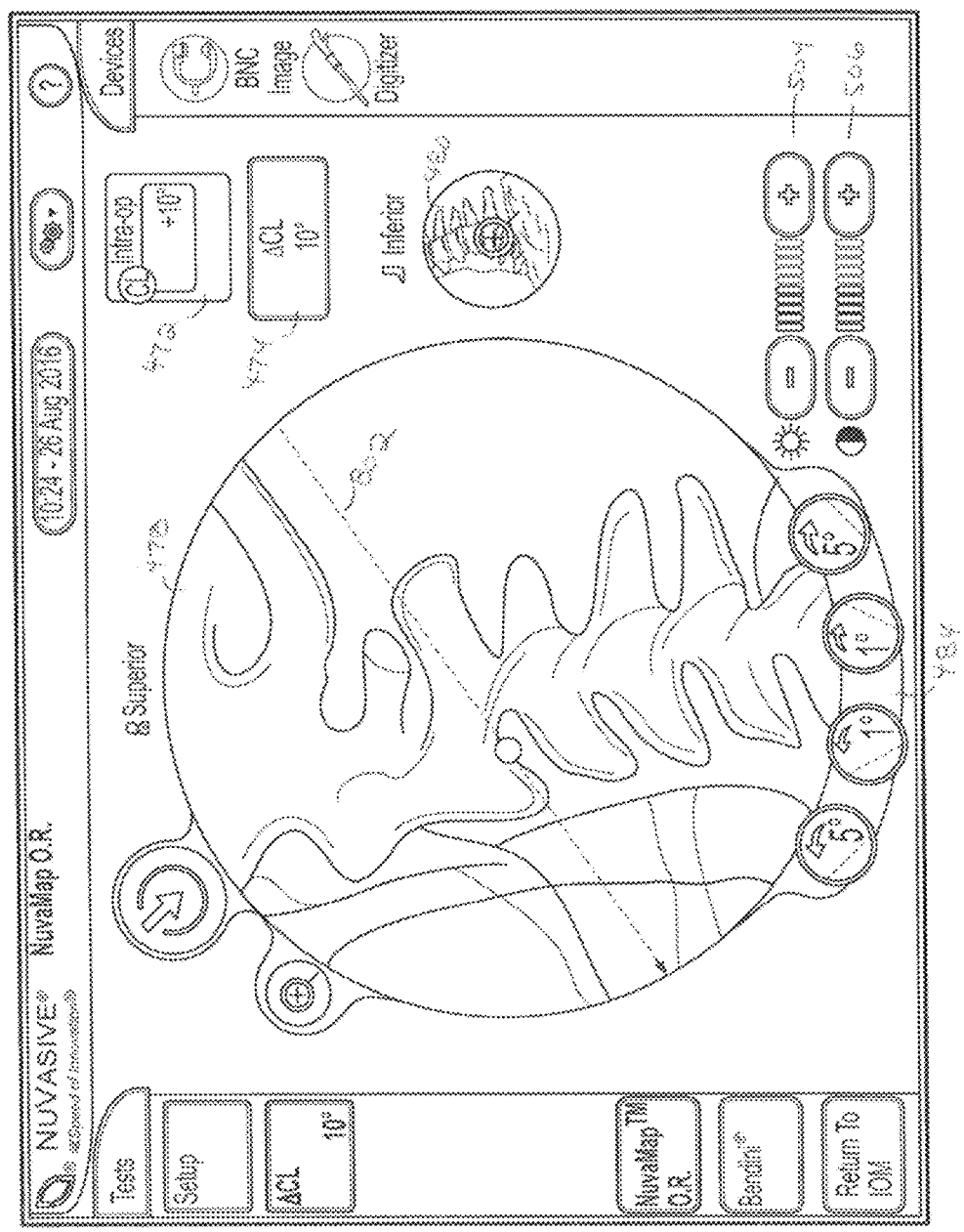

According to some embodiments, a User may identify landmarks of the spine by moving lines over at least two points of interest (e.g. the superior endplate of V1 and the superior endplate of V2) The system 10 then measures the angle between the two lines. For example, as shown in FIGS. 24-26, to calculate CL the User may identify the endplate of C2 in the superior image and the endplate of C7 in the inferior image. First, a C2 endplate line 802 is placed on the image 575 as shown in FIG. 24. The line 802 is then adjusted to align with the endplates by pressing the Angle buttons 484 to increase or decrease the angle until the line 802 overlays the endplate. As shown in FIG. 25, the system 10 measures this angle as 10 degrees as indicated in the angle measurement field 474.

Optionally, the system 10 may compare the intraoperative measurement to the preoperative and/or target spinal parameter value and provide an indication to the User of how much correction has been achieved relative to the pre-operative and theoretical spinal parameters. As shown in FIG. 25. The values in the CL value display window 472 indicate the preoperative CL was measured at +20 degrees, the planned CL was −5 degrees, and the intraoperative CL was measured at +10 degrees. Therefore, the system calculates the change in CL (ΔCL) as 10 degrees as indicated in the measurement field 474. As shown in FIG. 26, the left window 478 has been zoomed and the right window 480 minimized. To enhance visibility and increase accuracy of the line placement, the image may be manipulated to increase or decrease the brightness 504 or contrast 506 by using the + and − buttons. Using the angle measurement buttons 484, the User may increase the desired angle of correction of the spine in the sagittal plane (i.e., add or subtract lordosis or kyphosis). As the angle is adjusted, the amount of adjustment may be dynamically displayed within the angle measurement field 472.

Figure 27:
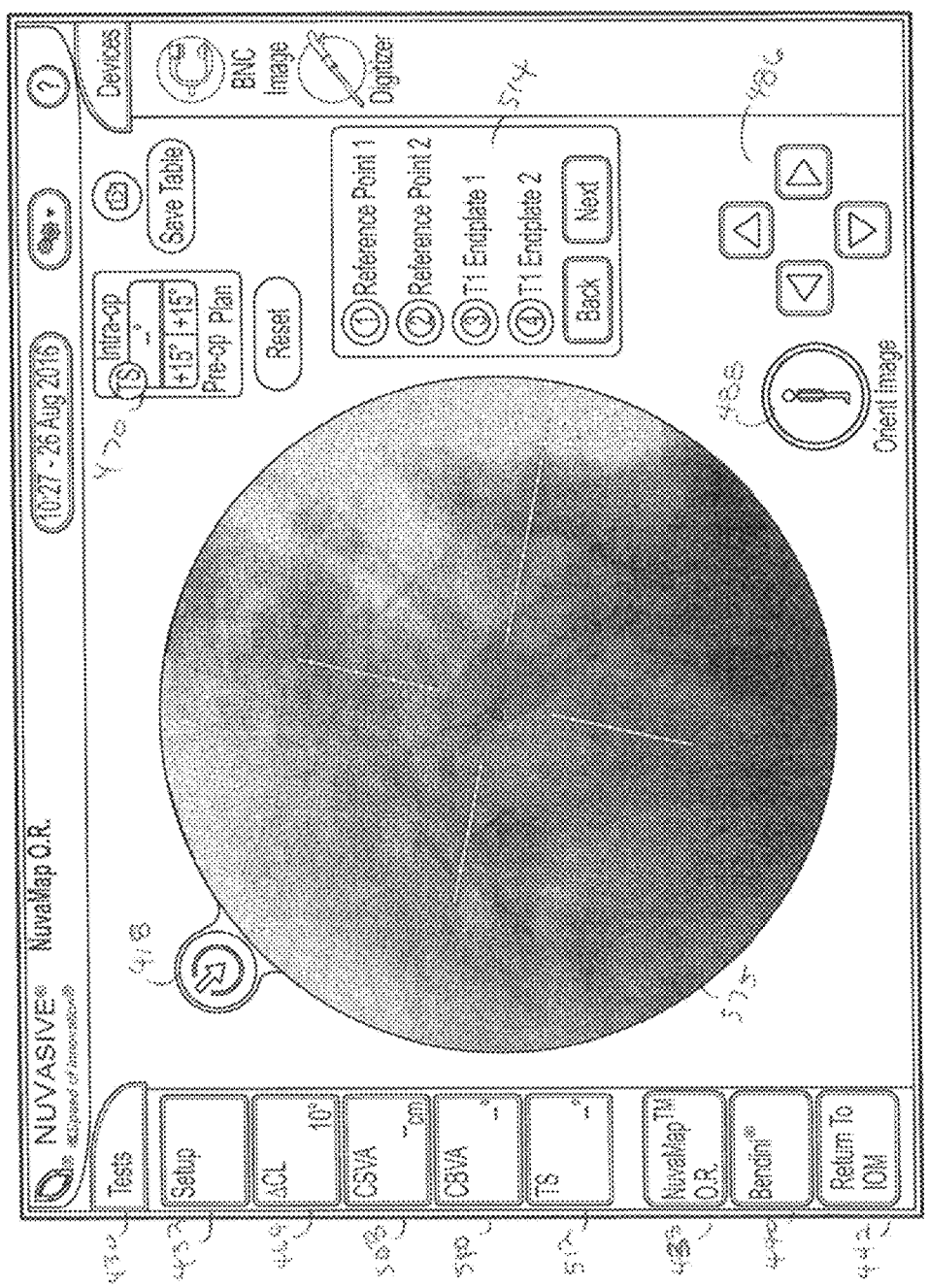
FIGS. 27-29 are screen shots illustrating an example measurement of T1 slope according to the embodiment of FIG. 15.
Figure 28:
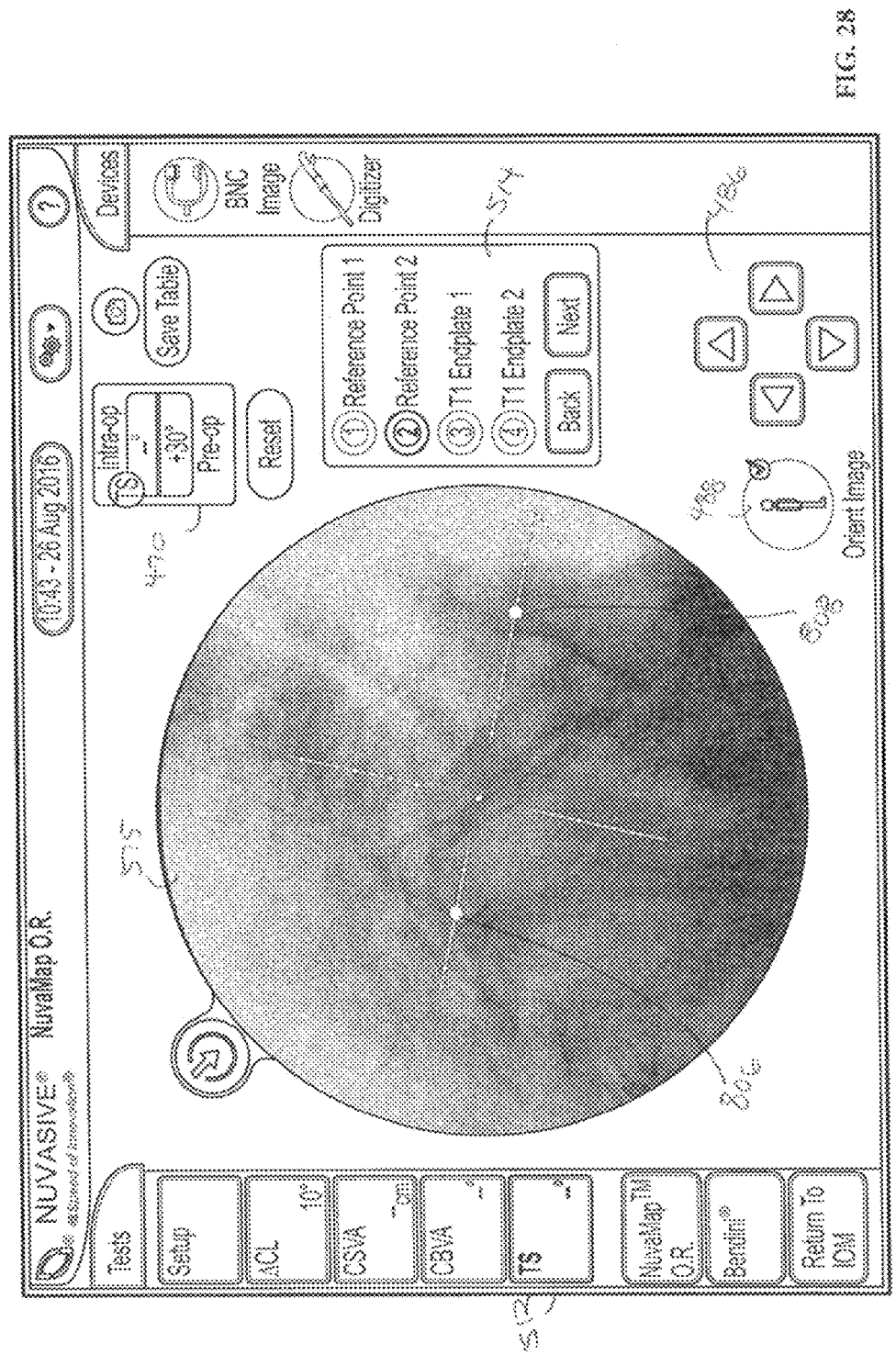
Figure 29:
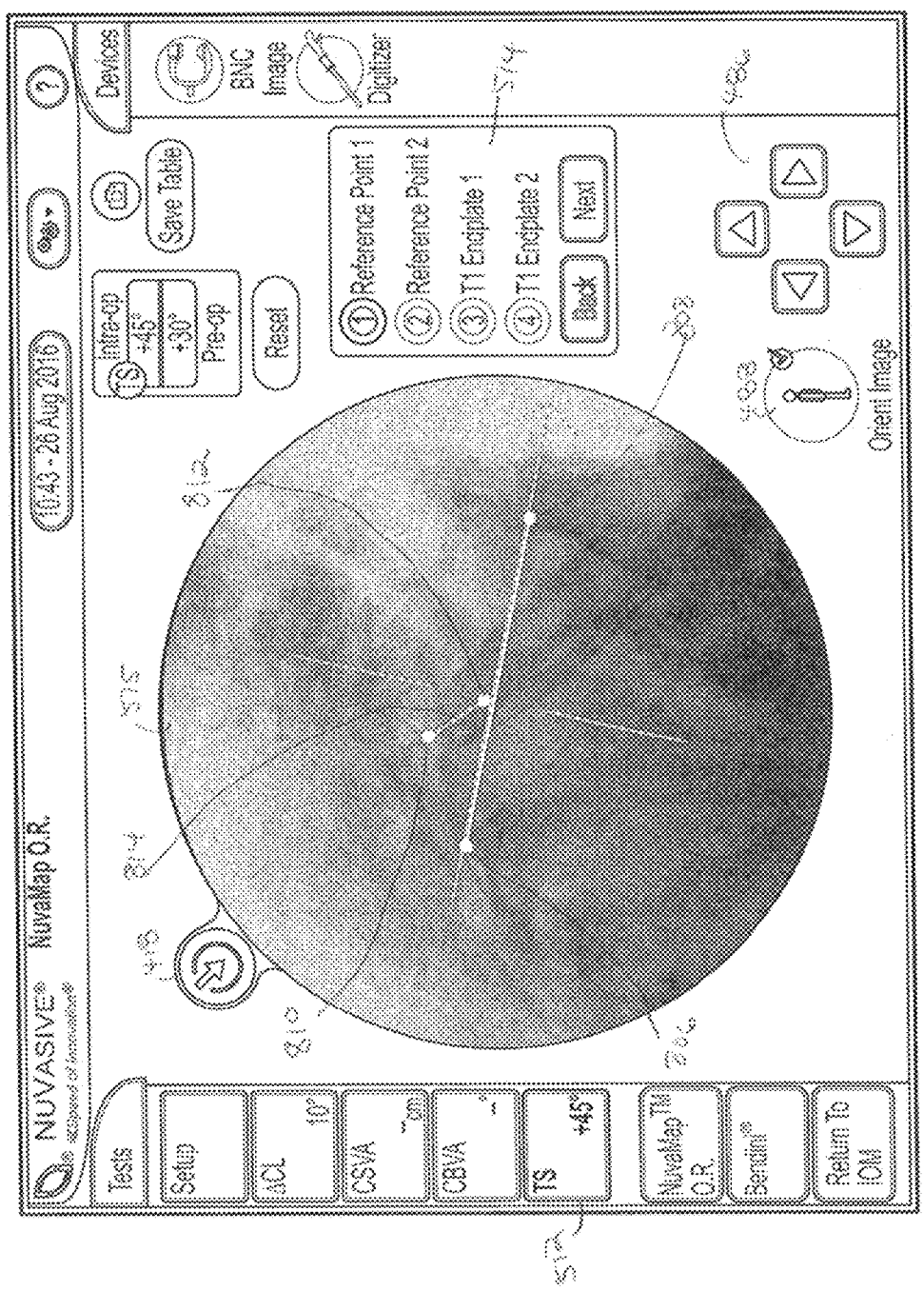

In some embodiments, the User may optionally wish to intraoperatively measure a second anatomical or cervical characteristic, such as the patient's T1 Slope (TS). As shown in FIG. 27, selecting the TS measurement button 512 optionally brings up a TS assessment tool. A fluoroscopic image 575 of the patient's cervical spine is inputted into the system 10. If necessary, the image may be oriented as previously described. The method of calculating TS is illustrated in FIGS. 28-29. First, as shown in FIG. 28, a horizontal line can be established by use of a reticle affixed to the c-arm. To establish the line, the User selects the Reference Point 1 button 514a in the TS tool 514 and uses the arrow array 486 to identify a first point 806 on the horizontal line 804 of the reticle. Next, the User selects the Reference Point 2 button 514b and uses the arrow array 486 to identify a second point 808 on the horizontal line 804. Next, as shown in FIG. 29, the User then selects the T1 Endplate 1 button 514c to identify the posterior aspect of the T1 end plate 810. Finally, the User selects the T1 Endplate 2 button 514d and uses the arrow array 486 to identify the anterior aspect of the T1 end plate 812. With all TS inputs selected, the control unit 16 calculates a line 814 between the posterior 810 and anterior 812 points. The angle between the T1 endplate line 814 and the horizontal line 804 can then be measured by the control unit 16, thus resulting in the TS angle. In the example shown in FIG. 29, the system 10 measures this angle as 45 degrees as indicated in the TS measurement field 470.

From the measured CL and TS, the system 10 may calculate the TS-CL measurement and provide color-coded feedback to the User regarding the degree of deformity. The value of TS-CL may be displayed, for example, in a Green color when the value is non-pathologic (TS-CL<+/−15 degrees), in a Yellow color when the value indicates there is a potential moderate deformity (+/−15≤TS≤+/−20 degrees), and in a Red color when the value indicates there is a potential for a marked deformity (TS-CL≥+/−20 degrees).

Figure 30:
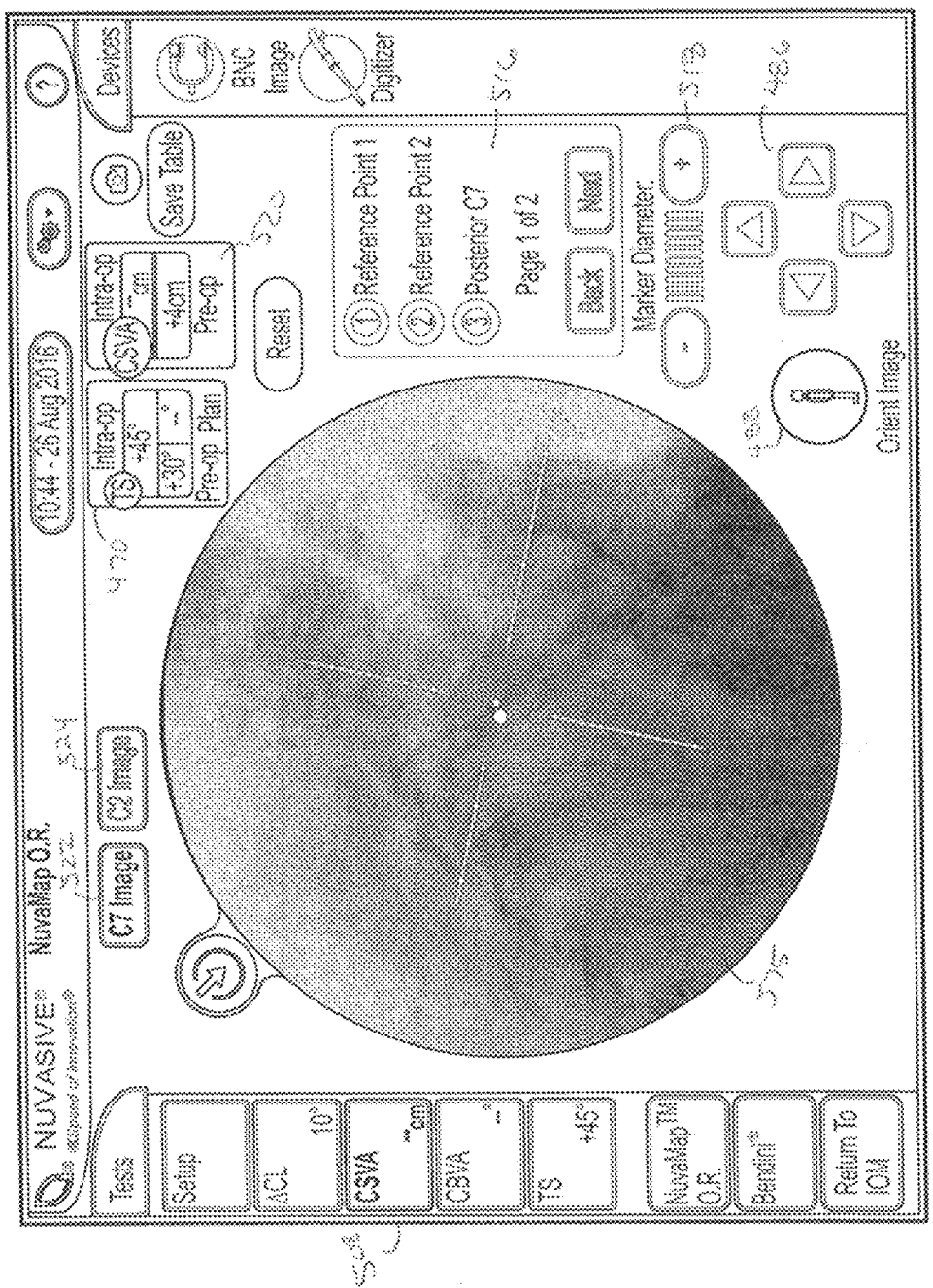
FIGS. 30-34 are screen shots illustrating an example measurement of cervical sagittal vertical axis according to the embodiment of FIG. 15.
Figure 31:
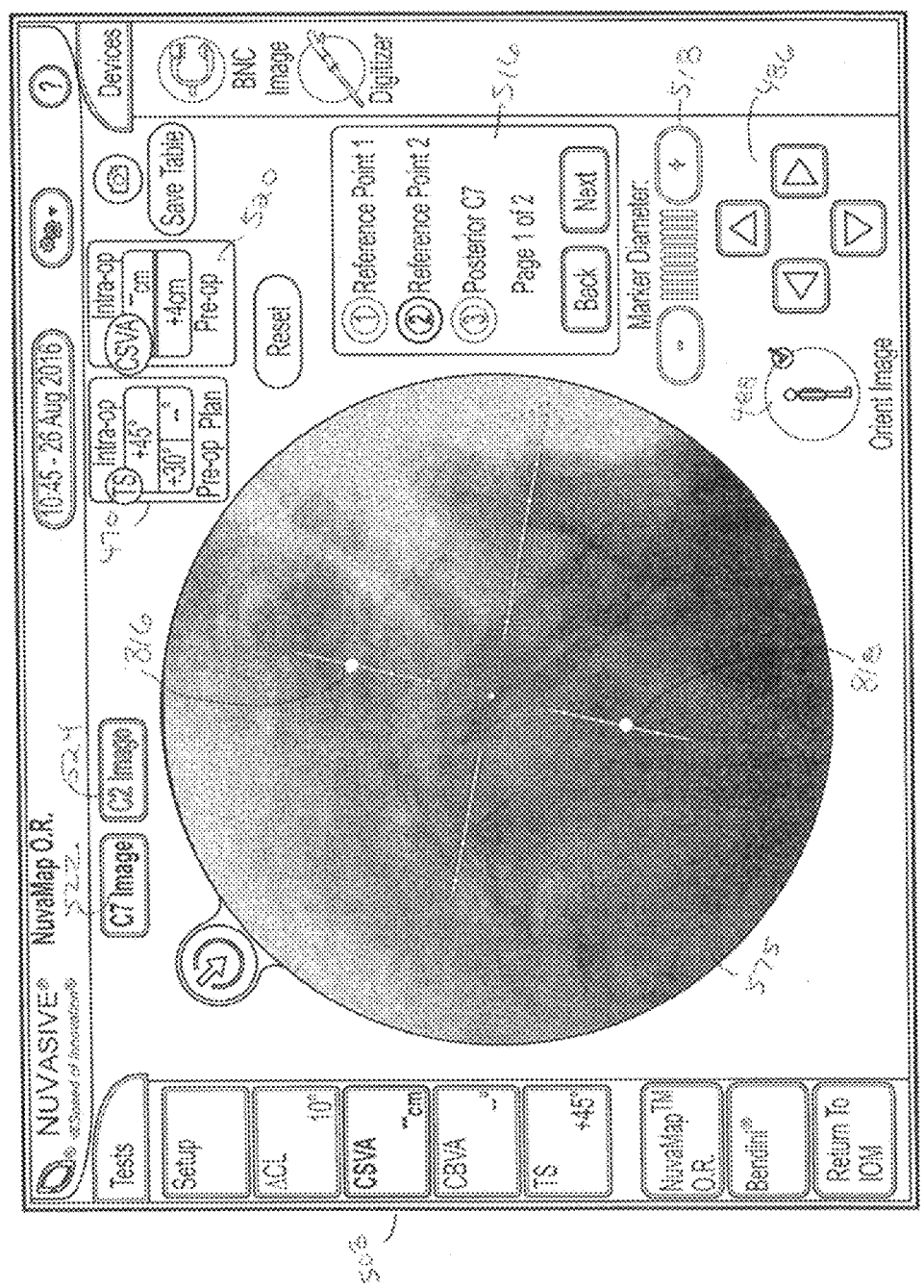
Figure 32:
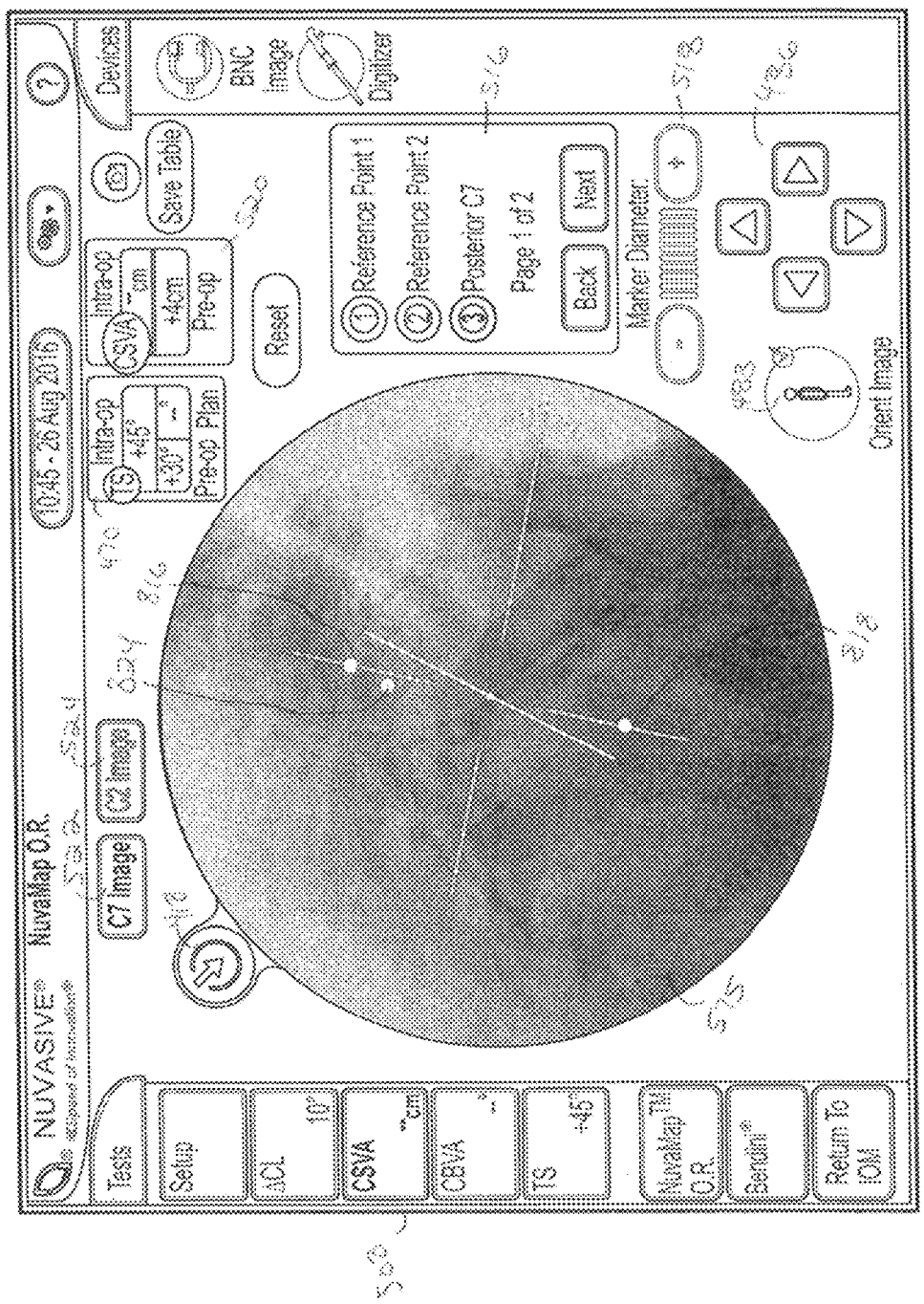
Figure 33:
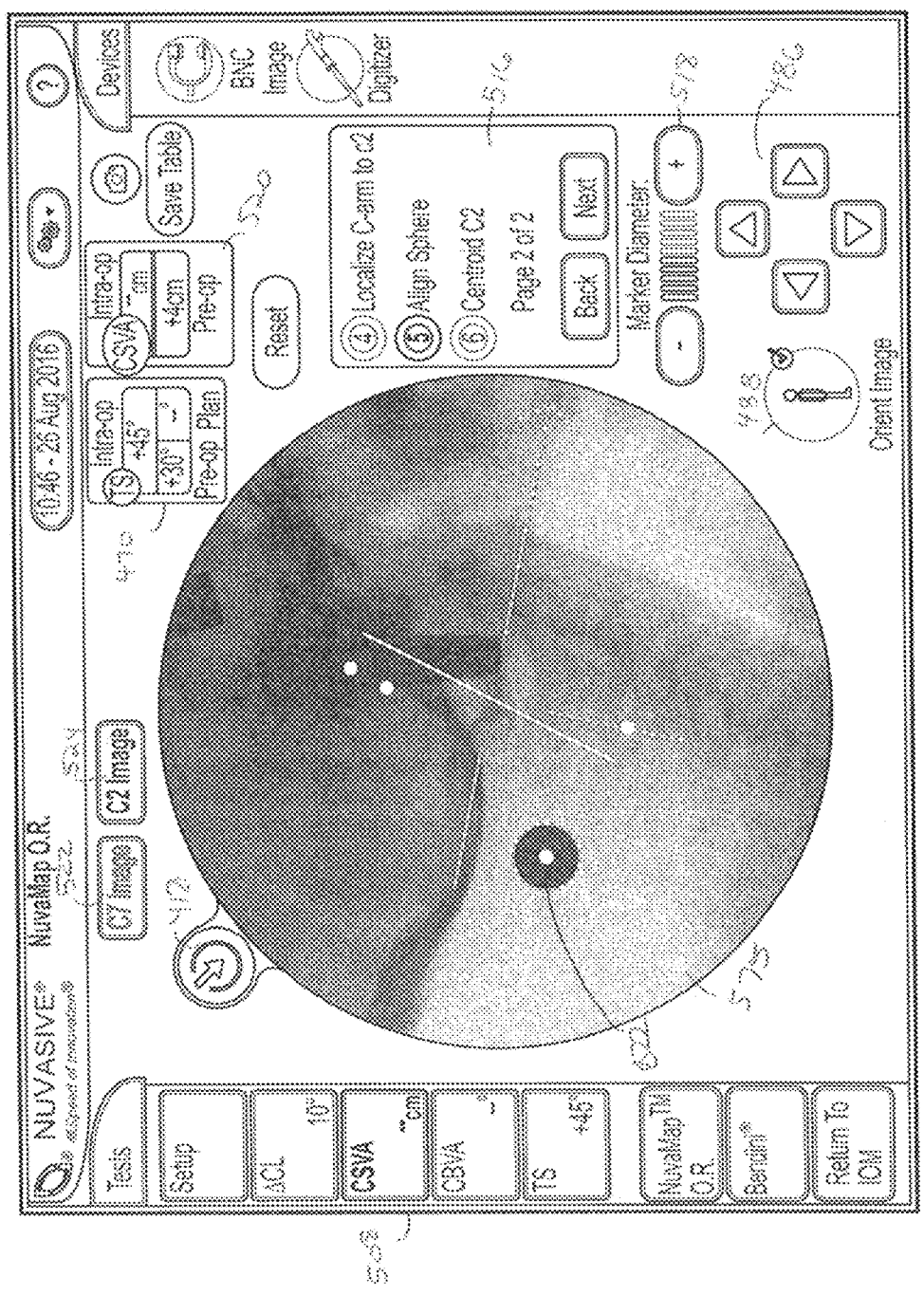
Figure 34:
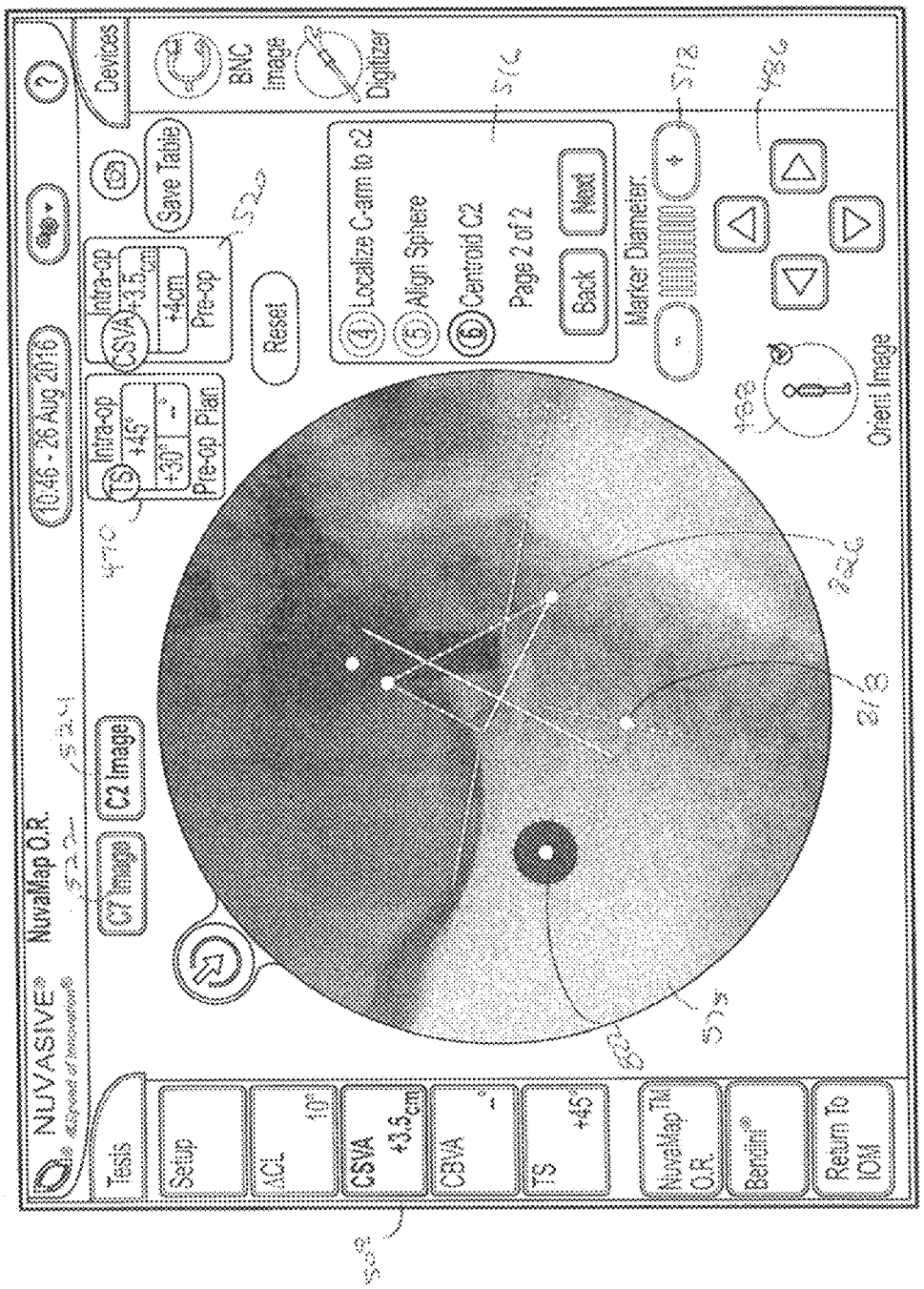

In some embodiments, it may also be desirable to determine the intraoperative cervical sagittal vertical axis (CSVA). This may involve the use of a reticle and a central radio dense marker 822 placed on the c-arm receiver to allow a true vertical axis to be identified. Selecting the CSVA button 508 optionally brings up a CSVA tool 516. As shown in FIGS. 30-32, a first fluoroscopic image may be taken of the inferior cervical region, aligned over C7. The User may first select the Reference Point 1 button 516a and use the arrows to select a first position 816 on the line of the reticle. The User then may select the Reference Point 2 button 516b and use the arrows to select a second position 818 on the line of the reticle. These reference points identify a vertical line 820. The User then selects the Posterior C7 button 516c, and uses the arrow array 486 to identify the position of the posterior corner of the C7 superior end plate 824. The User may then relocate the c-arm such that it is aligned over the superior cervical spine and C2 as shown in FIG. 33. The User aligns the marker 822 and increases or decreases the diameter of the marker with the marker diameter buttons 518. After alignment, the User may select the Centroid C2 button 516f and use the arrow array 486 to identify the midbody of the C2 vertebral body 826. The User may move back and forth between the C7 and C2 images by selecting the appropriated button 522, 524. In alternative embodiments, a single fluoroscopic image may be taken wherein both the C7 and C2 vertebrae are visible in one image. The vertical line is determined by marking two points on the reticle line. The posterior C7 and centroid C2 are identified as described above. The system 10 may calculate the CSVA measurement and display the values in a CSVA measurement field 520. In some embodiments, the system 10 may provide color-coded feedback to the User regarding the degree of deformity. The value of CSVA may be displayed, for example, in a Green color when the value is non-pathologic (CSVA<+/−4 cm), in a Yellow color when the value indicates there is a potential moderate deformity (+/−4 cm≤CSVA≤+/−8 cm), and in a Red color when the value indicates there is a potential for a marked deformity (CSVA≥+/−8 cm). As shown in the CSVA measurement field 520 in FIG. 34, the system has calculated CSVA in the present example to be +3.5 cm. The system may also display the pre-operative value of CSVA which is shown in this example to be 4 cm.

Figure 35:
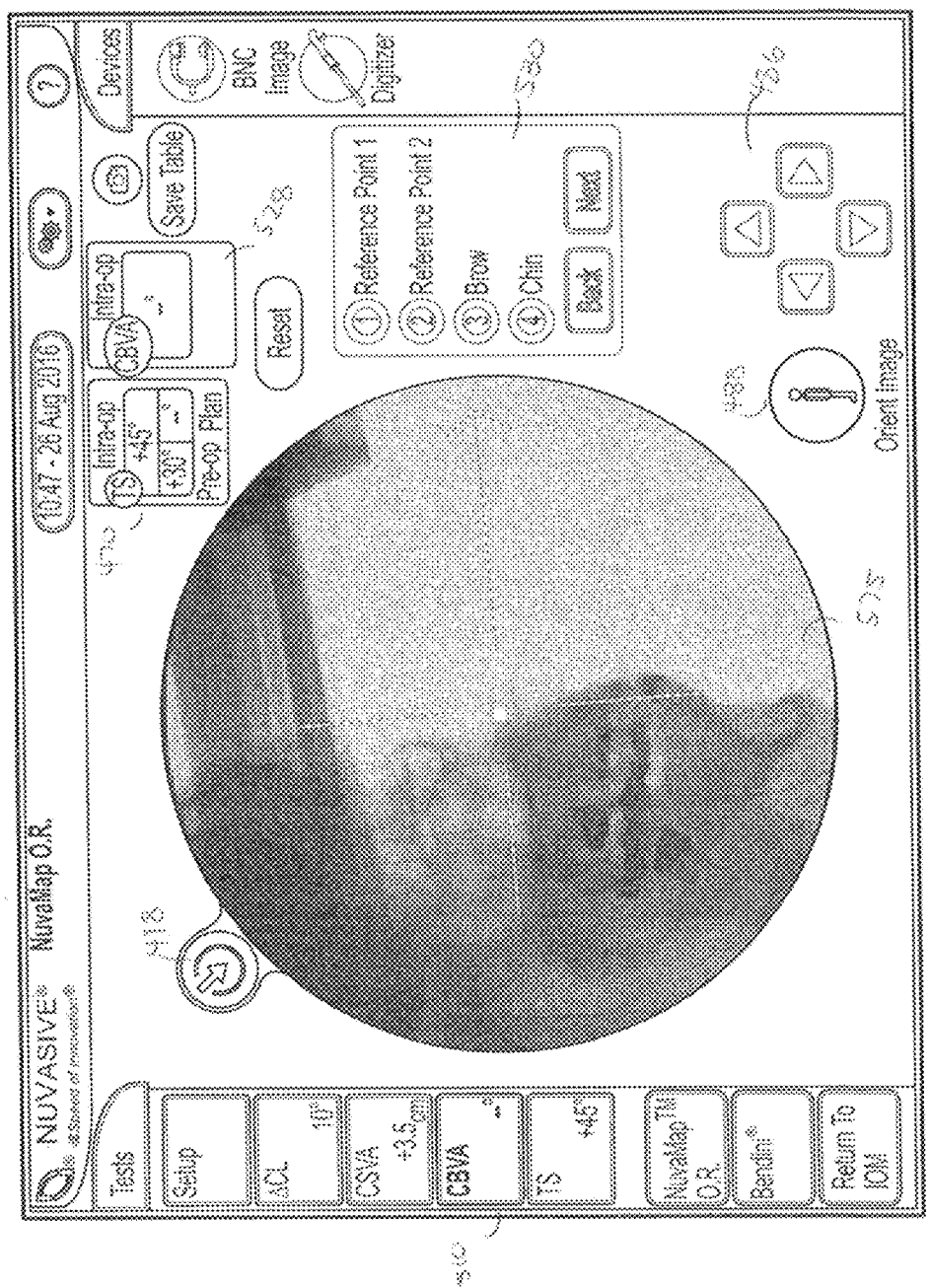
FIGS. 35-39 are screen shots illustrating an example measurement of chin brow vertical angle according to the embodiment of FIG. 15.
Figure 36:
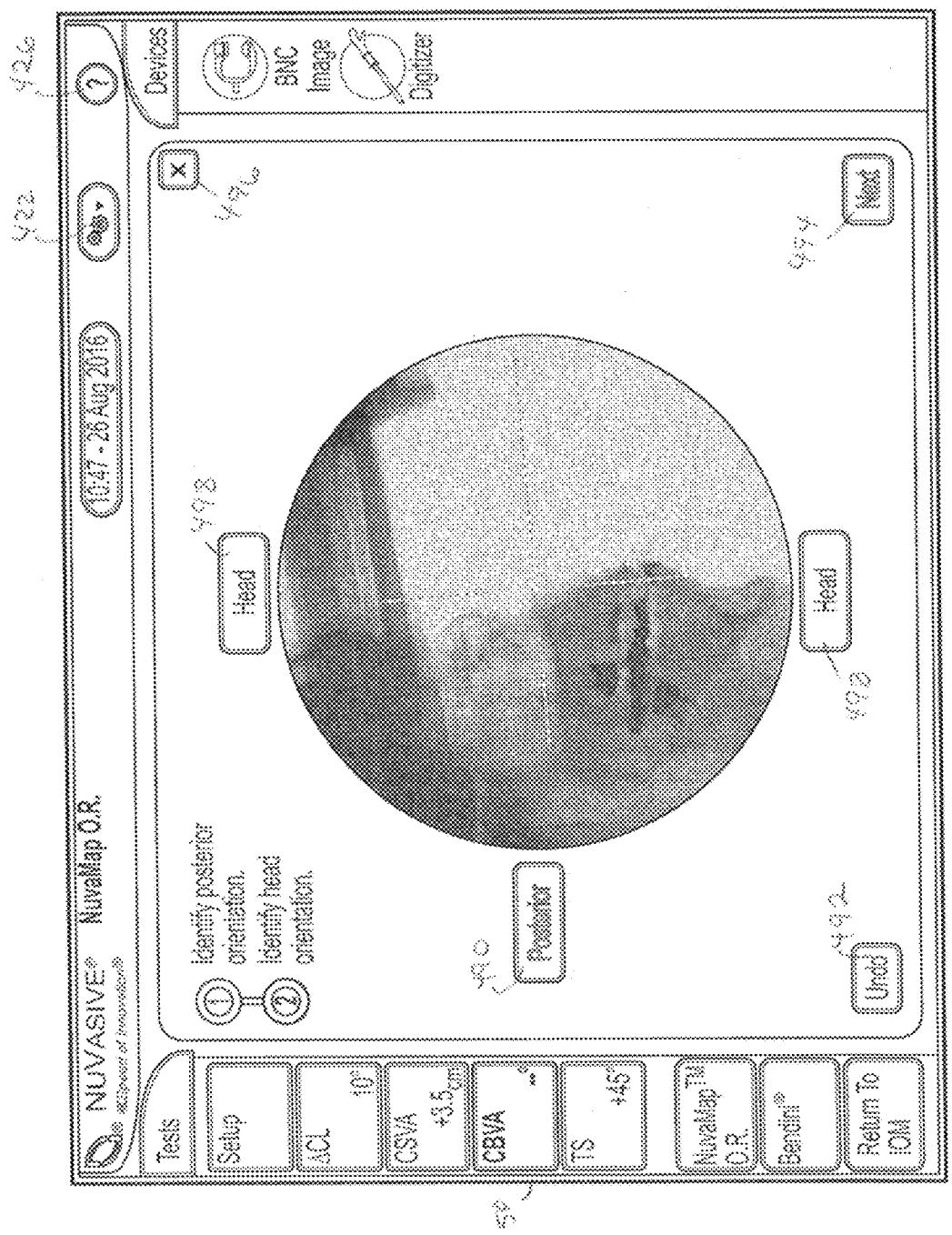
Figure 37:
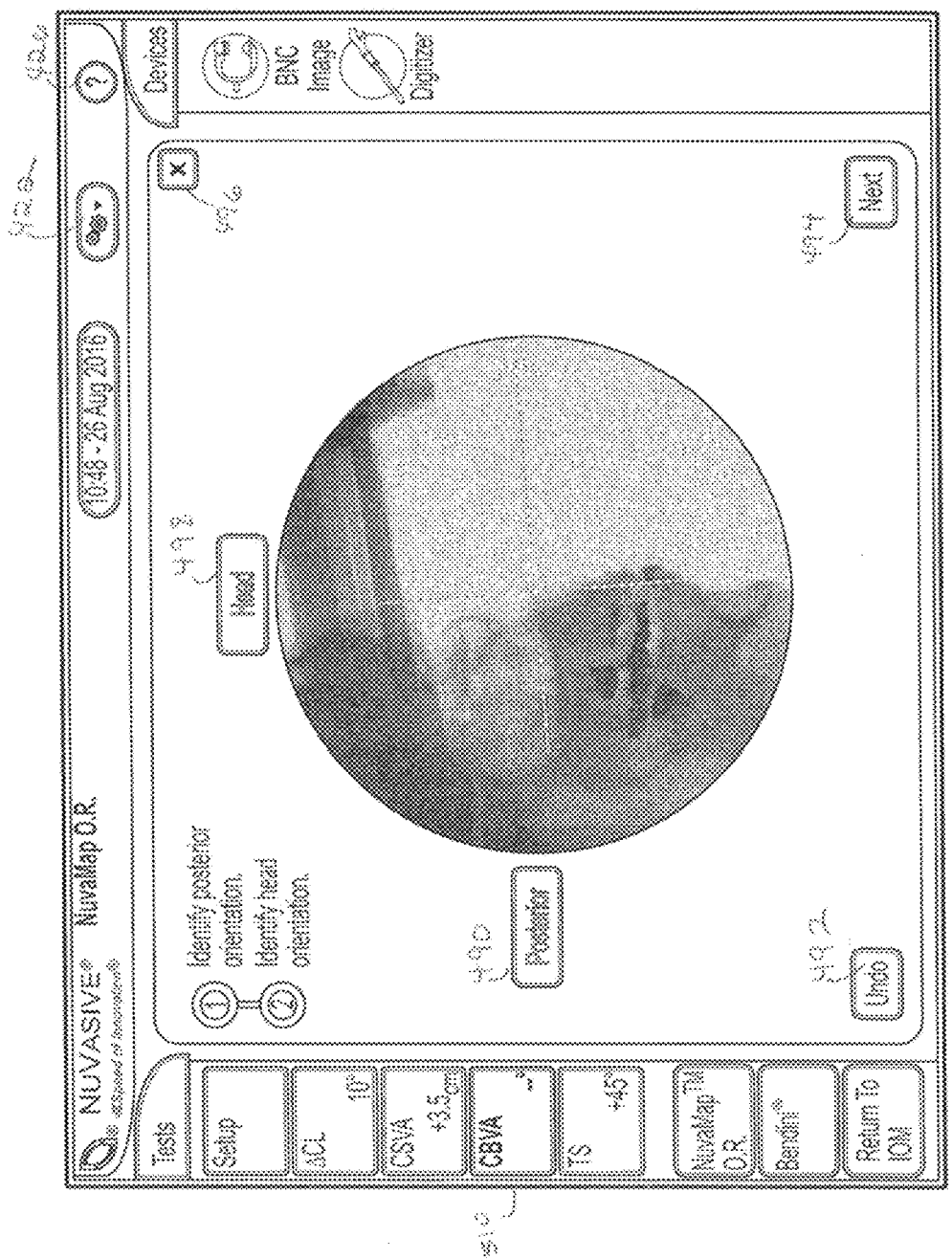
Figure 38:
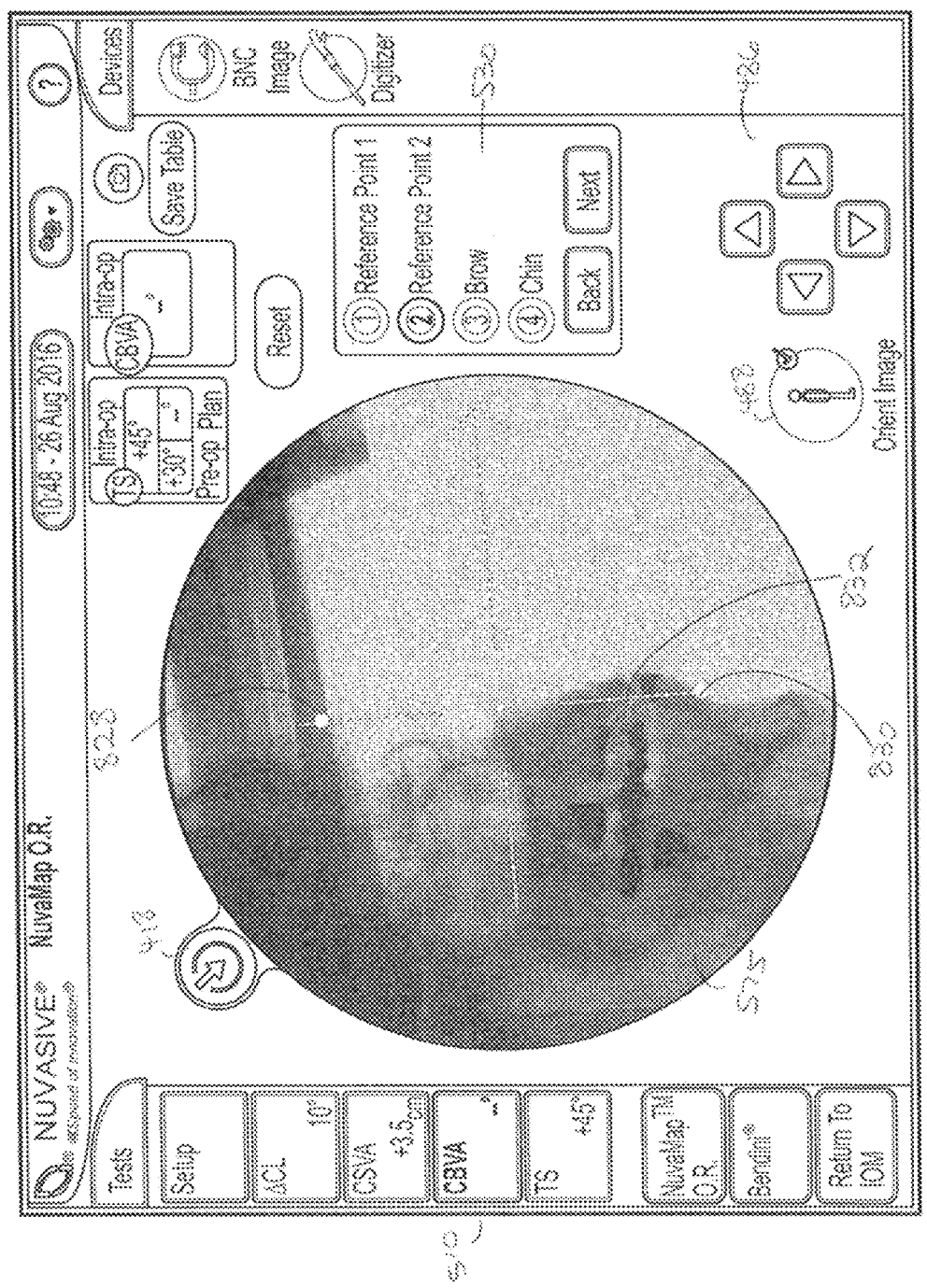
Figure 39:
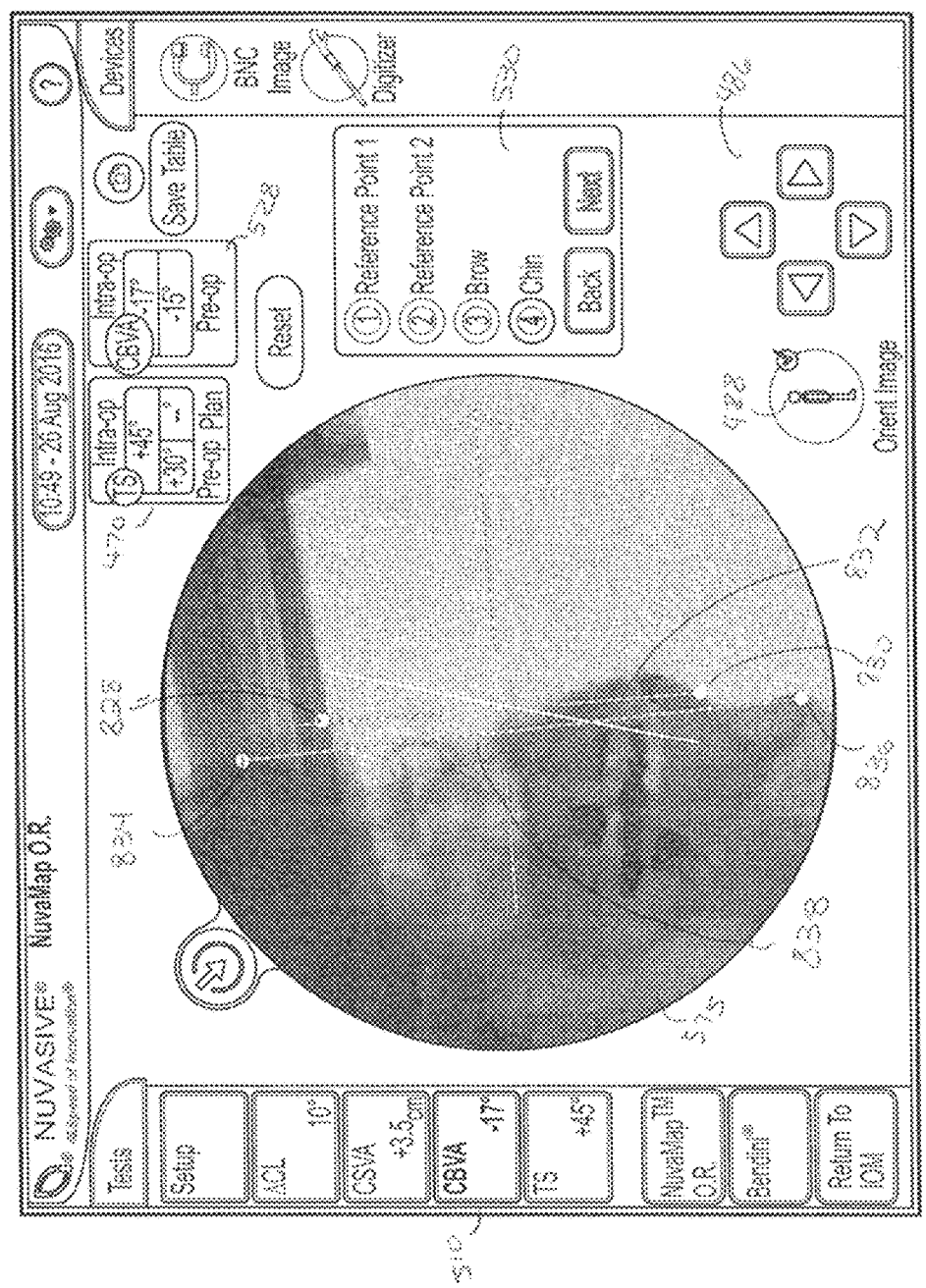

The chin brow vertical angle (CBVA) may optionally be determined in some embodiments. This can be accomplished by using a guidance reticle, or positioning two radio dense markers (not shown) at the 12 and 6 o'clock positions on the c-arm receiver face. Selecting the CBVA button 510 optionally brings up a CBVA tool 530. As shown in FIGS. 35-37, a fluoroscopic image can be taken of the cranium and oriented as described above. The User then establishes a true vertical line as shown in FIG. 38. The user may first select the Reference Point 1 button 530a and use the arrow array 486 to select a first position 828 on the line of the reticle. The User may then select the Reference Point 2 button 530b and uses the arrow array 486 to select a second position 830 on the line of the reticle. These reference points identify a true vertical line 832. The User then may measure the line between brow and chin as shown in FIG. 39. The User may select the Brow button 530c, and uses the arrow array to identify a point on the brow 834. The User then selects the Chin button 530d, and uses the arrows to identify a point on the chin 836. The system 10 automatically draws and calculates the angle between a line from chin to brow 838 and the vertical axis 832, thus resulting in the CBVA. The value of CBVA may be displayed, for example, in a Green color when the value indicates the patient has an acceptable gaze position relative to the horizon, in a Red color when the value indicates there is a potential that the patient has an unacceptable gaze position, too high or too low relative to the horizon, and in a Yellow color when the value indicates there is a potential that the patient's gaze position may be at an intermediate level of acceptability. As shown in the CBVA measurement field in FIG. 39, the system has calculated CBVA in the present example to be −17 degrees. The system may also display the pre-operative value of CBVA which is shown in this example to be −15 degrees.

Figure 40:
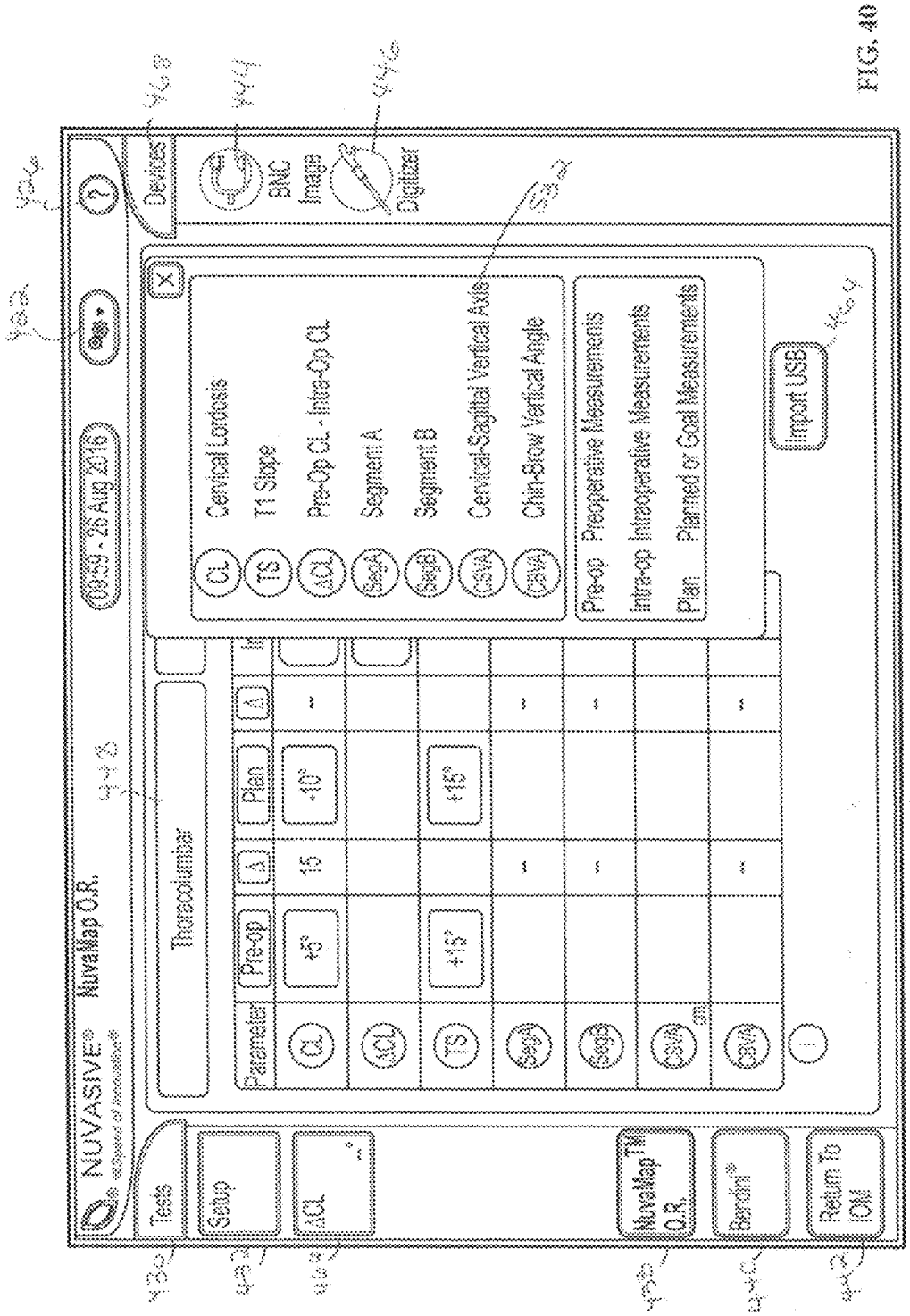
FIG. 40 is a screen shot illustrating an example a definitions screen according to the embodiment of FIG. 15.

FIG. 40 provides an example of a definitions page which may be included to define the abbreviations for the User.

The User may optionally measure the patient's thoracolumbar parameters to assess global alignment of the spinal column. The method of measuring and calculating thoracolumbar parameters may be any known in the art. By way of example only, the system and methods for measurement and calculation of thoracolumbar parameters may be those described in U.S. patent application Ser. No. 15/045,084 entitled "Systems and Methods for Planning, Performing, and Assessing Spinal Correction During Surgery" and filed on Feb. 16, 2016, the entire contents of which are hereby incorporated by reference as if set forth fully herein.

Although the methods described above are referred to as intraoperative, it will be appreciated that the same systems and methods are equally applicable to pre-operative and post-operative measurements of spinal parameters.

Rod Bending

Referring back to the embodiment of a surgical planning, assessment, and correction system 10 as shown in FIG. 1, the system 10 includes a spatial tracking system 12 to obtain the location of one or more surgical implants 14, a control unit 16 containing software to convert the implant locations to a series of bend instructions, and a bending device 18 to execute the bend instructions.

Preferably, the spatial tracking system 12 includes an IR position sensor 20, a digitizer pointer 23, as well as other components including Host USB converter 21. The spatial tracking system 12 is in communication with control unit 16. The control unit 16 has spatial relation software and C-aim video import capabilities and is communicatively linked to the display 32 so that information relevant to the surgical procedure may be conveyed to the User in a meaningful manner By way of example, the relevant information includes, but is not limited to, spatial positioning data (e.g., translational data in the x, y, and z axes and orientation/rotational data $R_x$, $R_y$, and $R_z$) acquired by the IR position sensor 20 and intraoperative fluoroscopic images generated by the C-arm fluoroscope.

According to one or more embodiments, the system 10 comprises a neuromonitoring system communicatively linked to the spatial tracking system 12 and/or the C-arm via the control unit 16. By way of example only, the neuromonitoring system may be the neuromonitoring system shown and described in U.S. Pat. No. 8,255,045, entitled "Neurophysiologic Monitoring System" and filed on Apr. 3, 2008, the entire contents of which are hereby incorporated by reference as if set forth fully herein.

According to one or more embodiments, the system 10 comprises a digitizer pointer and IR-reflective tracking array component in communication with the control unit 16. By way of example only, the digitizer and IR-reflective tracking array system may be the digitizer and IR-reflective tracking array system shown and described in U.S. patent application Ser. No. 13/815,643, entitled "Systems and methods for performing spinal surgery" and filed on Mar. 12, 2013, the entire contents of which are hereby incorporated by reference as if set forth fully herein.

Figure 41:
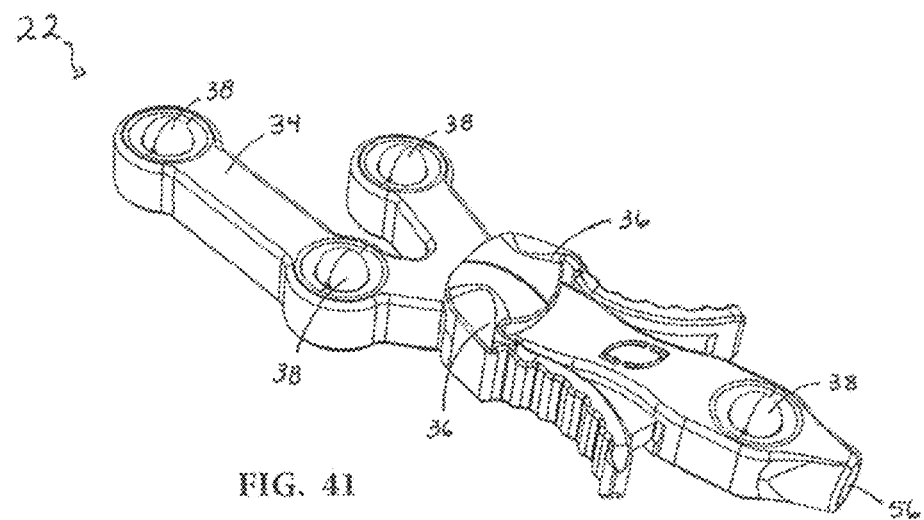
FIG. 41 is a perspective view of one embodiment of a digitizer array in the closed position comprising part of the system of FIG. 1.
Figure 42:
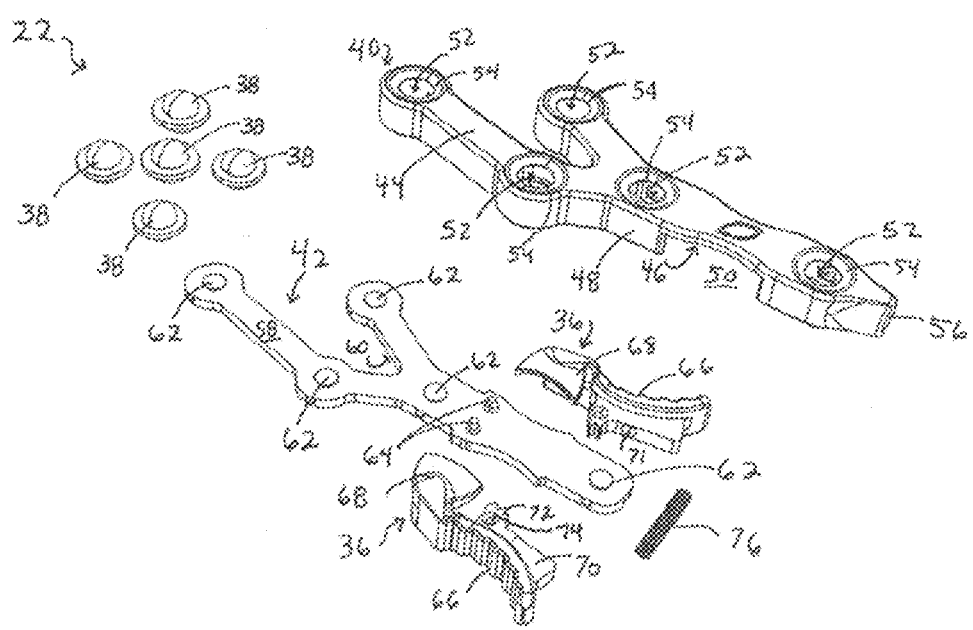
FIG. 42 is an exploded perspective view of the digitizer array of FIG. 41.
Figure 43:
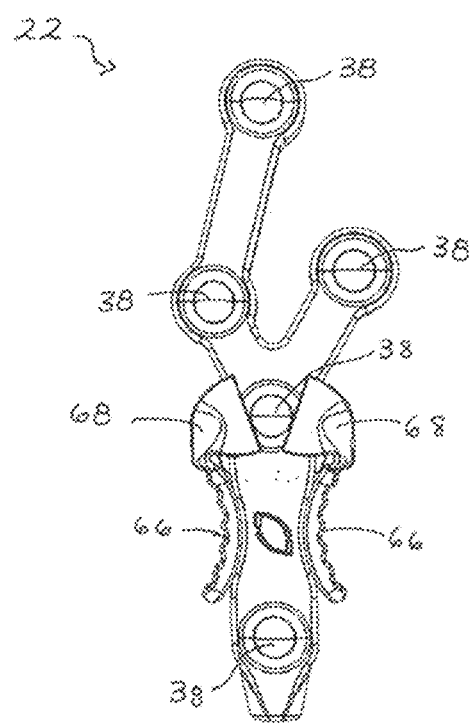
FIG. 43 is a perspective view of the digitizer array of FIG. 2 in the open position.

FIGS. 41-48 depict the various components of one or more digitizer pointers 23 for use with the present invention. FIGS. 41-43 detail an example IR-reflective tracking array 22 component of the digitizer pointer 23. Array 22 includes a housing 34, bilateral shutters 36, and a plurality of IR-reflective spheres 38 arranged in a calculated manner at various locations on the array 22 such that their position information is selectively detectable by the IR position sensor 20. Housing 34 comprises a top housing 40, bottom housing 42, and a distal threaded aperture 56 configured to threadably receive the threaded end 78 of a stylus (e.g., stylus 24, 26, 28, and/or 30). Top housing portion 40 is further comprised of upper portion 44, underside 46, and sides 48. A plurality of sphere apertures 52 extend between upper portion 44 and underside 46 and are sized and dimensioned to receive reflective spheres 38 within recessed pockets 54. Each side 48 includes cutout 50 sized and dimensioned to receive tongue 70. Bottom housing 42 is comprised of a first face 58 and a second face 60. The first face 58 includes nesting platforms 62 and bullet posts 64. Each shutter 36 includes handle portion 66, cover portion 68, tongue 70, interdigitating gear teeth 72, and channel 74 for receiving bullet posts 64. A spring 76 extends between the two shutters 36 and is held in place via spring posts 71.

In an assembled state, each IR-reflective sphere 38 is nested on a platform 62. Top housing 40 is placed over bottom housing 42 in a snap fit configuration such that each IR-reflective sphere 38 fits within a recessed pocket 54 within its respective sphere aperture 52. According to one implementation, bilateral shutters 36 are positioned over the housing 34 with tongues 70 sliding into cutouts 50 such that each shutter cover 68 obscures exactly one half of the IR-reflective sphere 38 (for example, the middle IR-reflective sphere 38) as depicted in FIG. 43.

Figure 44:
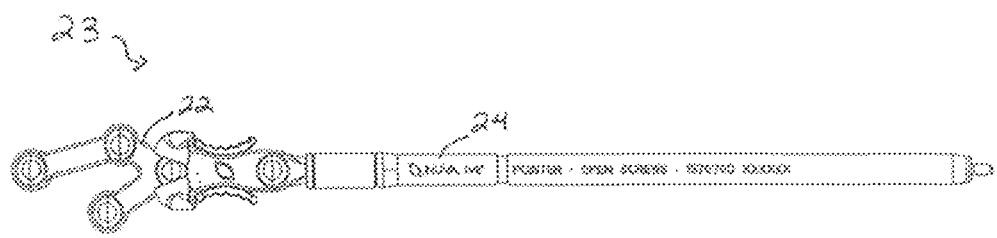
FIG. 44 is a front view of one embodiment of a digitizer pointer assembly comprising part of the system of FIG. 1.
Figure 45:
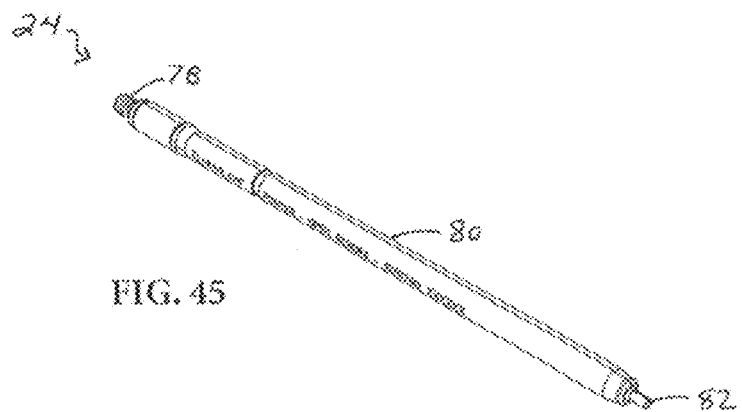
FIG. 45-48 are perspective views of various surgical pointers compatible with the digitizer array of FIG. 41.
Figure 46:
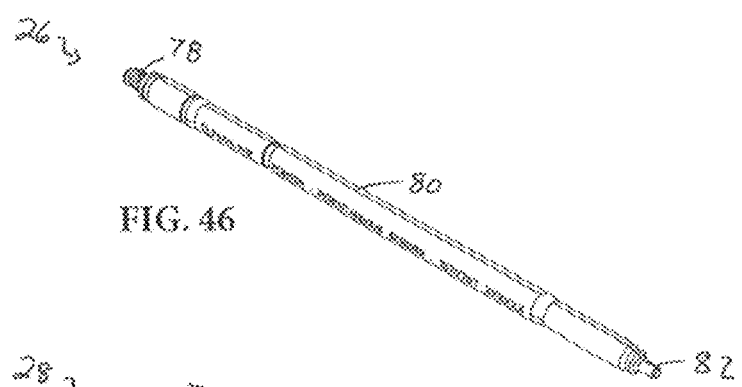
Figure 47:
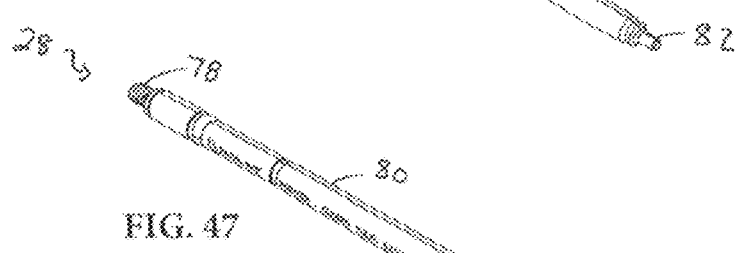
Figure 48:
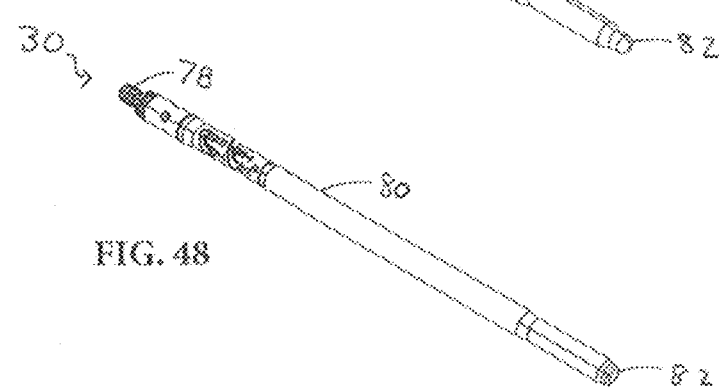

As depicted in FIG. 44, the IR-reflective tracking array 22 mates with one or more surgical objects (for example styluses 24, 26, 28, 30). Each stylus 24, 26, 28, 30 includes a threaded proximal end 78 for mating with the threaded distal aperture 56 of the IR-reflective tracking array 22, elongate shaft 80, and shaped distal tip 82. Shaped distal tip 82 may be any shape that is complimentary to, and fits securely within, the shape of a particular screw head. For example, FIGS. 45-48 show styluses 24, 26, 28, and 30 each with a different shaped distal tip designed to mate with different open screw systems, minimally-invasive screw systems, and closed tulip, iliac, and offset connector systems. The distal tip 82 is preferably inserted into each screw while orienting the digitizer pointer coaxial to that screw (or other fixation device).

According to some implementations (for example, the implementations shown with respect to styluses 24, 26, and 28), the length of the elongate shaft 80 is fixed relative to the array 22 such that all digitized points are a consistent length from the geometry of the IR-reflective markers 38 and position information may be obtained from this relationship. According to other implementations, the length of the elongate shaft 80 is adjustable relative to the array 22 such as that shown with stylus 30, effectively elongating the distance from the digitized point and the IR-reflective markers. This longer distance translates to digitization of a point above the actual screw head based on the distance the User adjusted the elongate shaft 80. As will be appreciated in conjunction with the discussion below, the resulting bend instructions would shape a rod that traverses that point above the screw allowing the User to reduce the screw to the rod.

In accordance with the present invention, there are provided a plurality of algorithms for achieving rod bends. The surgical bending algorithms may be divided into two smaller sub-systems: (1) the spatial location algorithms that acquire, collect, and digitize points in space and (2) the bending algorithms that analyze the points and calculate the bend instructions and rod length needed to bend a rod with the mechanical bending device 18. U.S. patent application Ser. No. 13/815,643, entitled "Systems and methods for performing spinal surgery" and filed on Mar. 12, 2013, the entire contents of which are hereby incorporated by reference as if set forth fully herein, describes such bending algorithms in details.

Figure 49:
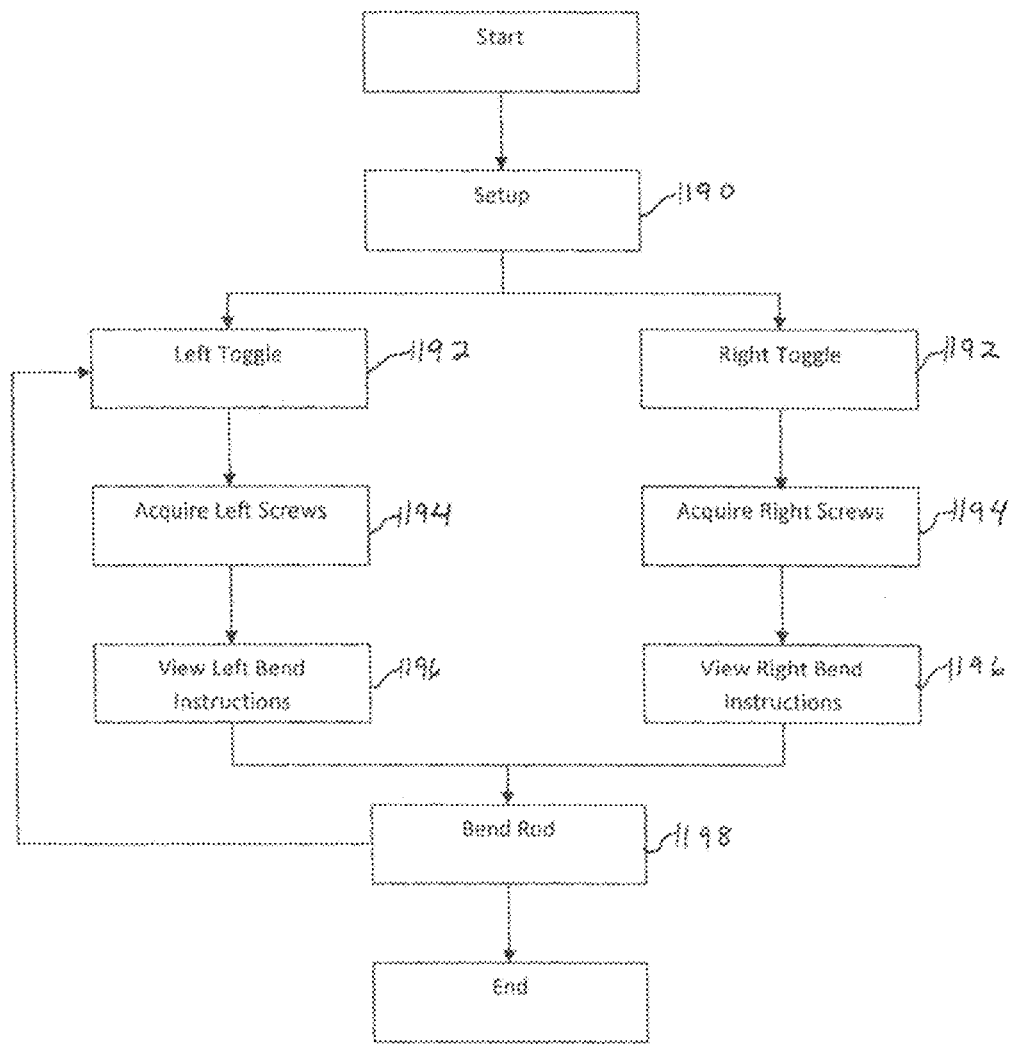
FIG. 49 is a flow chart depicting the rod bending workflow according to one embodiment.

Details of the system 10 are now discussed in conjunction with a first embodiment of a method for obtaining a custom-fit rod. The system 10 is typically utilized at the end of a posterior or lateral fixation surgical procedure after screws, hooks or other instrumentation have been placed, but prior to rod insertion. As shown in the flowchart of FIG. 49, the system 10 obtains position information of the implanted screw positions and outputs bend instructions for a rod shaped to custom-fit within those implanted screws. At step 1190, pertinent information is inputted into the system via a setup screen. At step 1192, the User designates the side for which a rod will be created (patient's left or right side). At step 1194, the system 10 digitizes the screw locations. At step 1196, the system 10 outputs bend instructions. At step 1198, the User bends the rod according to the bend instructions. Steps 1190-1198 may then be repeated for a rod on the contralateral side of the patient if desired.

Figure 50:
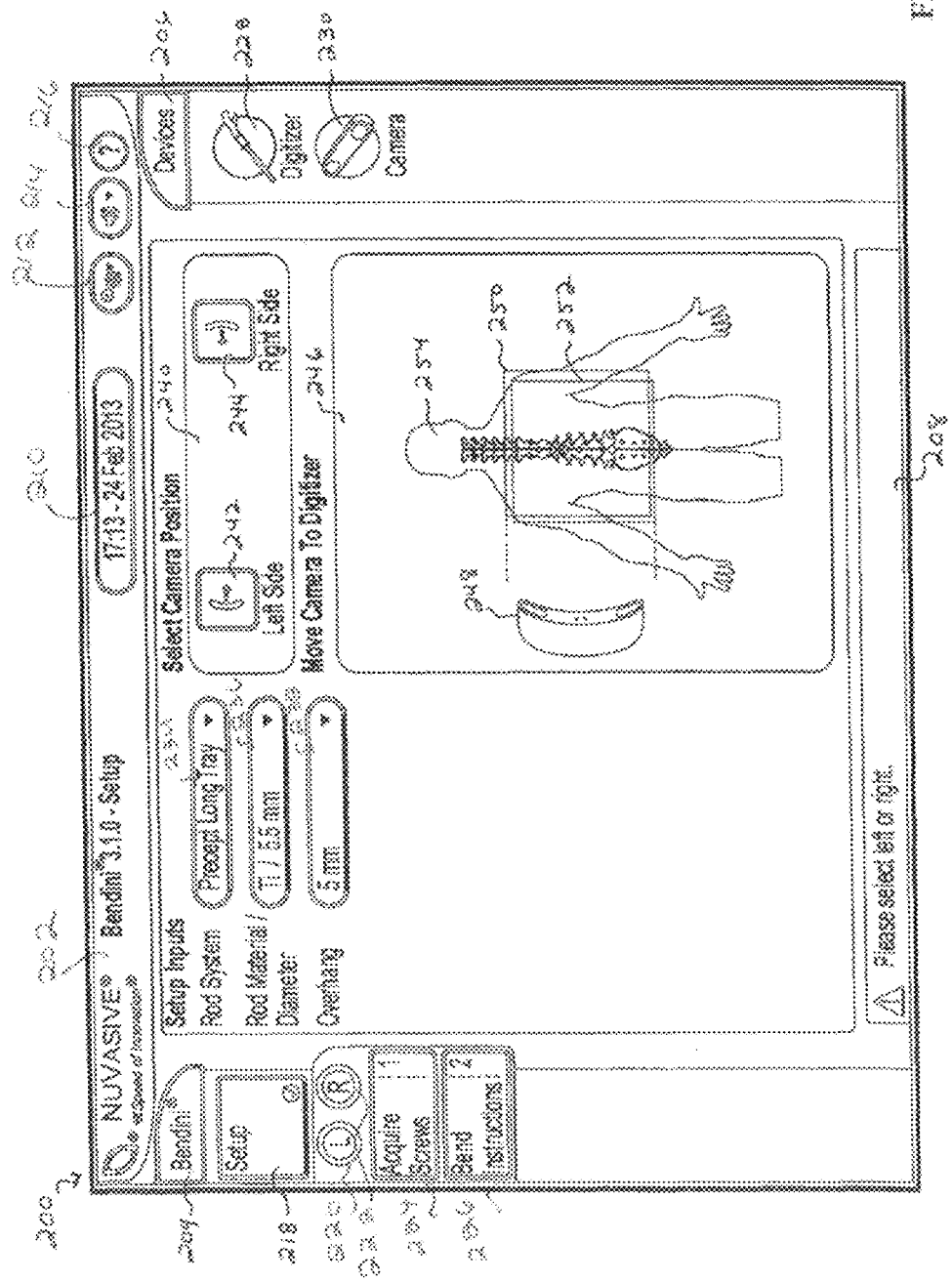
FIG. 50 is a screen shot illustrating an example setup screen according to one embodiment.

FIG. 50 illustrates, by way of example only, one embodiment of a screen display 200 of the control unit 16 capable of receiving input from a User in addition to communicating feedback information to the User. In this example (though it is not a necessity), a graphical User interface (GUI) is utilized to enter data directly from the screen display 200. As depicted in FIG. 50, the screen display 200 may contain a header bar 202, a navigation column 204, device column 206, and a message bar 208.

Header bar 202 may allow the User to view the date and time, alter settings, adjust the system volume, and obtain help information via date and time display 210, settings menu 212, volume menu 214, and help menu 216 respectively. Selecting the settings drop-down menu 212 allows the User to navigate to system, history, and shutdown buttons (not shown). For example, choosing the system button displays the rod bending software version and rod bender configuration file; choosing the shutdown option shuts down the rod bending software application as well as any other software application residing on the control unit 16 (e.g. a neuromonitoring software application); and choosing the history option allows the User to navigate to historical bend points/instruction data in previous system sessions as will be described in greater detail below. Selecting the help menu 216 navigates the User to the system User manual. As will be described in greater detail below, navigation column 204 contains various buttons (e.g., buttons 218, 220, 222, 224, 226) for navigation through various steps in the rod bending process. Pressing button 204 expands/minimizes the details of the navigation column. Devices column 206 contains various buttons indicating the status of one or more devices associated with the system 10. By way of example, devices column 206 may include button 228 for the digitizer 23 component of the system 10, respectively. Pressing button 206 expands/minimizes the details of the devices column. Furthermore, pop-up message bar 208 communicates instructions, alerts, and system errors to the User.

Upon selecting setup button 218 on the display screen 200, the system 10 automatically initiates the setup procedure. The system 10 is configured to detect the connection status of each of its required components. By way of example only, icon 228 indicates the connectivity and activity status of the digitizer 23. If one or more required components are not connected or are connected improperly, the display 200 may alert the User to address the issue before proceeding via textual, audio, and/or visual means (e.g., textual messages, audible tones, colored icons or screens, blinking icons or screens, etc.). According to one embodiment, the digitizer icon 228 is a status indicator for the active acquisition and/or recognition of the digitizer and the presence and background color of the icon 228 may change to indicate the digitizer tracking status. By way of example, the icon 228 may be absent when the system 10 is not acquiring screws and does not recognize the digitizer, gray when the system 10 is not acquiring screws and recognizes the digitizer, green when the system 10 is in screw acquisition mode and recognizes the digitizer, and red when the system 10 is in screw acquisition mode and does not recognize the digitizer. Pressing button 206 expands/minimizes the details of the device column 206. Depending on the type of surgery, type of patient deformity, etc., it may be advantageous for the User to choose a digitizer from a selection of different digitizers. According to one embodiment, pressing the stylus icon (not shown) expands a pull-out window for the different stylus options available with the system 10 (e.g., styluses 22, 24, 26, 30 as described above).

With all of the required components properly connected to the system 10, the User may then input one or more pieces of case-specific information from one or more drop-down menus. By way of example, drop-down menus for rod system 234, rod material/diameter 236, rod overhang 238, procedure type (not shown), and anatomical spinal levels of the surgical procedure) may be accessed from the setup selection panel 232 of the screen display 200. The rod system drop-down menu 234 allows the User to choose the rod system he/she plans to use. This selection drives choices for the rod material/diameter 236 drop-down menus. By way of example, under the rod system drop-down menu 234, the system 10 may be programmed with numerous fixation options from one or more manufacturers. Alternatively, it may be programmed with the fixation system selections for one manufacturer only (e.g. NuVasive® Reline™, Precept®, Armada®, and SpherX® EXT). The User may also choose the combination of rod material (e.g. titanium, cobalt chrome, etc.) and rod diameter (e.g. 6.5 mm diameter, 5.5 mm diameter, 3.5 mm diameter). The drop-down menu 238 for material and diameter options may preferably be dependent upon the choice of rod system. Because the geometry and sizes can vary between manufacturers and/or rod systems, programming the system 10 with these specific inputs can aid in outputting even more accurate bend instructions. The User may also choose the amount of overhang from the rod overhang pull-down menu 238. By way of example, the amount of overhang may be selectable in 0 mm, 2.5 mm, 5 mm, 7.5 mm, and 10 mm lengths. According to one embodiment, this function prescribes a symmetric overhang on both the superior and inferior ends of the rod. According to another embodiment, this function also prescribes different overhang lengths on either end of the rod based on User preference and patient anatomical considerations. The system 10 also contains functionality for accommodating multiple rod diameters, 5.5 mm to 3.5 mm transitional rods, and hinged rods as used, for example in Occipital-Cervical-Thoracic (OCT) fusion procedures.

After the setup inputs have been inputted into the setup selection panel 232, the system 10 aids the User in setting up the IR sensor 20 in an optimal position for positional data acquisition. It is to be appreciated that any visual (textual, graphic) indicator may be used to indicate the IR sensor placement instructions. According to some implementations, an active graphic directs the User to position the IR sensor 20 relative to the digitizer array 22 held static within the patient's body. As shown in FIG. 50, the User first selects the side of the patient the IR sensor 20 is located on by selecting the left side sensor position button 242 or right side sensor position button 244 in the IR sensor setup panel 240. Choosing the left or right side sensor position button 242, 244 activates a the IR sensor positioning panel 246 such that sensor graphic 248 and a tracking volume box graphic 250 appear on the display screen 200. Tracking volume box 252 that moves with the sensor graphic 248 as the IR sensor 20 is moved. Next, the User positions the digitizer array 22 into the body of the patient. Once recognized by the system 10, a target volume box 252 (which may be displayed as white in color) is positioned over the patient graphic 254. Next, the User moves the IR sensor 20 relative to the digitizer array 22 until the tracking volume box 250 matches up to the position of the target volume box 252. According to some implementations, the sensor graphic 248 increases in size if it is moved superior to the target tracking volume and decreases in size if it is moved inferior to the target volume. According to some other implementations, the tracking volume box 250 may be color-coded to depict the relative distance to the target volume. By way of example, the tracking volume box 250 may be depicted in red if the distance to the target volume is outside of a certain distance in one or more axes (e.g., outside±8 cm in all 3 axes.) and green if within or equal to ±8 cm in all 3 axes. Once the optimal position of the IR sensor 20 has been ascertained, the setup process is complete.

Figure 51:
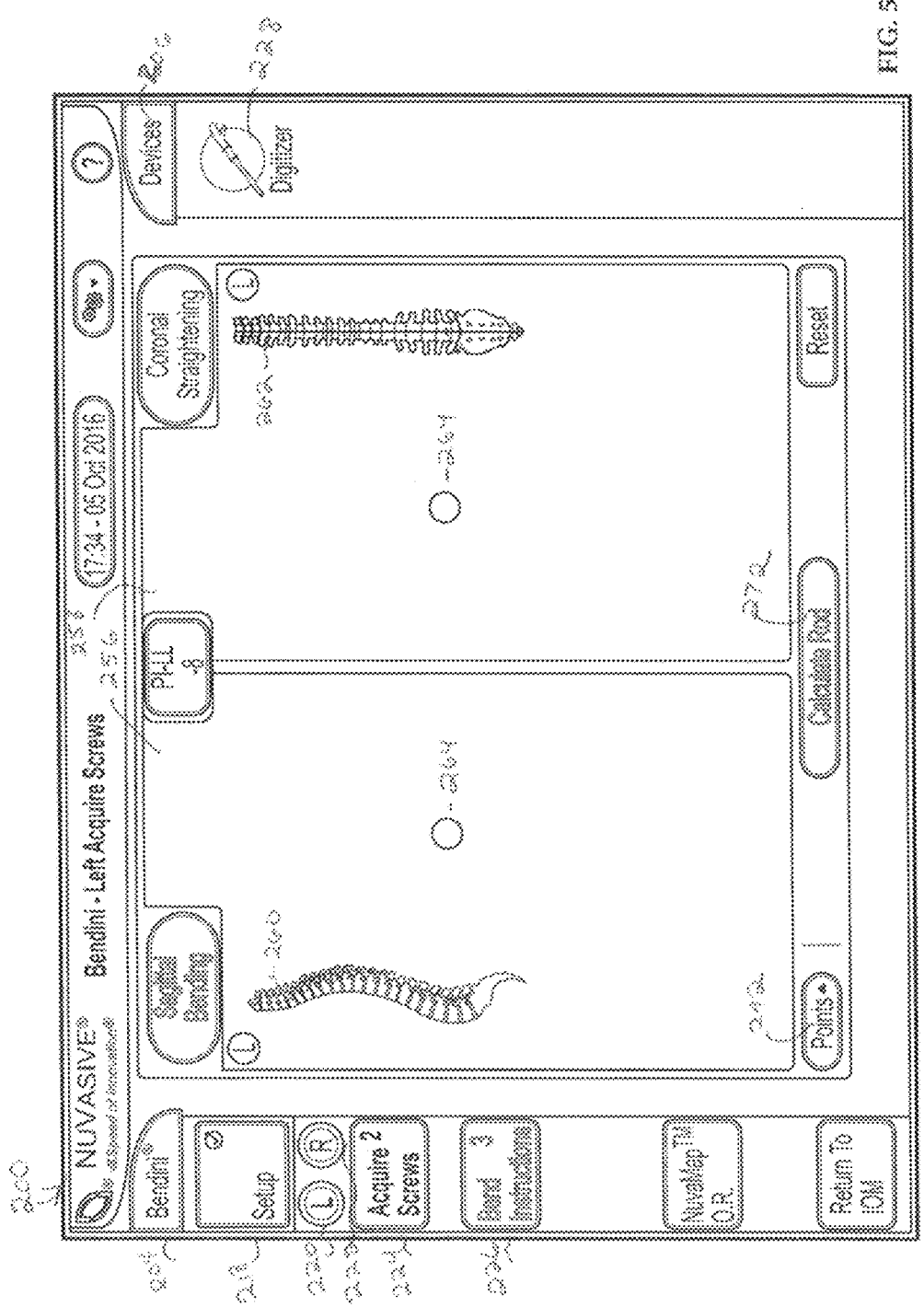
FIG. 51-52 are screen shots illustrating an example of the screw acquisition screen according to one embodiment.
Figure 52:
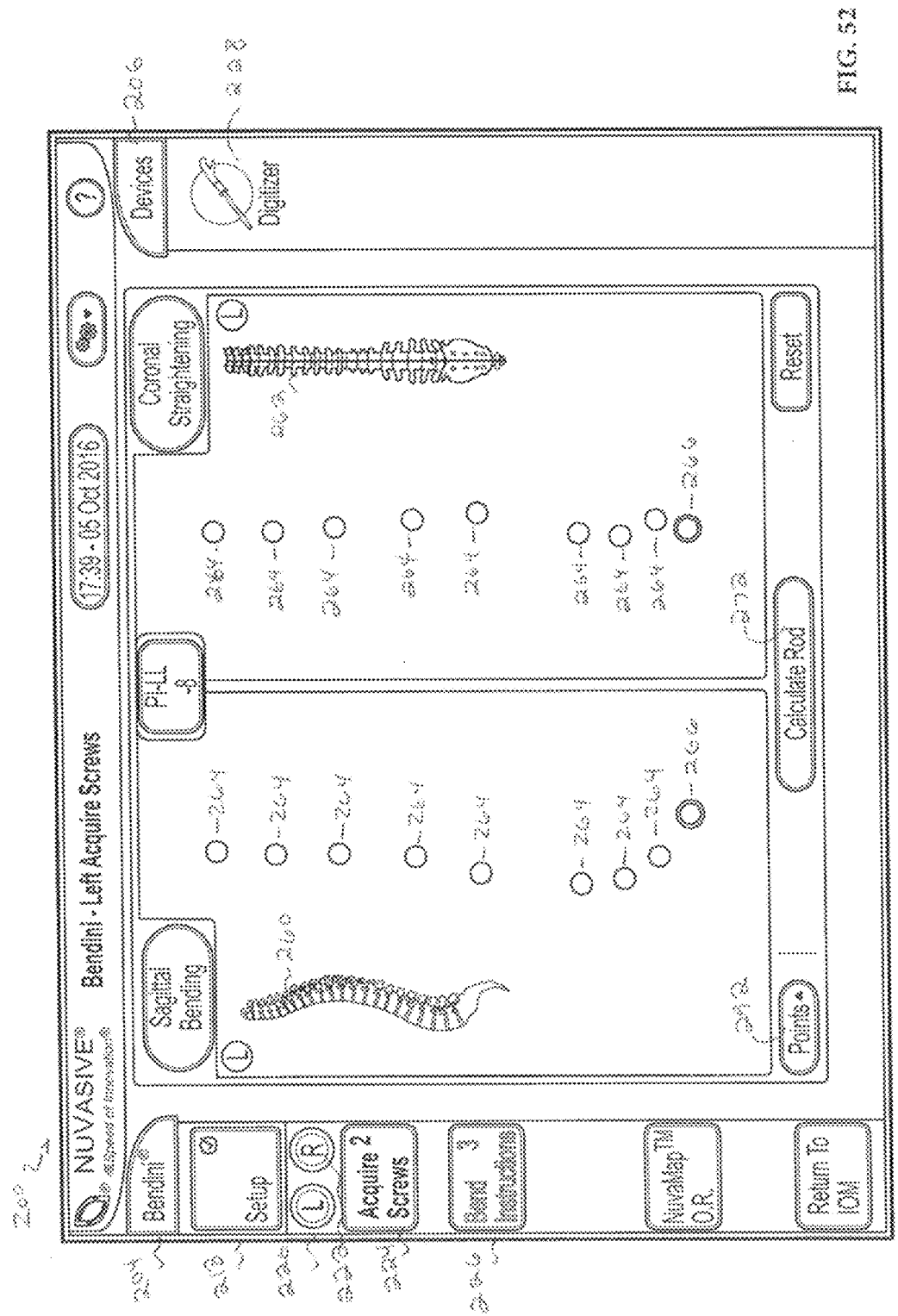

Once the User has completed all of the required steps in the setup screen, a graphic (e.g., a check) may appear on setup button 218 to indicate such a completion and the system 10 proceeds to step 1192 in the flowchart of FIG. 49. Using the GUI, the User designates which side of the patient's spine to acquire digitized positional information from by selecting either the Left "L" toggle/status button 220 or Right "R" toggle/status button 222. The User then selects the Acquire Screws button 224 which navigates the display screen 200 to an Acquire Screws (left or right) screen shown by way of example in FIGS. 51-52. In Acquire Screws mode, the display screen 200 includes a sagittal view panel 256 and a coronal view panel 258 with spine graphics 260, 262 in each of the sagittal and coronal views, respectively. Spine graphic 260 may flip orientation depending on which side of the spine the User is digitizing (left or right). Additionally, spine graphic 262 may highlight the side of the patient the User is digitizing (left or right). The User may digitize the location of each implanted screw using, by way of example, the digitizer pointer 23 as described above. As each screw point 264 is digitized, its relative location with respect to the other acquired screw points 264 can be viewed in both sagittal and coronal views via the sagittal view panel 256 and the coronal view panel 258 as shown in FIG. 52. Optionally, the last screw point digitized may have a different graphic 266 than the previously-acquired screw points 264 (by way of example, the last screw point acquired 266 may be a halo and the previously-acquired screw points 264 may be circles). The screws locations may be digitized from a superior-to-inferior or inferior-to-superior direction and according to some embodiments, the system 10 can detect which direction the digitization is occurring in after the acquisition of two consecutive screw point locations. If during the digitization process, the User wishes to delete a digitized screw point, he/she may do so by pressing the "Clear Point" button (not shown) under the Points menu 292. If the User wishes to delete all digitized screw points, he/she may do so by pressing the "Clear All Points" button (not shown).

Figure 53:
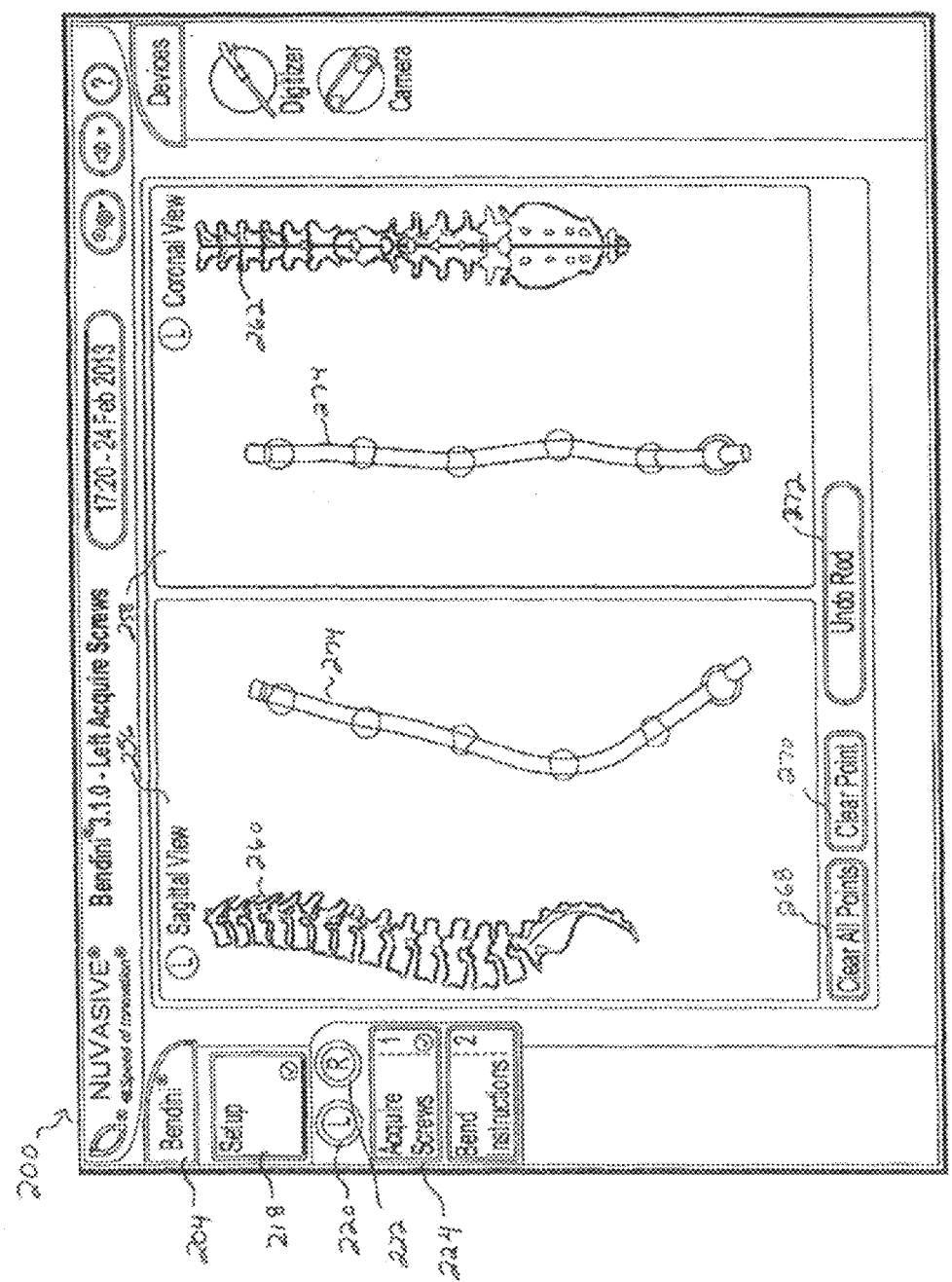
FIG. 53 is a screen shot illustrating an example of the rod preview screen according to one embodiment.
Figure 54:
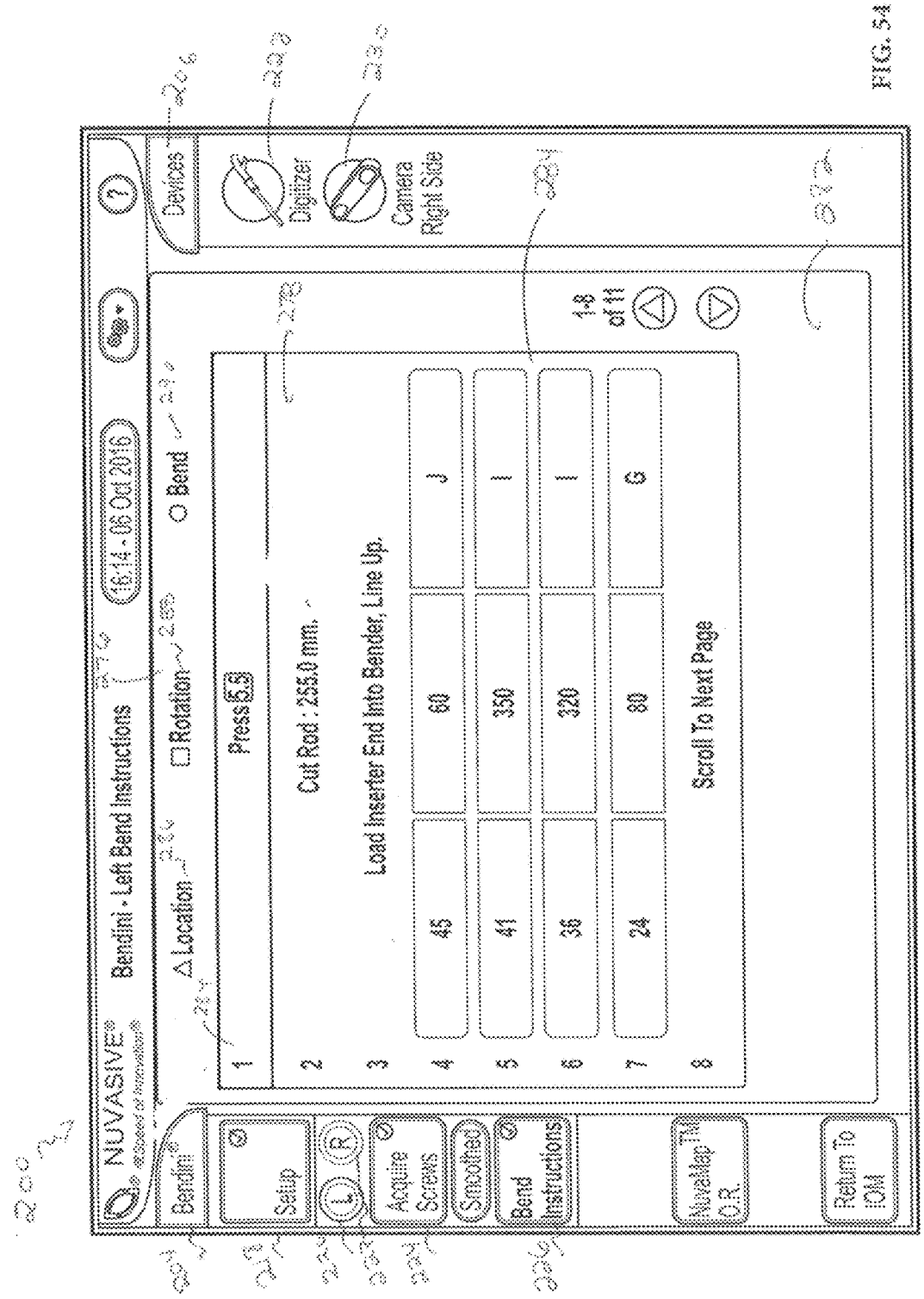
FIG. 54 is a screen shot illustrating an example rod bending instruction screen according to one embodiment.

Once the digitized screw points 264 are deemed acceptable, the User may press the "Calculate Rod" button 272 which initiates the curve calculation preferably using one of the algorithms discussed in U.S. patent application Ser. No. 13/815,643, entitled "Systems and methods for performing spinal surgery" and filed on Mar. 12, 2013, the entire contents of which are hereby incorporated by reference as if set forth fully herein. As shown for example in FIG. 53, once a rod solution has been calculated, a rod graphic 274 populates through the screw points 264, 266 and a confirmation graphic (e.g., a check) may appear on the "Acquire Screws" button 224 to indicate that the system 10 has generated a rod solution. Simultaneously, the "Calculate Rod" button 272 becomes the "Undo Rod" button 272. If the User presses the "Undo Rod" button 272, the rod solution 274 is cleared and the User may acquire more screw points or clear one or more screw points. After the "Undo Rod" button 272 is pressed, it then changes back to the "Calculate Rod" button 272. Optionally, the system 10 may include a visual graphic for where along a rod the curve calculation is generating a severe bend (acute angle). The User may select "Undo Rod" button 272, perform one or more surgical maneuvers (e.g. reduce the screw, backup the screw, adjust the screw head, etc.), re-digitize the screw point, and generate a more feasible solution. As shown in FIG. 54, if the rod solution is acceptable to the User, the Screw Acquisition step 1194 is complete and the system 10 proceeds the Bend Instructions step 1196 in the flowchart of FIG. 49. Alternatively, although not shown the system 10 may display the offending point resulting in the severe bend angle in red and offer the next-best solution that includes a bend angle falling within a pre-determined range of angles for that bender. If the rod solution is acceptable to the User, the Screw Acquisition step 1194 is complete and the system 10 proceeds the Bend Instructions step 1196 in the flowchart of FIG. 49.

The User then selects the "Bend Instructions" button 226 which navigates the display screen 200 to a Bend Instructions (left or right) screen shown by way of example in FIG. 54. The bend instructions within the bend instructions panel 276 allows the User to view the bend instructions corresponding to the resulting rod solution in the Acquire Screws screen. By way of example, the bend instructions panel 276 contains three fields containing various aspects of the bending instruction: upper message field 278, bender instructions field 280, and lower message field 282. By way of example, the upper message field 278 may communicate the rod cut length, rod type, and/or rod loading instructions to the User (e.g. "Cut Rod: 255.0 mm Load Inserter End Into Bender, Line Up"). The bender instructions field 280 displays rows 284 of bend maneuvers in location 286, rotation 288, and bend angle 290 to perform on the mechanical bender 18 as will be described in greater detail below. In the example shown in FIG. 54, there are four rows indicating four bend instructions. The lower message field 282 may communicate the direction of insertion or orientation of implanting the rod to the User. For example, in some bend instructions the lower message field 282 may for example provide the following sample instruction: "Insert Rod head to foot." In some implementations, the rod insertion direction into the patient is dependent on the sequence of screw digitization (superior-to-inferior or inferior-to superior). According to one or more preferred embodiments, the bend instruction algorithm takes into account the orientation of the inferior, superior, anterior, and posterior aspects of the rod and ensures that these aspects are known to the User. As the instructions for use direct the User to load the rod into the bender, the system 10 manages which bends are imparted on the rod first based on the severity of the bend angles. The section of the bend instructions with greater bend angles may be performed first then the straighter bend sections of the bend instructions may be performed last. Further, the instructions may also direct the User to align a laser line or orientation line on the rod to an alignment arrow (not shown) on the mechanical rod bender 18. This alignment controls the Anterior/Posterior orientation of the rod geometry and generates bend instructions accordingly. The User follows the bend instructions generated by the system 10 for location (location may be color-coded on the bender 18 and on the screen 200 as green triangle), rotation (rotation may be color-coded on the bender 18 and on the screen 200 as red circle), and bend angle (bend angle may be color-coded on the bender 18 and on the screen 200 as blue square), sequentially, starting at the first bend instruction and working sequentially until the final bend is completed. From here, the User may repeat steps 1190-1198 on the rod construct for the contralateral side of the patient's spine.

Within a surgical procedure, a User may wish to toggle between left and right screens to view left and right digitized screw points, rod previews, and bend instructions for reference or comparison. Selecting the Left "L" toggle/status button 220 and right "R" toggle/status button 222 allows the User to do so. According to one more implementations, the GUI may additionally include a History feature. Selecting the History button (not shown) will allow the User to refer back to any previous rod bending solution. The User navigates to the Bend Instructions screen 226 based on choice of the L/R toggle buttons 220, 222 and pressing the Bend Instruction button 226. If navigating to previous bend instructions, the Bend Instructions screen will display previous bend instructions. Once the User has selected the desired rod solution, the User then executes the bends using the mechanical bender 18.

Figure 55:
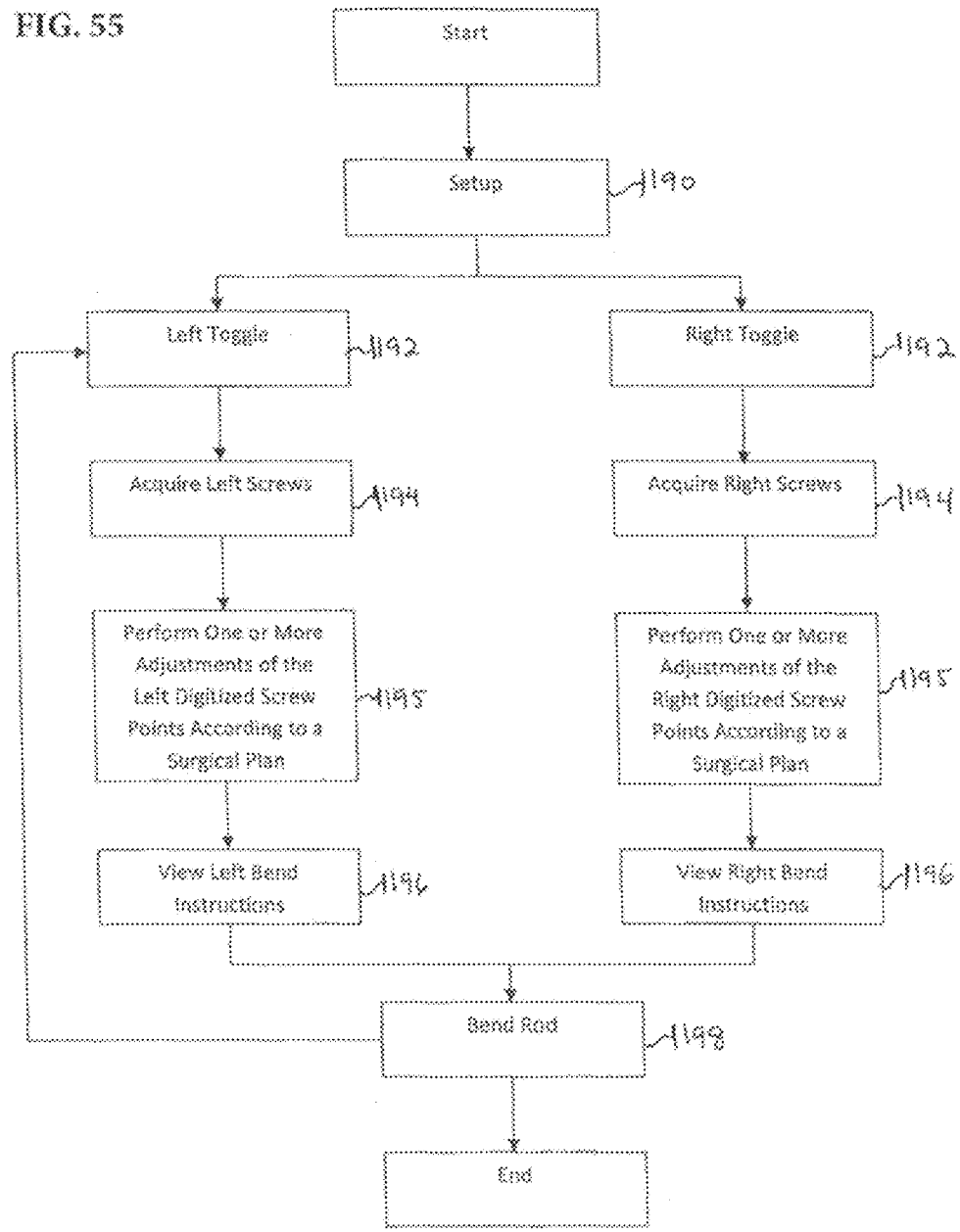
FIG. 55 a flow chart depicting the rod bending workflow according to another embodiment.

The embodiments described with respect to FIGS. 51-54 above contemplate digitizing the implanted screw positions and outputting bend instructions for a rod shaped to custom-fit within those implanted screws. In one or more additional embodiments, the system 10 obtains position information of the implanted screws (steps 1192 and 1194), accepts correction inputs via one or more advanced options features (step 1195), and generates for viewing bend instructions for a rod shaped to fit at locations apart from those implanted screw positions (step 1196) as depicted in the flowchart of FIG. 55. Installing a rod shaped in this manner could correct a curvature or deformity in the patient's spine according to a User's prescribed surgical plan. Details of the system 10 are discussed now discussed with examples for obtaining a rod bent according to one or more surgical plans.

Figure 56:
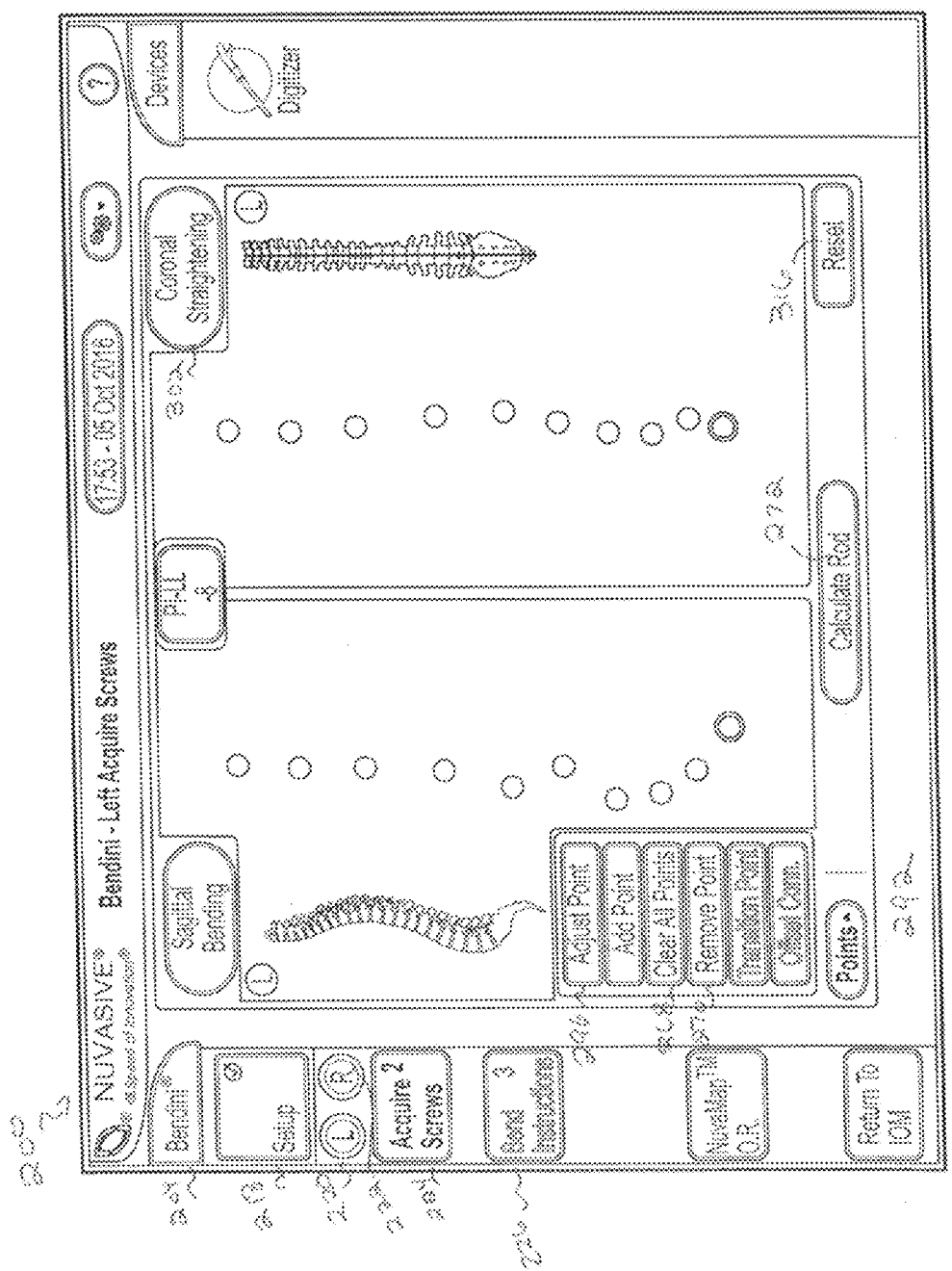
FIG. 56 is a screen shot illustrating an example of the Points adjustment menu screen according to one embodiment.

As depicted in FIG. 56, selecting the "Points" button 292 expands a menu from which the User may perform one or more corrections to the digitized screw points and the system 10 generates bend instructions that will achieve those desired corrections on the patient's spine once the rod is implanted and the screws are brought to the rod.

Figure 57:
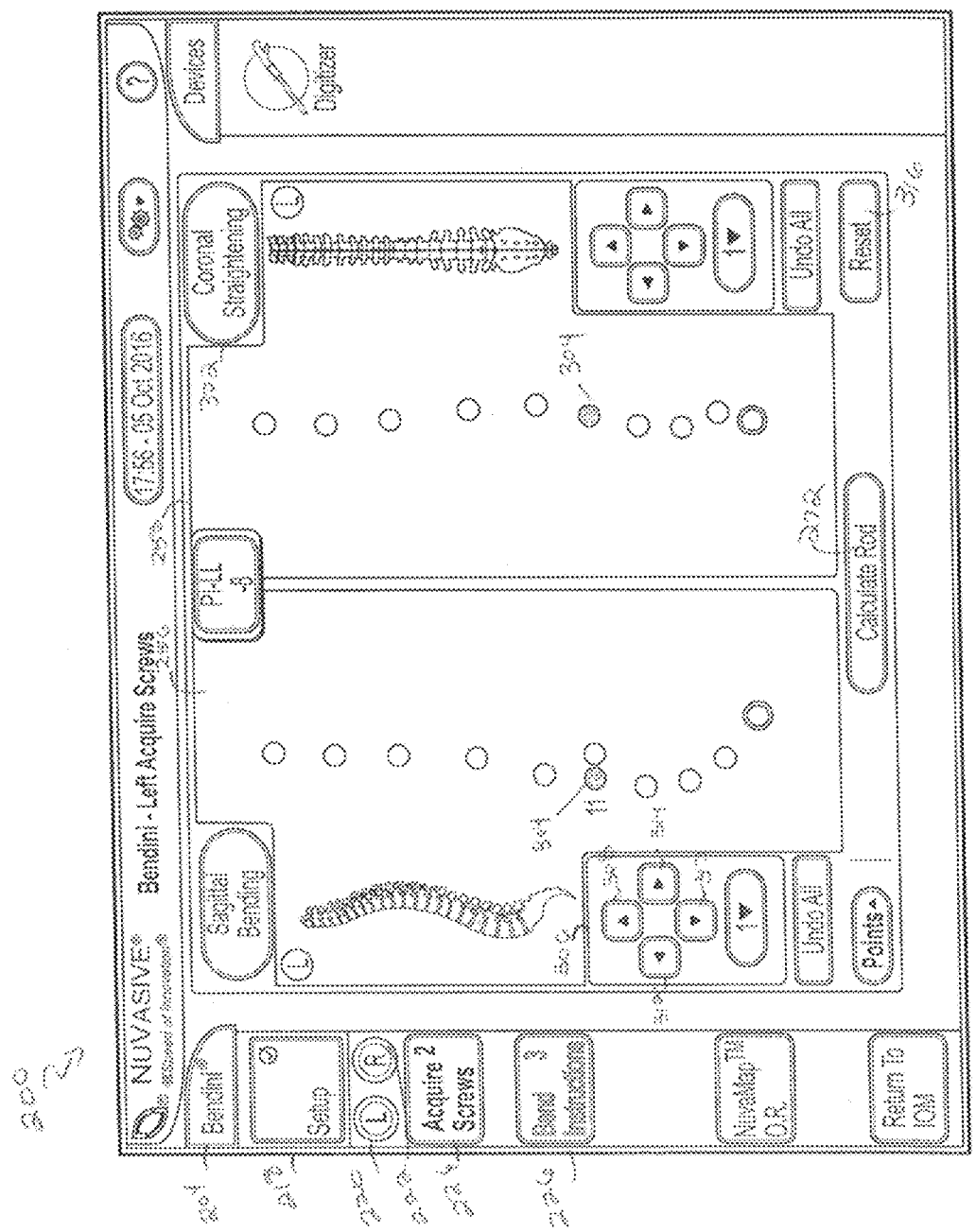
FIG. 57 is a screen shot illustrating an Points Adjustment screen according to one embodiment.
Figure 38:
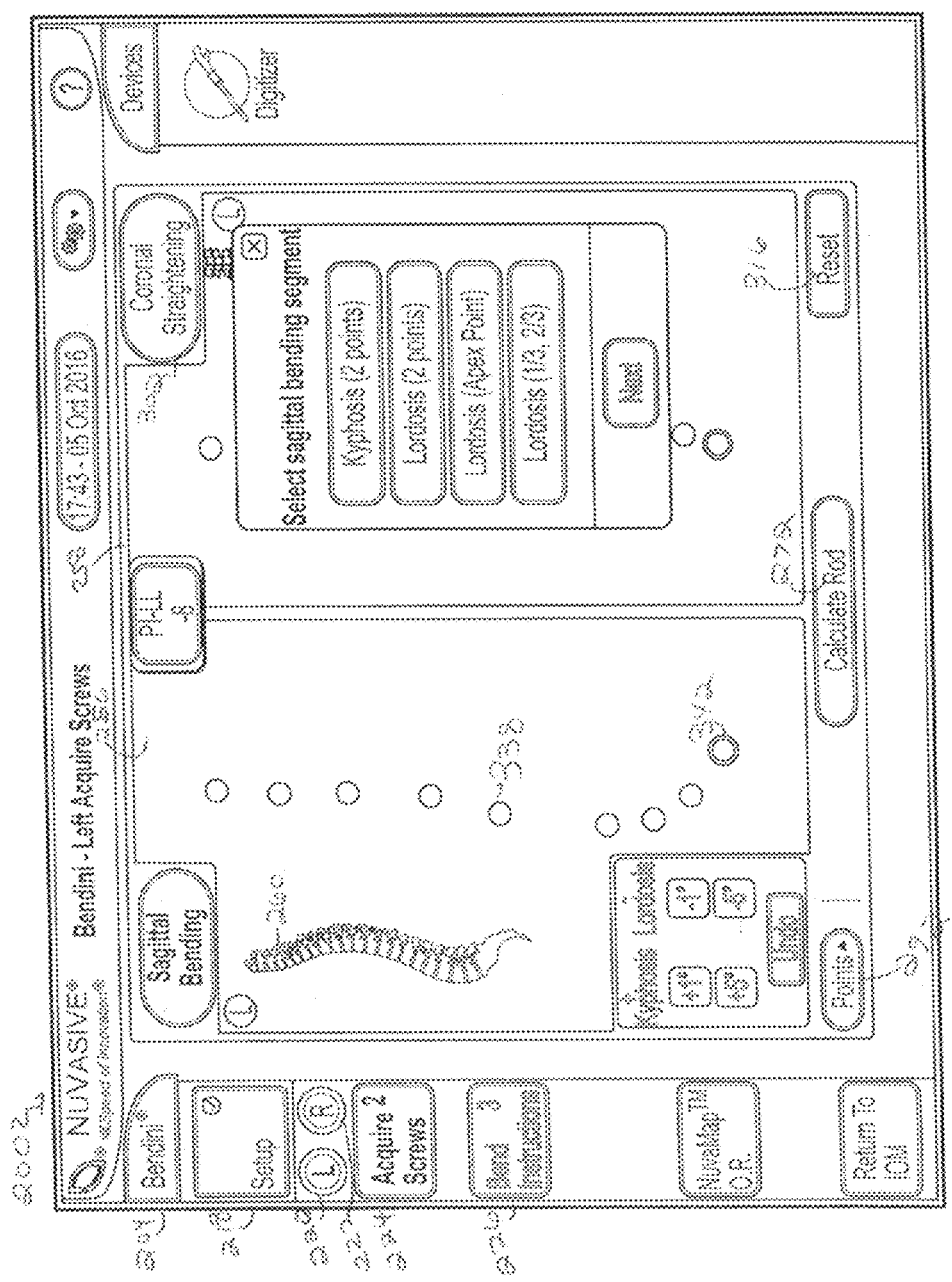

In some surgical procedures, a User may wish that the rod bend solution will consider a point that is not a digitized screw point in determining the bend instructions. According to some implementations, this point is an adjusted distance from the digitized screw point location. Selecting the "Adjust Points" button 296 from the Points menu 292 navigates the User to an Adjust Points screen as depicted in FIG. 57. Selecting a digitized screw location of interest (for example the screw point represented as dot 304 in FIG. 57) highlights the screw point and brings up an adjust points control 306 in each of the sagittal and coronal views 256, 258. The User adjusts point 304 to its desired location in the sagittal and coronal planes using arrows 308, 310, 312, and 314. In some implementations, as the point moves, dot 304 changes color based on the distance from the originally digitized screw location as shown in FIG. 57. In some embodiments that color corresponds to color-coded offset distance indicator (not shown) which provides visual feedback to the User as to the distance the point has been adjusted. In some implementations, the system 10 may have a maximum distance from the digitized point past which it will not allow the manipulated point to exceed (by way of example only, this distance may be 5 mm). In other implementations, this distance may be depicted as a distance (for example, the numeral 11 in FIG. 57, indicating that a screw point is 11 mm from its original location). The User may adjust as many points as desired in this fashion. The User may reset all adjusted points to their original configurations via "Reset" button 316. Once satisfied with the adjusted points, the User may either proceed to one or more additional advanced options as set forth below or select "Calculate Rod" 272. Once "Calculate Rod" 272 has been selected, the system 10 generates a rod in which the curve traverses the adjusted points, thereby creating a correction-specific rod and providing the User with the ability to correct the curvature or deformity in the spine according to his or her prescribed curve.

In some instances, a User may want to align or correct the patient's spine in the sagittal plane (i.e., add or subtract lordosis or kyphosis). The system 10 includes a sagittal correction feature in which the User is able to measure the amount of lordosis in the spine and adjust angles in the sagittal plane. The system 10 then incorporates these inputs into the bend algorithm such that the rod solution includes the desired alignment or correction.

Figure 59:
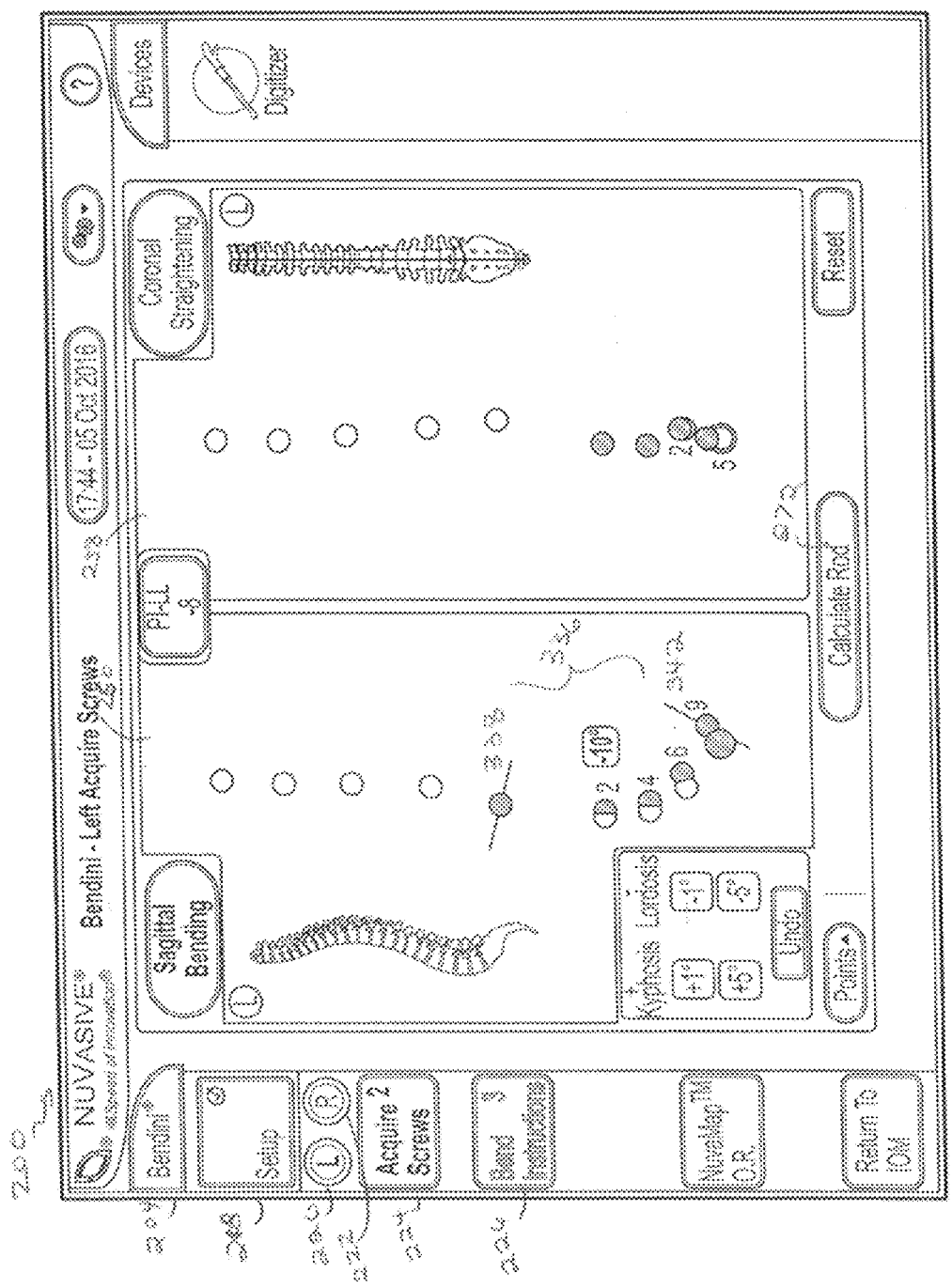
Figure 60:
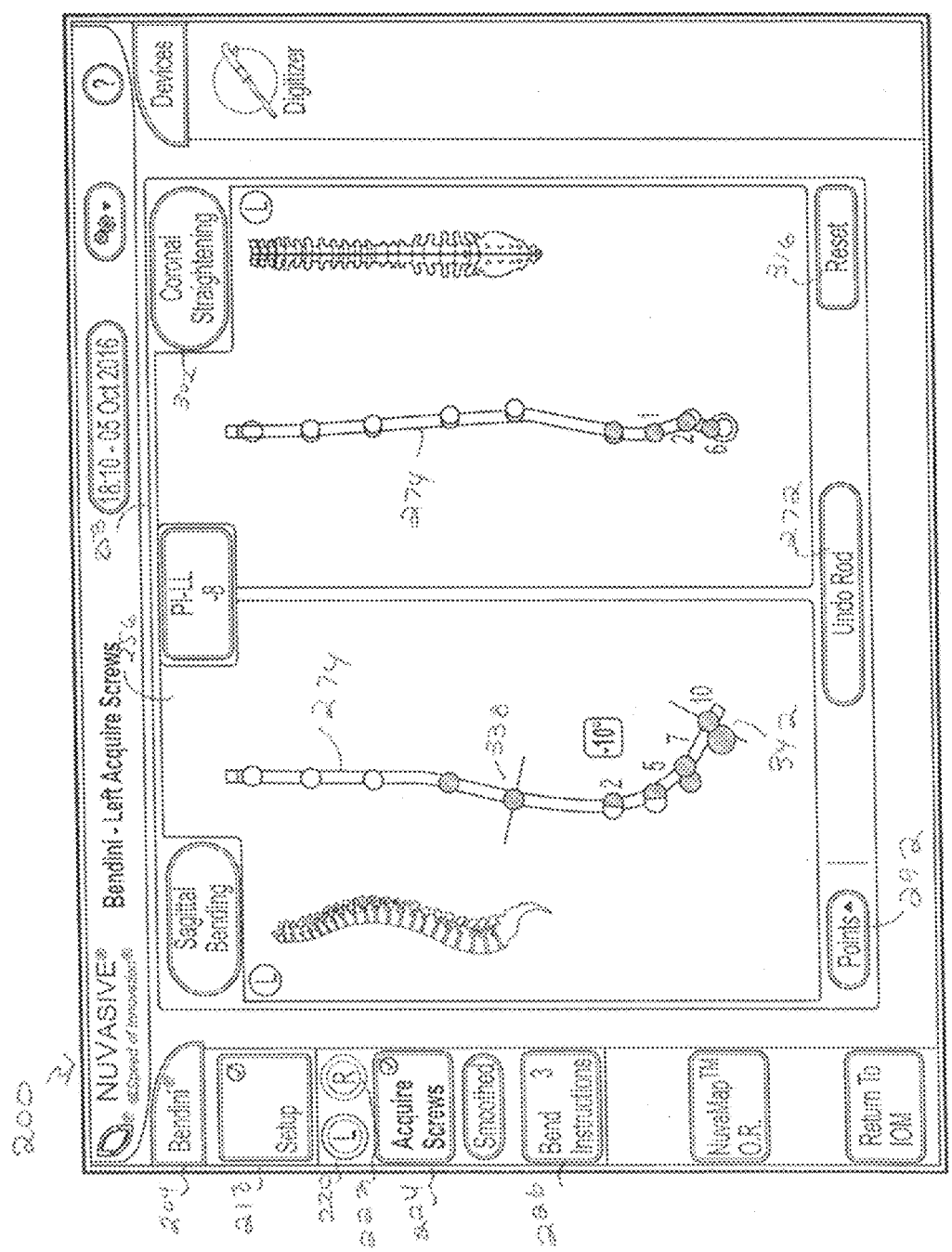
FIG. 60 is a screen shot illustrating an example of the rod preview screen with lordosis correction according to one embodiment.

Selecting the "View Vectors" button (not shown) from the Advanced Options menu (not shown) initiates the sagittal correction feature as shown in FIG. 58. The User may select at least two points of interest and the system then determines the appropriate vector in the sagittal view. According to the embodiment shown in FIGS. 59-60, the angles are measured and adjusted based on the screw trajectory screw axis position) using the digitized screw data acquired in the Acquire Screws step 1194. As shown in FIG. 59, the User selects at least two screw points of interest (e.g., screw points 338 and 342). The system 10 then measures the angle between the screw trajectories. In some implementations, the system 10 may measure the total amount of lumbar lordosis by measuring the lumbar lordosis angle 334 in the superior lumbar spine and the lumbar lordosis angle 336 in the inferior lumbar spine. Using the angle adjustment buttons 328, 330 on the Angle Adjustment Menu 326, the User may increase or decrease the desired angle correction of the spine in the sagittal plane (i.e., add or subtract lordosis or kyphosis superiorly or inferiorly). As the angle is adjusted, the angular position 336 between the two screw points 338, 342 is changed as well. The system 10 may include a color-coded offset distance indicator 322 to provide the User with an indication of the distance each digitized screw position will be adjusted in the sagittal plane as described above. Once the desired amount of angular correction is achieved, the User may select the "Calculate Rod" button 272. The system 10 then displays a rod solution 274 incorporating the User's clinical objective for correction of the spine in the sagittal plane as depicted, for example, in FIG. 60.

According to one embodiment of the sagittal correction feature, the superior and inferior lumbar lordosis angles 354, 356 are measured, displayed, and adjusted referencing anatomy from an imported lateral radiographic image (not shown).

It is to be appreciated that, because patient position may have an effect on the cervical and lumbar lordosis measurements, the sagittal correction feature of the system will be able to account for any patient positioning-related deviations. It will also be appreciated that in addition to lordotic corrections, the sagittal angle assessment tool may be useful for other types of surgical maneuvers, including but not limited to pedicle subtraction osteotomy (PSO) procedures and anterior column reconstruction (ACR) procedures.

In some instances, a User may want to align or correct the patient's spine in the coronal plane (i.e., correct scoliosis). The system 10 includes one or more coronal correction features in which the User is able to view the patient's spine (and deformity) in the coronal plane via anterior-posterior x-rays; measure one or more anatomic reference angles; and/or persuade one or more screw locations towards a particular coronal alignment profile by manually or automatically biasing which direction the rod bend curve is adjusted. The system 10 may then incorporates these inputs into the bend algorithm such that the rod solution includes the desired alignment or correction.

Selecting the "Coronal Straightening" button 302 initiates the coronal correction feature. The User may wish to ascertain the degree of coronal deformity by referencing spinal anatomy, measuring the coronal Cobb angles between two anatomical references in the coronal plane, and adjusting those angles intraoperatively as part of the surgical plan to bring the spine into (or closer to) vertical alignment.

Figure 61:
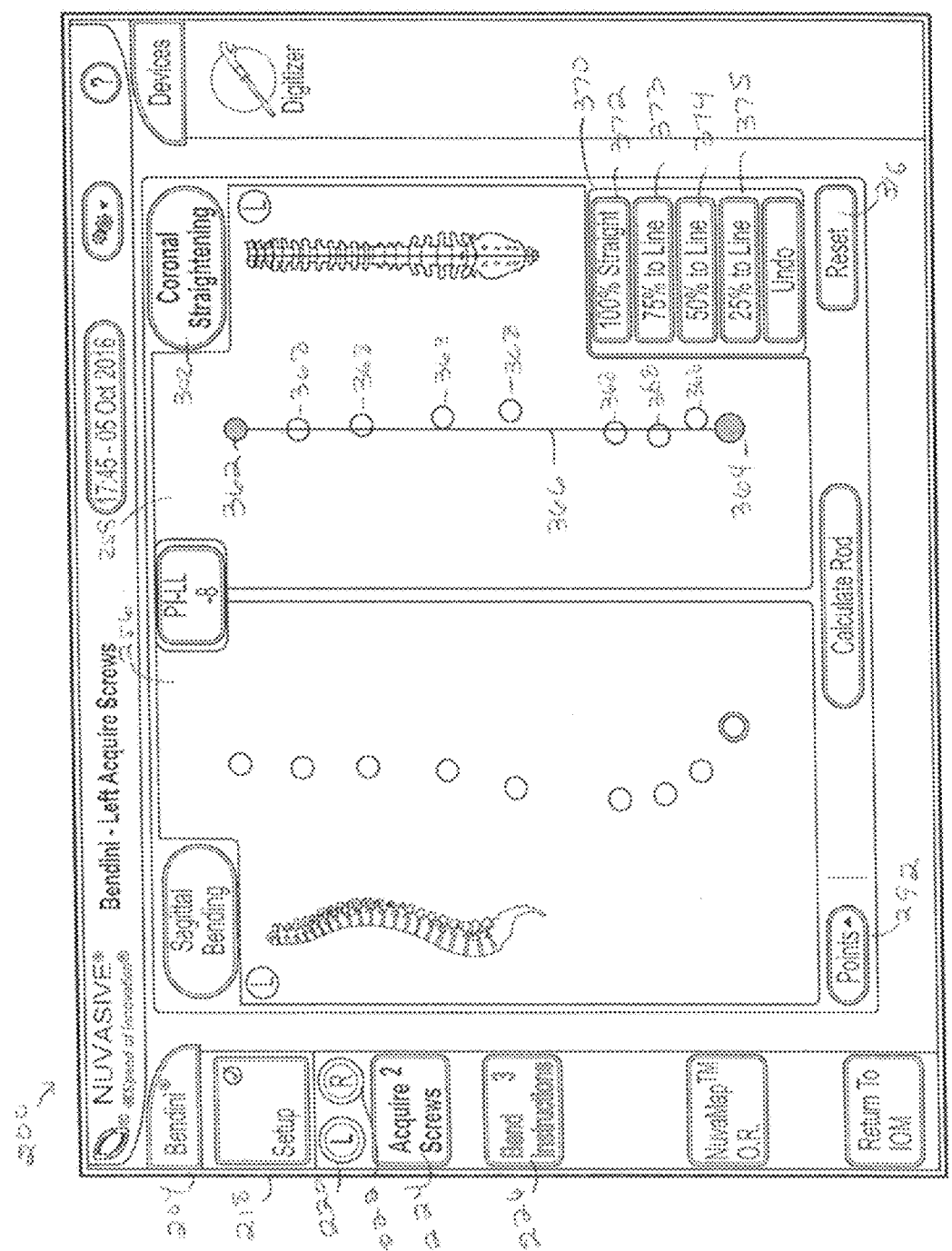
FIGS. 61-62 are screen shots illustrating an example Coronal Straightening screen according to one embodiment.

According to one or more other implementations of the coronal correction feature, as shown in FIG. 61, the User may select at least two points of interest and the system then generates a best fit reference line through all points including and lying between the at least two points of interest. In some instances, the ideal correction of the spine in the coronal plane is a straight vertical line extending between the superior-most and inferior-most screw locations of interest. However, depending on a patient's individual anatomy, achieving a straight vertical line may not be feasible. The User may wish to achieve a certain amount of correction relative to the ideal correction. From the display screen, the User may select a percentage of relative correction between the screw points as digitized 25%, 50%, 75% or 100% correction to the best fit reference line. Furthermore, the system then calculates a rod solution and shows an off-center indicator 322 to provide a User with an indication of the distance each screw is from the coronally-adjusted rod construct as set forth above.

Figure 62:
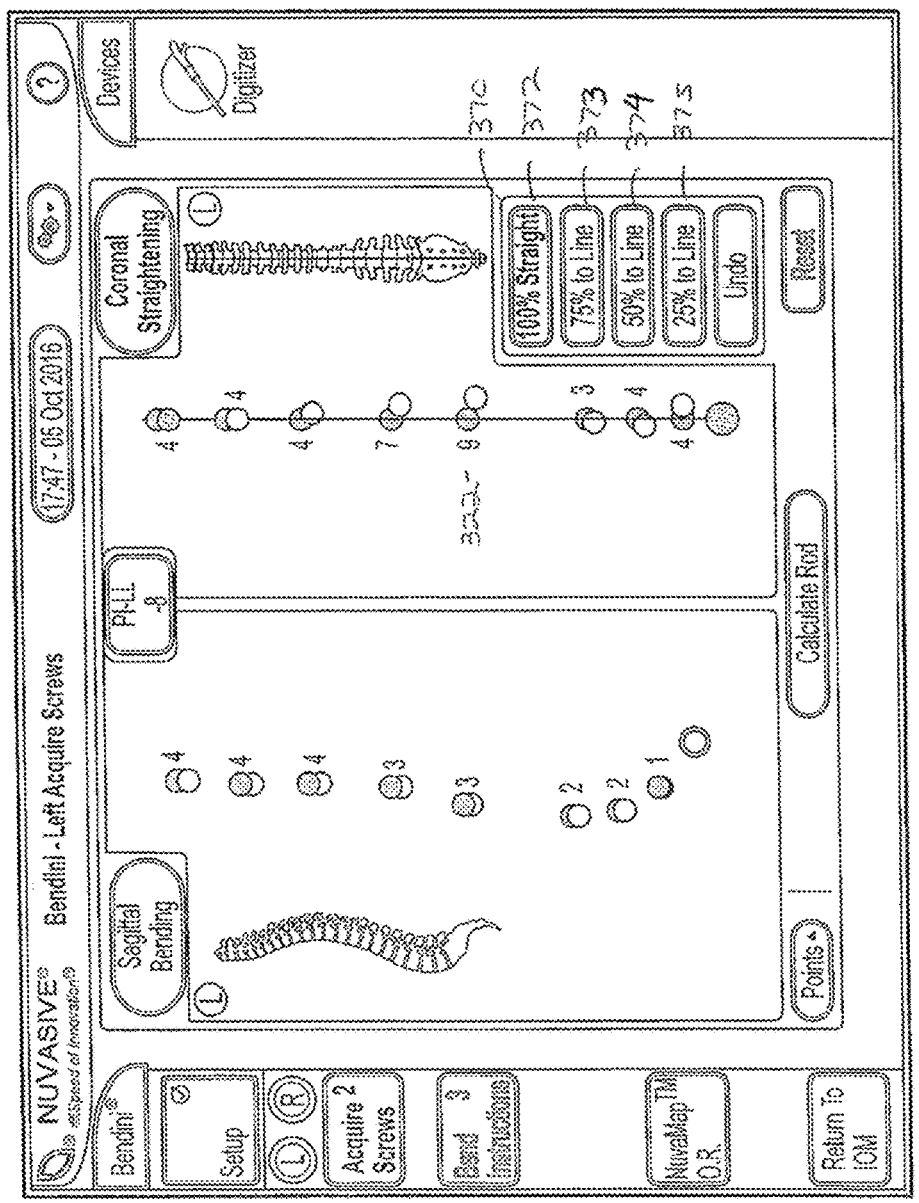

According to the embodiment shown in FIGS. 61-62, the User may straighten all points within the construct (global coronal correction). From the display screen 200, the superior and inferior screw points 362, 364 are selected and the system 10 generates a best fit global reference line 366 through all points 362, 364, 368. Using the Coronal Straightening Menu 370, the User selects the degree of correction desired 372, 373, 374, 375 to adjust the percentage of correction desired. In the example shown in FIG. 62, the amount of desired correction is shown as 100% on the percentage correction indicator 372, meaning the rod solution 274 will be a straight line in the coronal plane and all screw locations will be adjusted to fit the rod/line. In some embodiments, the system 10 may include a color-coded offset distance indicator (not shown) to provide the User with an indication of the distance each digitized screw position will be adjusted in the coronal plane as set forth above. If the User deems this an acceptable rod solution, the User selects the "Calculate Rod" button 272 to view the rod solution 274 and receive bend instructions or proceeds to another advanced feature as will be described in greater detail below.

According to another embodiment, the User may straighten a subset of the screw points within the construct (segmental coronal correction). Based on the sequence those points are inputted into the system, a best-fit segmental reference line is generated through the points in the direction of the last chosen point. If an inferior point is selected first and then a superior point is selected second, the system will draw the best-fit segmental reference line superiorly. Conversely, if a superior point is selected first and then an inferior point is selected second, the system will draw the best-fit segmental reference line inferiorly. Using the Coronal Straightening Menu, the User selects the percentage of correction desired. The system may include a color-coded offset distance indicator to provide the User with an indication of the distance each digitized screw position will be adjusted in the coronal plane as set forth above. If the User deems this an acceptable rod solution, the User selects the "Calculate Rod" button to view the rod solution and receive bend instructions or proceeds to another advanced feature as will be described in greater detail below.

According to another embodiment, segmental coronal correction may be achieved relative to the patient's central sacral vertical line (CSVL) instead of a best-fit segmental reference line running through two selected digitized screw locations. The CSVL is the vertical line passing through the center of the sacrum that may serve as the vertical reference line for the patient's coronal deformity as well as a guide for spinal correction in the coronal plane in accordance with the coronal assessment and correction features of the present disclosure.

Figure 63:
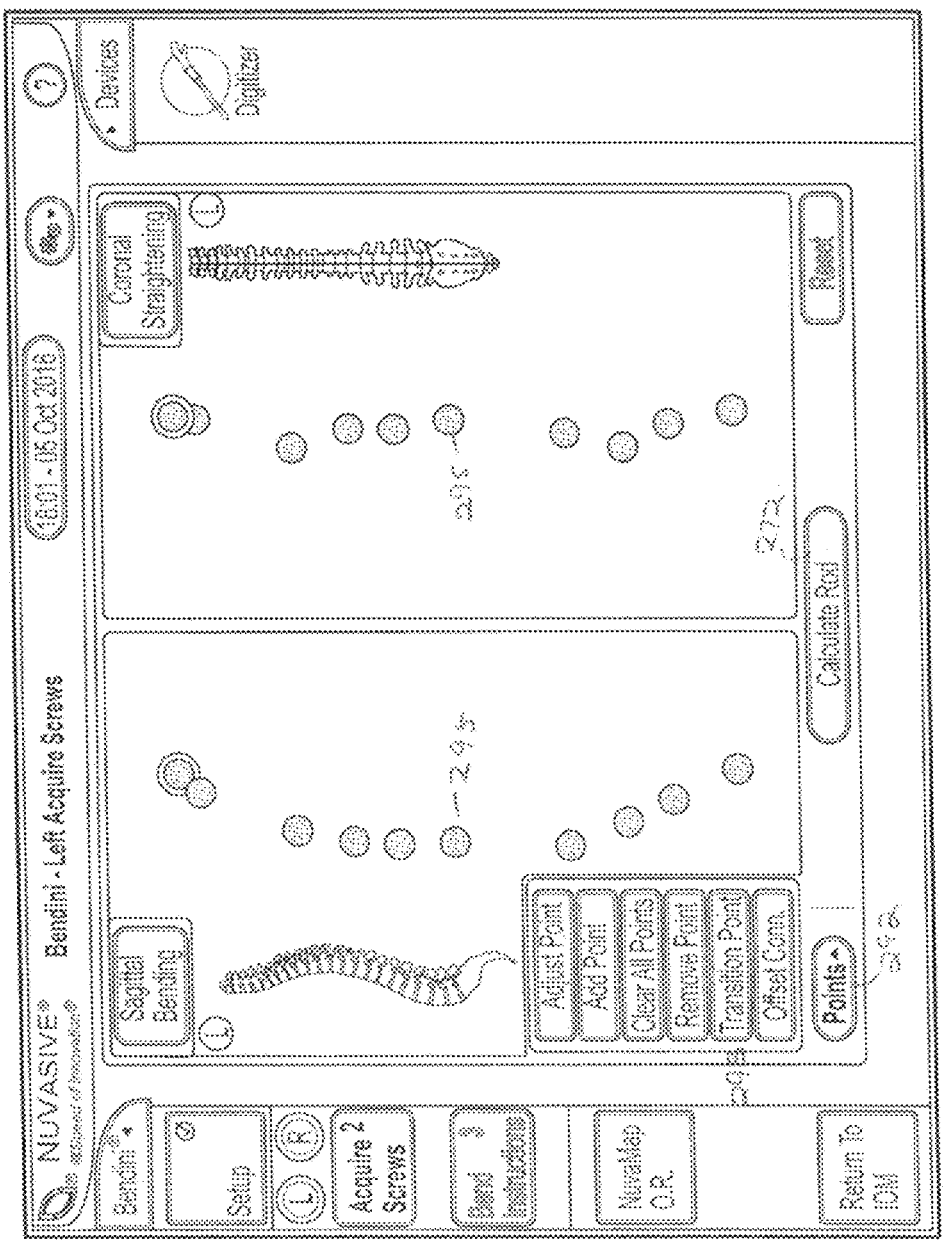
FIGS. 63-64 are screen shots illustrating an example Transition Rod screen according to one embodiment.
Figure 64:
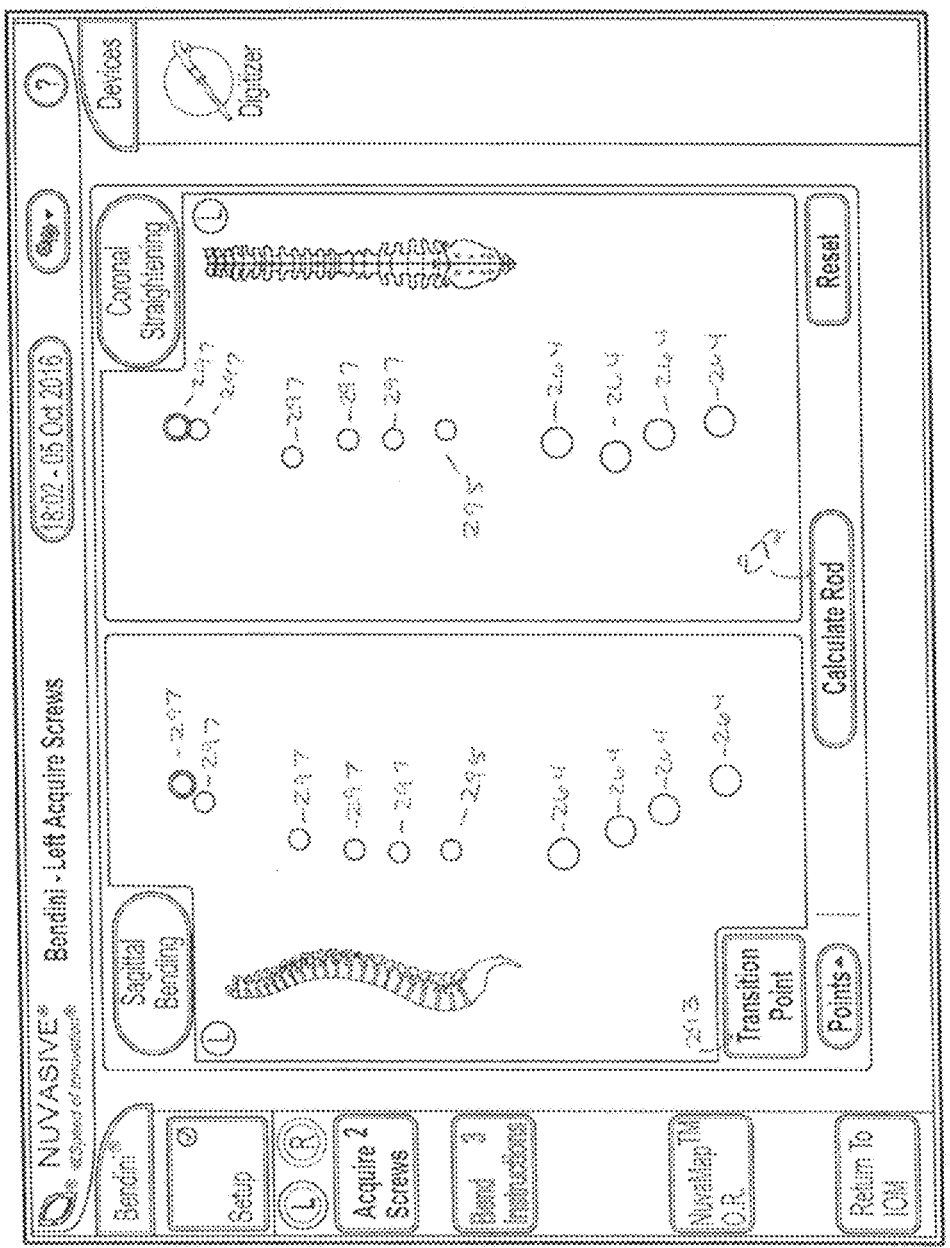
Figure 65:
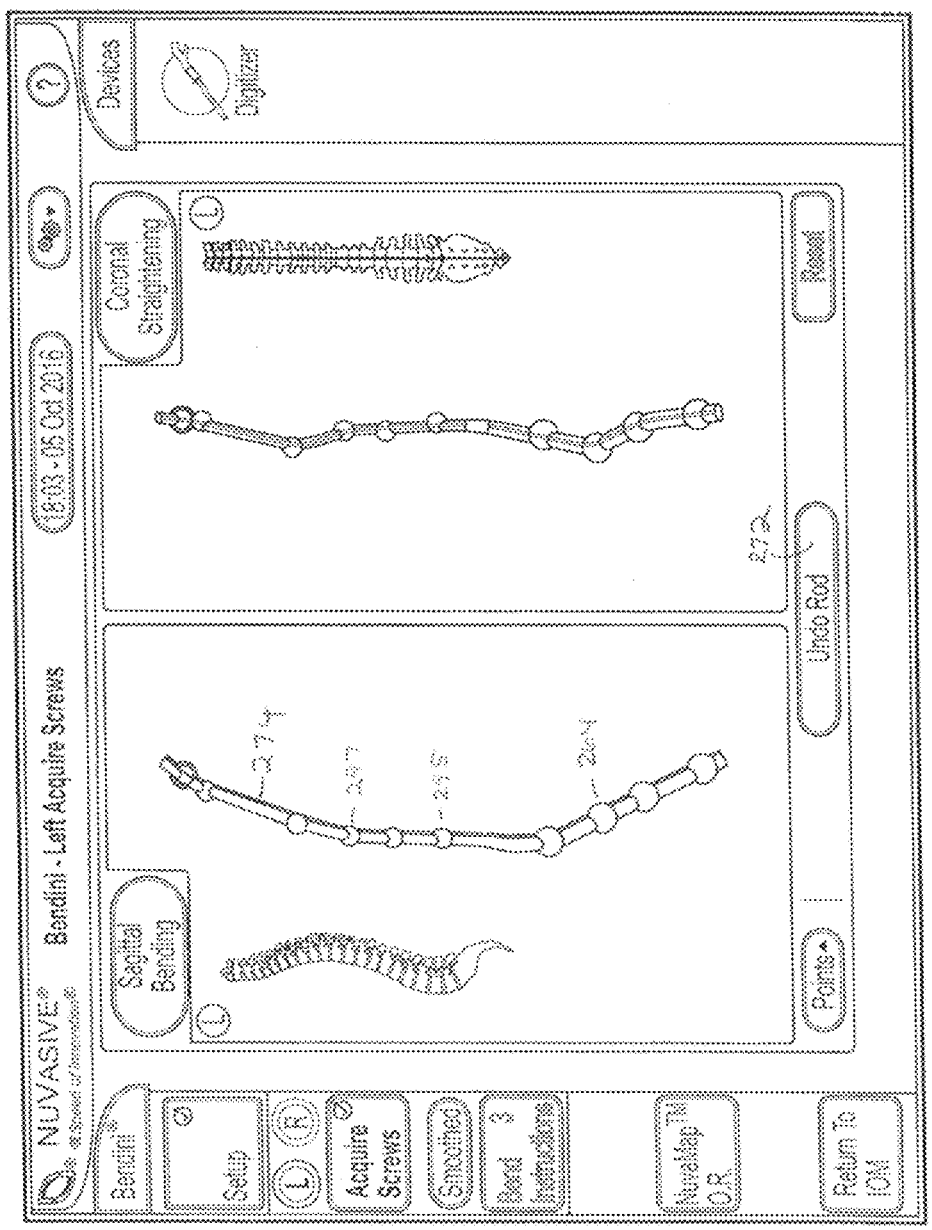
FIG. 65 is a screen shot illustrating an example of the rod preview screen for a transition rod according to one embodiment.
Figure 66:
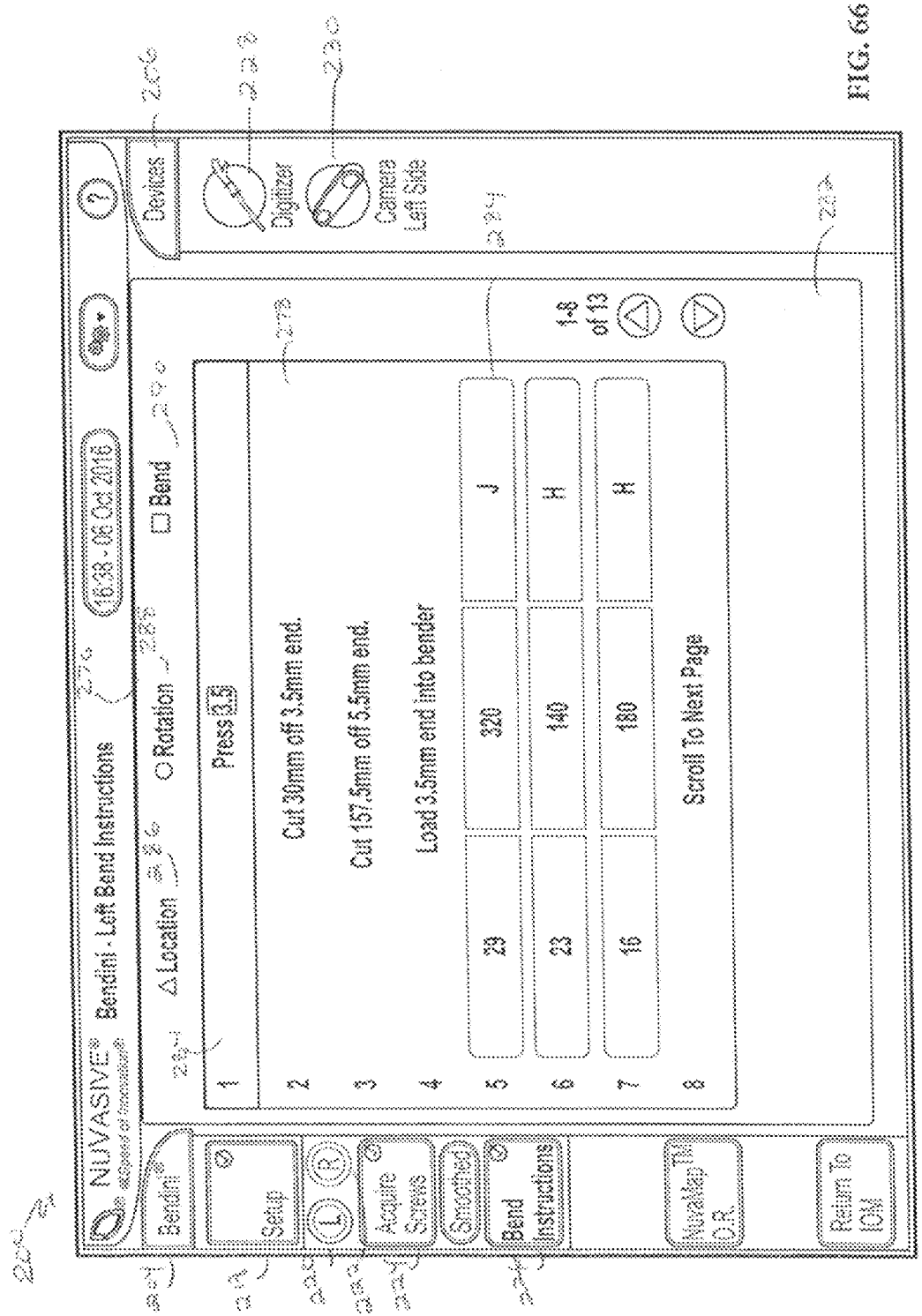
FIG. 66 is a screen shot illustrating an example rod bending instruction screen for a transition rod according to one embodiment.

According to another embodiment, as shown in FIGS. 63-65, in some cases, the rod may traverse the thoracic and cervical vertebra. In such embodiments, the appropriate rod may be a 5.5 mm to 3.5 mm transition rod to allow use of a smaller rod with the smaller screws in the cervical region, and a larger rod in the thoracic region for increased stability. It is necessary to identify the point of transition so that the rod may be properly bent for each region. As shown in FIG. 63, from the Points menu, the User will select the Transition Point button 293. The User will then identify the most inferior 3.5 mm screw 295. Once the transition point 295 is selected, all of the points 297 superior to the transition point will be smaller in size to indicate the smaller screws and rod in that region as shown in FIG. 64. The User may change the transition point 295 by selecting another point. Once the location of the transition screw point 295 is deemed acceptable, the User may press the "Calculate Rod" button 272 which initiates the curve calculation preferably using one of the algorithms discussed above. Once a rod solution has been calculated, a rod graphic 274 populates through the screw points 264, 295, 297 and a confirmation graphic (e.g., a check) may appear on the "Acquire Screws" button 224 to indicate that the system 10 has generated a rod solution. The graphic will show a larger 5.5 mm rod at the inferior screw points, 3.5 mm rod at the superior screw points, and the transition aligned at the selected transition point 295 as shown for example in FIG. 65. An exemplary set of bend instructions for a transition rod is shown in FIG. 66. The instruction direct the User to cut 30 mm off the 3.5 mm end and cut 157.5 mm of the 5.5 mm end. The cut to both ends ensures that the transition is aligned at the selected transition point 295.

Figure 67:
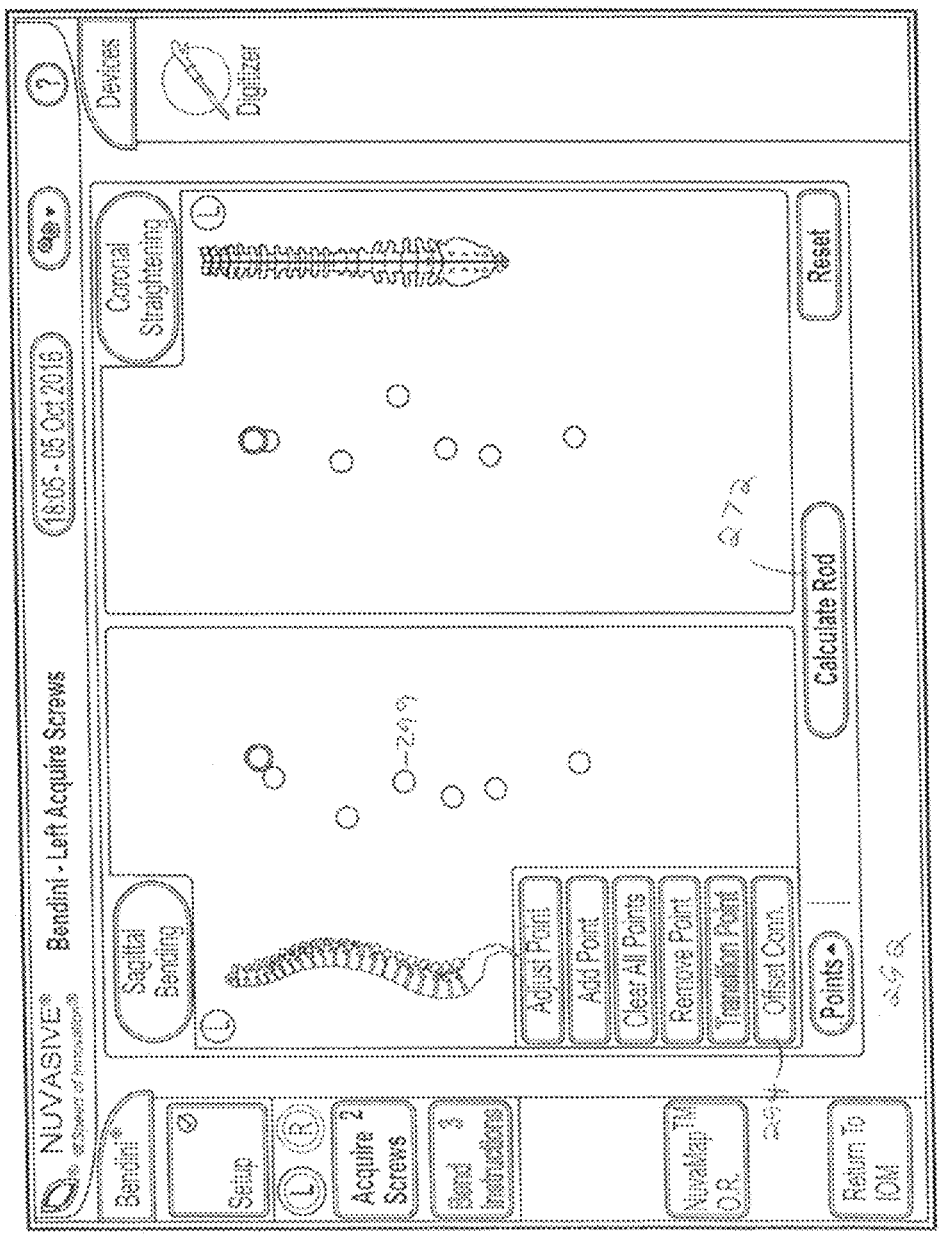
FIGS. 67-68 are screen shots illustrating an example Offset Connector screen according to one embodiment.
Figure 68:
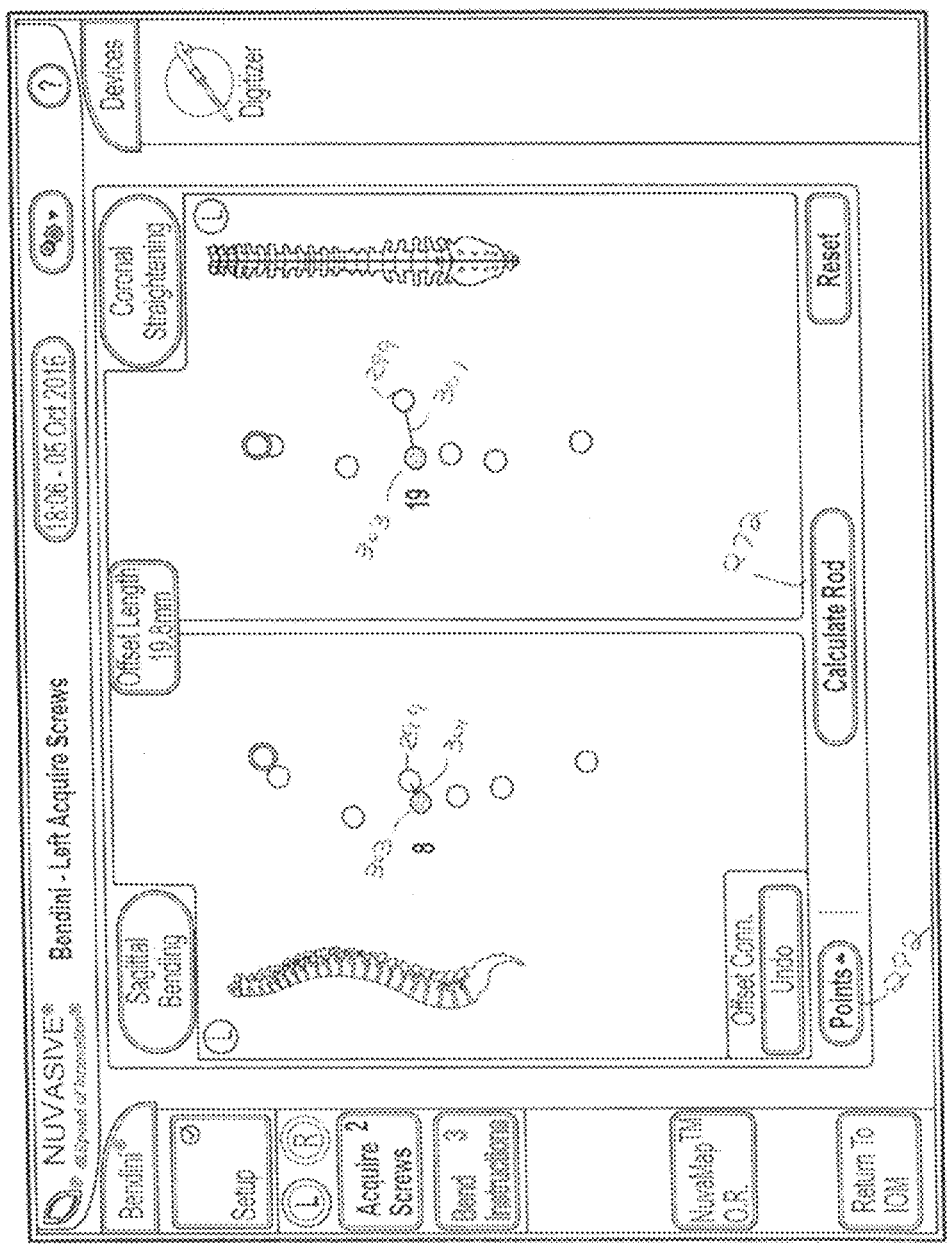
Figure 69:
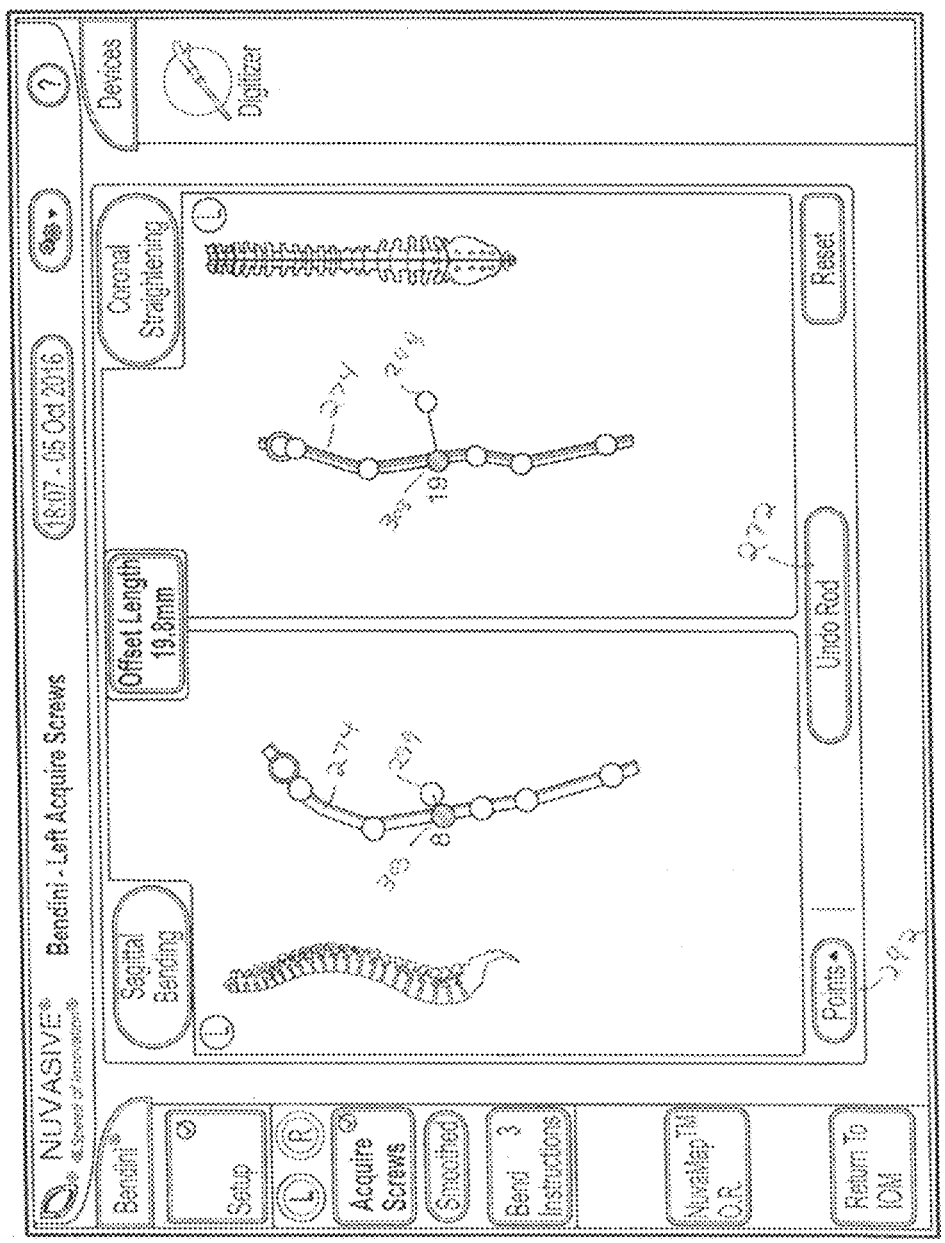
FIG. 69 is a screen shot illustrating an example of the rod preview screen for an offset connector according to one embodiment.

As shown in FIGS. 67-69, in some surgical procedures it may be necessary to add an offset connector to a cervical construct. The User may select the Points button 292 to access the menu. The User may then select the Offset connector button 294. The User may then select a point 299 to add an offset connect to that screw. The display will indicate the offset connector 301 as line connecting the selected point and the offset point 303. The offset point may be adjusted using the directional arrows. The display will indicate the distance between the selected point and the offset point as shown, for example in FIG. 68. Once satisfied with the adjusted points, the User may select "Calculate Rod" 272. Once "Calculate Rod" 272 has been selected, the system 10 generates a rod 274 in which the curve traverses the adjusted points, thereby creating a offset-specific rod as shown in FIG. 69.

Figure 70:
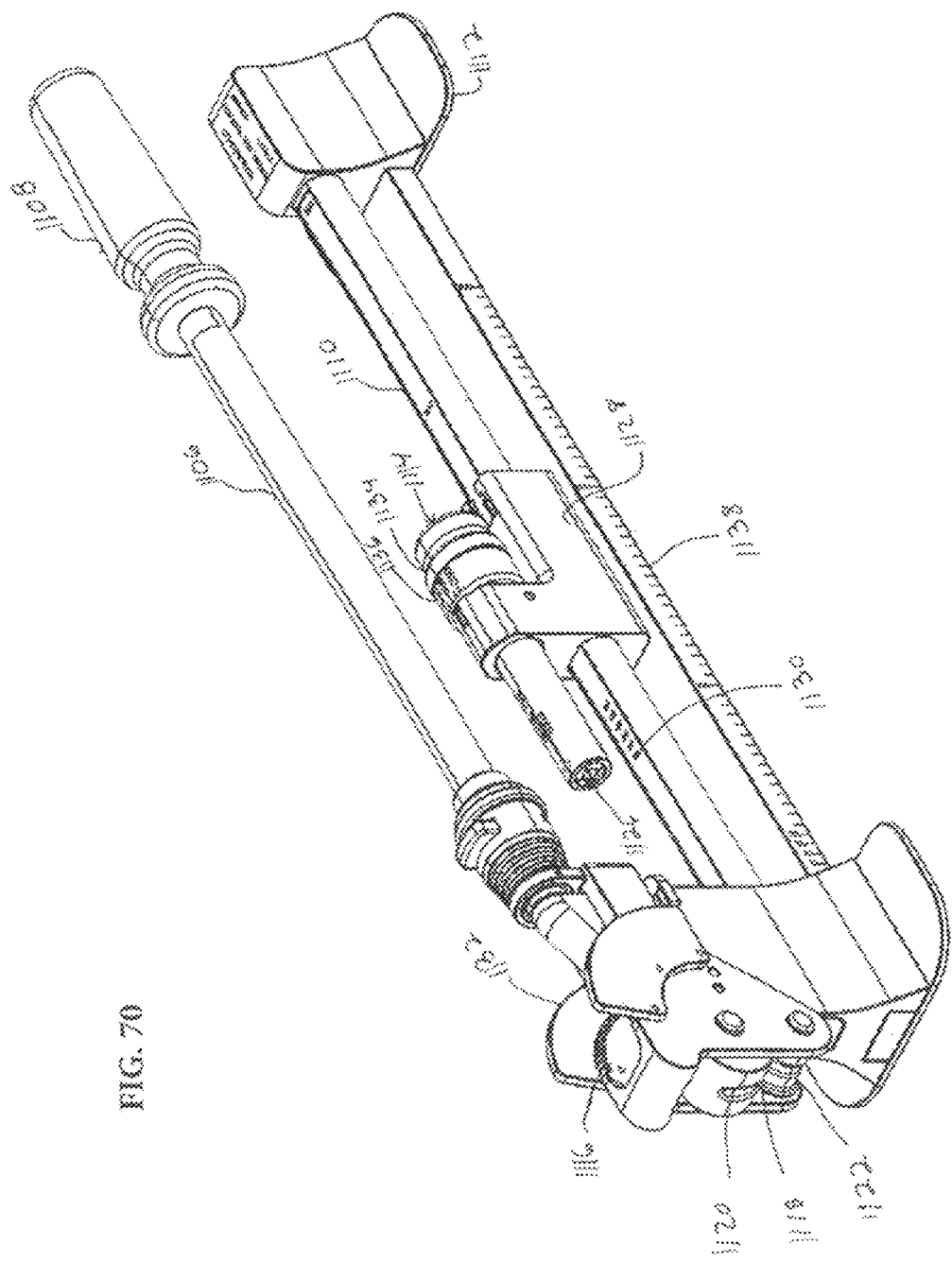
FIG. 70 is a perspective view of a mechanical rod bender according to one embodiment.

From one or many of the features discussed above, once the User has selected the desired rod solution, the User then executes the bends using a mechanical rod bender 18 like the embodiment depicted, for example in FIG. 70. It is contemplated that the mechanical rod bender 18 may be any bender that takes into account six degrees of freedom information as it effects bends onto a spinal rod. By way of example, according to one implementation, the mechanical rod bender 18 may be the bender described in commonly-owned U.S. Pat. No. 7,957,831 entitled "System and Device for Designing and Forming a Surgical Implant" patented Jun. 7, 2011, the disclosure of which is hereby incorporated by reference as if set forth in its entirety herein. According to a second implementation, the mechanical rod bender 18 may be the bender shown in FIG. 65. First and second levers 1106, 1110 are shown as is lever handle 1108 designed for grabbing the lever 1106 manually and a base 1112 for holding lever 1110 in a static position. Second lever 1110 has a rod pass through 1114 so that an infinitely long rod can be used as well as steady the rod during the bending process with the rod bending device 18. The User grabs handle 1108 and opens it to bend a particular rod by picking an angle on the angle gauge 1132 and closing the handle 1108 such that levers 1106, 1110 are brought closer together. The mechanical rod bender 18 in other embodiments could be produced to bend the rod during the handle opening movement as well. The rod moves through mandrel 1118 and in between moving die 1120 and fixed die 1122. The rod is bent between the two dies 1120, 1122. Gauges on the bender 18 allow the User to manipulate the rod in order to determine bend position, bend angle, and bend rotation. The rod is held in place by collet 1126. By sliding slide block 1128 along base 1112, the rod can be moved proximally and distally within the mechanical rod bender 18. Position may be measured by click stops 1130 at regular intervals along base 1112. Each click stop 1130 is a measured distance along the base 1112 and thus moving a specific number of click stops 1130 gives one a precise location for the location of a rod bend.

The bend angle is measured by using angle gauge 1132. Angle gauge 1132 has ratchet teeth 1116 spaced at regular intervals. Each ratchet stop represents five degrees of bend angle with the particular bend angle gauge 1132 as the handle 1106 is opened and closed. It is to be appreciated that each ratchet step may represent any suitable degree increment (e.g., between 0.25 degrees to 10 degrees). The bend rotation is controlled by collet knob 1134. By rotating collet knob 1134 either clockwise or counterclockwise, the User can set a particular rotation angle. The collet knob 1134 is marked with regular interval notches 1136 but this particular embodiment is continuously turnable and thus has infinite settings. Once a User turns knob 1134, the User can set the knob 1134 at a particular marking or in between or the like to determine a particular angle rotation to a high degree of accuracy. Additionally, base 1112 may have a ruler 1138 along its length to aid the User in measuring a rod intraoperatively.

According to another implementation, the rod bender 18 may be a pneumatic or motor-driven device which automatically adjusts the location, rotation and bend angle of the rod. By way of example, three motors may be utilized for each movement. A linear translator motor would move the rod in and out of the mandrel 1118 and moving die 1120. One rotational motor would rotate the rod and moving die 1120. The bend calculations could be converted into an interface program that would run to power and control the motors. The automated bender would lessen the possibility of User error in following the manual bend instructions. It would also increase the resolution or number of bends that can be imparted in the rod making for a smoother looking rod.

Method for Global Alignment

Figure 71:
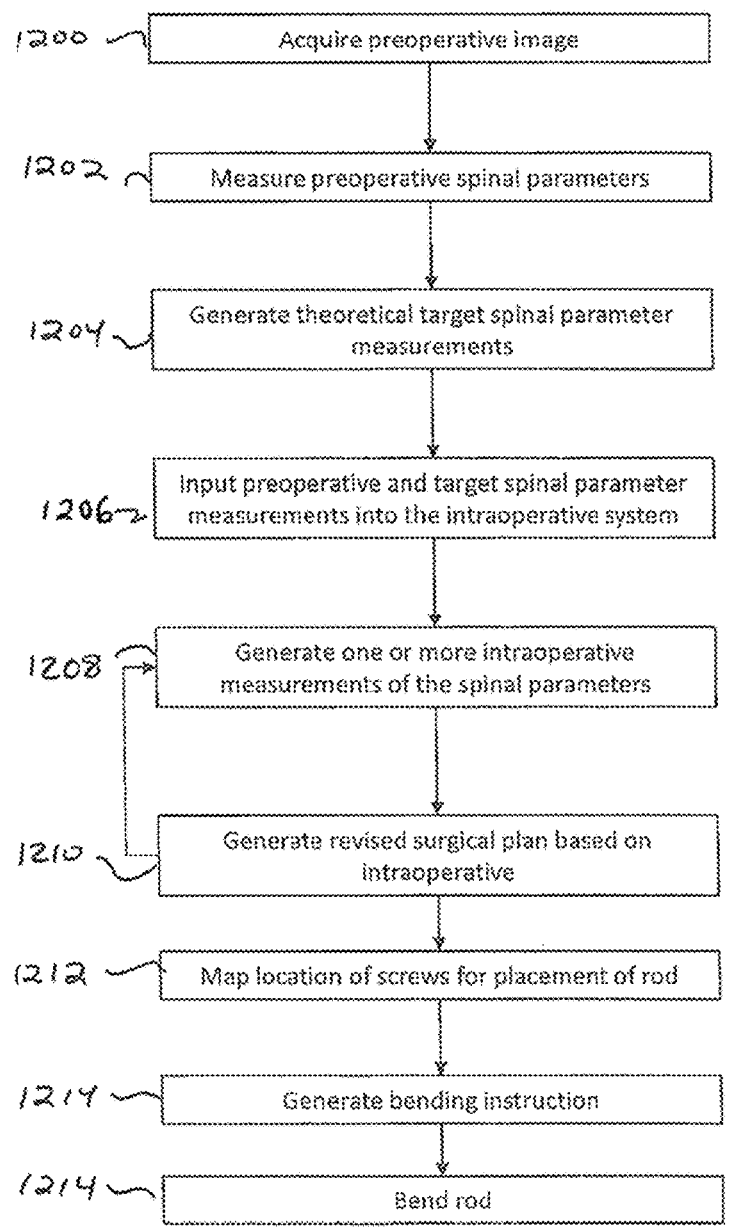
FIG. 71 is a flow chart for a method of global spinal alignment.

The flowchart in FIG. 71 provides an overview of an exemplary method for measuring, planning, and generating rod bending instructions for a more globally aligned spine. Briefly, according to one embodiment, one or more preoperative images of the spinal column are acquired (step 1200). Using a planning software and interface, the User inputs the images and measures the preoperative spinal parameters, which may include PI, LL, Superior LL, Inferior LL, C7PL, and TK in the thoracolumbar region and CL, ACL, TS, CSVA, and CBVA in the cervical region (step 1202). The user plans the surgical intervention to correct the defect, including determining optimal spinal parameters for a globally aligned spine (step 1204). If the User is satisfied with the surgical plan, the planned spinal parameter values are saved. When the patient is prepared for surgery, the pre-operative and planned spinal values are input into the system 10 (step 1206). The surgeon performs spinal surgery to correct the defect using the surgical plan as a guide as to appropriate implants and placement of screws and/or plates. During the surgery, the user may employ neuromonitoring systems. At any point during the surgery, but generally after placement of the implants and/or insertion of the screws or hoods for rod stabilization, the User will acquire intraoperative images of the spine and measure the spinal parameters taken during preoperative planning (step 1208). The measurement of spinal parameters will inform the surgeon as to the current state of the patient's alignment, provide a comparison to the pre-surgery deformity and/or the planned correction (step 1210). If the intraoperative surgical parameters differ from non-pathologic ranges, or if they differ from the planned values, the surgeon may undertake corrective measures including, for example, replacing the implants. The surgeon may make additional intraoperative assessments of the spinal parameters until the spine is aligned to the satisfaction of the surgeon (step 1208). The user then measures the location of each of the screws for the placement of the rod (step 1212). The user may make manual adjustments to the locations of the screws to correct the placement, and introduce additional lordosis or kyphosis, or correct other spinal misalignments. It will be appreciated that the intraoperative measurements of alignment and corrective adjustments to implants and screws may be repeated until the desired degree of alignment has been achieved.

Once the surgeon is satisfied that the screws are properly placed and located in the surgical software, rod bending instructions can be generated (step 1214). The rod bending instructions are used as a template for bending the rod using a mechanical bender (step 1214). When a properly bent rod has been formed, the rod is implanted in the patient and secured into the screws by a set screw. If desired, the surgeon may optionally perform additional intraoperative assessment of spinal alignment to confirm that the spinal surgery has corrected, to the extent desired or possible, deformity of the spine and has restored the patient's spinal alignment. When the surgeon is satisfied with the alignment, the surgery is completed.

We claim:

1. A system for global alignment of a spine during spinal surgery, the system comprising an imaging device, a spatial tracking system, a bending device, and, a control unit configured to:
   receive a planned target value of one or more spinal parameters;
   based on the planned target value of the one or more spinal parameters, determine one or more ranges corresponding to a desired correction in at least one of (i) a sagittal alignment and (ii) a coronal alignment of the spine;
   capture, via the imaging device and the spatial tracking system, one or more intraoperative fluoroscopy images;
   measure an intraoperative value of the one or more spinal parameters according to the one or more captured intraoperative fluoroscopy images;

compare the intraoperative value of the one or more spinal parameters with the planned target value of the spinal parameters;

based on the comparison, determine that the intraoperative value of the one or more spinal parameters is within the one or more ranges and measure a location of one or more screws; and calculate an instruction to bend a rod, via the bending device, to the location of the one or more screws.

2. A system for use during a surgical procedure, the system comprising:
an imaging device;
a rod bending device;
a control unit configured to:
obtain one or more preoperative measurements of an anatomical parameter of a patient;
obtain one or more planned target measurements of the anatomical parameter;
based on the planned target measurements of the anatomical parameter, determine one or more ranges corresponding to a desired correction in at least one of (i) a sagittal alignment and (ii) a coronal alignment of the spine;
obtain an intraoperative image from the imaging device;
measure an intraoperative measurement of the anatomical parameter; and
determine that the intraoperative measurement of the anatomical parameter is within the one or more ranges and calculate an instruction for bending a surgical rod.

3. The system of claim 2, wherein the anatomical parameter is a chin brow vertical angle.

4. The system of claim 3, wherein the chin brow axis is an angle of a patient's gaze relative to a horizontal position.

5. The system of claim 4, wherein the control unit displays to a user a color indication of the angle of the gaze.

6. The system of claim 2, wherein the anatomical parameter is a parameter correlated to a health related quality of life score.

7. The system of claim 2, wherein the anatomical parameter is a parameter correlated to the alignment of a patient's head over the patient's pelvis.

8. A method for assessing global alignment of the spine during a surgical procedure, the method comprising:
inputting a planned target value of one or more spinal parameters into a control unit;
based on the planned target value of the one or more spinal parameters, determining one or more ranges corresponding to a desired correction in at least one of (i) a sagittal alignment and (ii) a coronal alignment of the spine;
capturing one or more intraoperative fluoroscopy images into the control unit;
measuring an intraoperative value of the one or more spinal parameters according to the one or more captured intraoperative fluoroscopy images;
comparing the intraoperative value of the one or more spinal parameters with the planned target value of the spinal parameters;
based on the comparison, determining that the intraoperative value of the one or more spinal parameters is within the one or more ranges and measuring a location of one or more screws;
calculating an instruction to bend a rod to the location of the one or more screws; and
bending the rod according to the instruction.

9. The method of claim 8, wherein at least one of the spinal parameters is a chin brow vertical angle.

10. The method of claim 8, wherein the method further comprises locating a point on the brow, locating a point on the chin, calculating a line between the points, and calculating an angle between the line and a vertical axis.

11. The method of claim 8 further comprising, calculating a preoperative value of the one or more spinal parameters.

12. The method of claim 8 further comprising, calculating a second target value for the one or more spinal parameters based on the comparison of the intraoperative value with the planned target value.

13. The method of claim 8, wherein at least one of the spinal parameters is a parameter correlated to a health related quality of life score.

14. The method of claim 8, wherein the spinal parameter is a parameter correlated to the alignment of a patient's head over the patient's pelvis.

15. The method of claim 8, wherein at least one of the spinal parameters is cervical sagittal vertical axis.

16. The method of claim 8, wherein at least one of the spinal parameters is T1 slope.

17. The method of claim 8, wherein at least one of the spinal parameters is cervical lordosis.

* * * * *